US009150629B2

(12) United States Patent
Matschiner et al.

(10) Patent No.: US 9,150,629 B2
(45) Date of Patent: Oct. 6, 2015

(54) HUMAN TEAR LIPOCALINS WHICH BIND PCSK9 AND METHODS OF USE THEREOF

(71) Applicants: Pieris AG, Freising-Weihenstephan (DE); Daiichi Sankyo Company, Limited, Chuo-ku, Tokyo, Tokyo (JP)

(72) Inventors: Gabriele Matschiner, Munich (DE); Christine Rothe, Dauchau (DE); Andreas Hohlbaum, Paunzhausen (DE); Andrea Allersdorfer, Geisenhausen (DE); Rachida Siham Bel Aiba, Munich (DE); Marlon Hinner, Munich (DE); Alexander Wiedenmann, Neufahrn (DE); Bradley Lunde, Freising (DE); Shinji Yamaguchi, Tokyo (JP); Takahide Aburatani, Kashiwa (JP); Ryuji Hashimoto, Yachiyo (JP); Tohru Takahashi, Tokyo (JP); Chikako Nagasaki, Tokyo (JP); Futoshi Nara, Tokyo (JP); Tomohiro Nishizawa, Tokyo (JP)

(73) Assignee: DAIICHI SANKYO CO., LTD., Tokyo (JP)

( * ) Notice: Subject to any disclaimer, the term of this patent is extended or adjusted under 35 U.S.C. 154(b) by 0 days.

(21) Appl. No.: 14/208,629

(22) Filed: Mar. 13, 2014

(65) Prior Publication Data

US 2014/0288008 A1    Sep. 25, 2014

Related U.S. Application Data

(60) Provisional application No. 61/781,511, filed on Mar. 14, 2013.

(30) Foreign Application Priority Data

Jul. 4, 2013   (EP) .................................... 13175023

(51) Int. Cl.
*C07K 14/47*   (2006.01)
*G01N 33/573*   (2006.01)

(52) U.S. Cl.
CPC .............. *C07K 14/47* (2013.01); *G01N 33/573* (2013.01)

(58) Field of Classification Search
None
See application file for complete search history.

(56) References Cited

U.S. PATENT DOCUMENTS

| | | | |
|---|---|---|---|
| 5,728,553 A | 3/1998 | Goodey et al. | |
| 6,177,074 B1 | 1/2001 | Glue et al. | |
| 6,403,564 B1 | 6/2002 | Ganguly et al. | |
| 6,500,930 B2 | 12/2002 | Adamson | |
| 6,620,413 B1 | 9/2003 | DeSauvage et al. | |
| 8,598,317 B2 * | 12/2013 | Skerra et al. | 530/350 |
| 2003/0069395 A1 | 4/2003 | Sato et al. | |

FOREIGN PATENT DOCUMENTS

| | | |
|---|---|---|
| EP | 0 330 451 A2 | 8/1989 |
| EP | 0 361 991 A2 | 4/1990 |
| WO | WO 99/16873 A1 | 4/1999 |
| WO | WO 99/64016 A1 | 12/1999 |
| WO | WO 00/75308 A1 | 12/2000 |
| WO | WO 03/029462 A1 | 4/2003 |
| WO | WO 03/029463 A2 | 4/2003 |
| WO | WO 03/029471 A1 | 4/2003 |
| WO | WO 03/069395 A2 | 8/2003 |
| WO | WO 2005/019254 A1 | 3/2005 |
| WO | WO 2005/019255 A1 | 3/2005 |
| WO | WO 2005/019256 A2 | 3/2005 |
| WO | WO 2006/056464 A2 | 6/2006 |
| WO | WO 2007/038619 A2 | 4/2007 |
| WO | WO 2007/107563 A2 | 9/2007 |
| WO | WO 2008/015239 A2 | 2/2008 |
| WO | WO 2009/016043 A2 | 2/2009 |
| WO | WO 2012/004384 A2 | 1/2012 |

OTHER PUBLICATIONS

The Strategene Catalog, p. 39, 1988.*
Altschul, et al., "Basic local alignment search tool," *J. Mol. Biol.*, May 15, 1990, 215:403-410.
Altschul, et al., "Gapped BLAST and PSI-BLAST a new generation of protein database search programs," *Nucleic Acids Research*, Jul. 16, 1997, 25: 3389-3402.
Altuvia et al., "Ranking potential binding peptides to MHC molecules by a computational threading approach," *J. Mol. Biol.*, 1995, 249:244-250.
Amstutz et al., "In vitro display technologies novel developments and applications," *Current Opinion in Biotechnology*, 2001, 12:400-405.
Beaucage et al., "Deoxynucleoside phosphoramidites—A new class of key intermediates for deoxypolynucleotide synthesis," (1981) *Tetrahedron Letters*, 1981, 22(20):1859-1862.
Bittker et al., "Nucleic acid evolution and minimization by nonhomologous random recombination," *Nature Biotechnology*, Oct. 2002, 20:1024-1029.
Bjorck et al., "Streptococcal protein G, expressed by streptococci or by *Escherichia coli*, has separate binding sites," *Molecular Immunology*, Apr. 30, 1987, 24(10):1113-1122.
Breustedt et al., "The 1.8-A crystal structure of human tear lipocalin reveals an extended branched cavity," *The Journal of Biological Chemistry*, Jan. 7, 2005, 280(1):484-493.
Broders et al., "Hyperphage. Improving antibody presentation in phage display," *Methods in Molecular Biology*, 2003, 205:295-302.
Bruckdorfer et al.,"From production of peptides in milligram amounts for research to multi-tons quantities for drugs of the future," (2004) *Current Pharmaceutical Biotechnology*, 2004, 5:29-43.
Dennis et al., "Albumin binding as a general strategy for improving the pharmacokinetics of proteins," *The Journal of Biological Chemistry*, Sep. 20, 2002, 277(38):35035-35043.

(Continued)

Primary Examiner — Robert Landsman
(74) *Attorney, Agent, or Firm* — Foley & Lardner LLP

(57) ABSTRACT

The present disclosure relates to novel lipocalin muteins which bind to PCSK9. The disclosure also provides corresponding nucleic acid molecules encoding lipocalin muteins and methods for producing lipocalin muteins as well as their encoding nucleic acid molecules.

56 Claims, 27 Drawing Sheets

(56) References Cited

OTHER PUBLICATIONS

Figure 1:
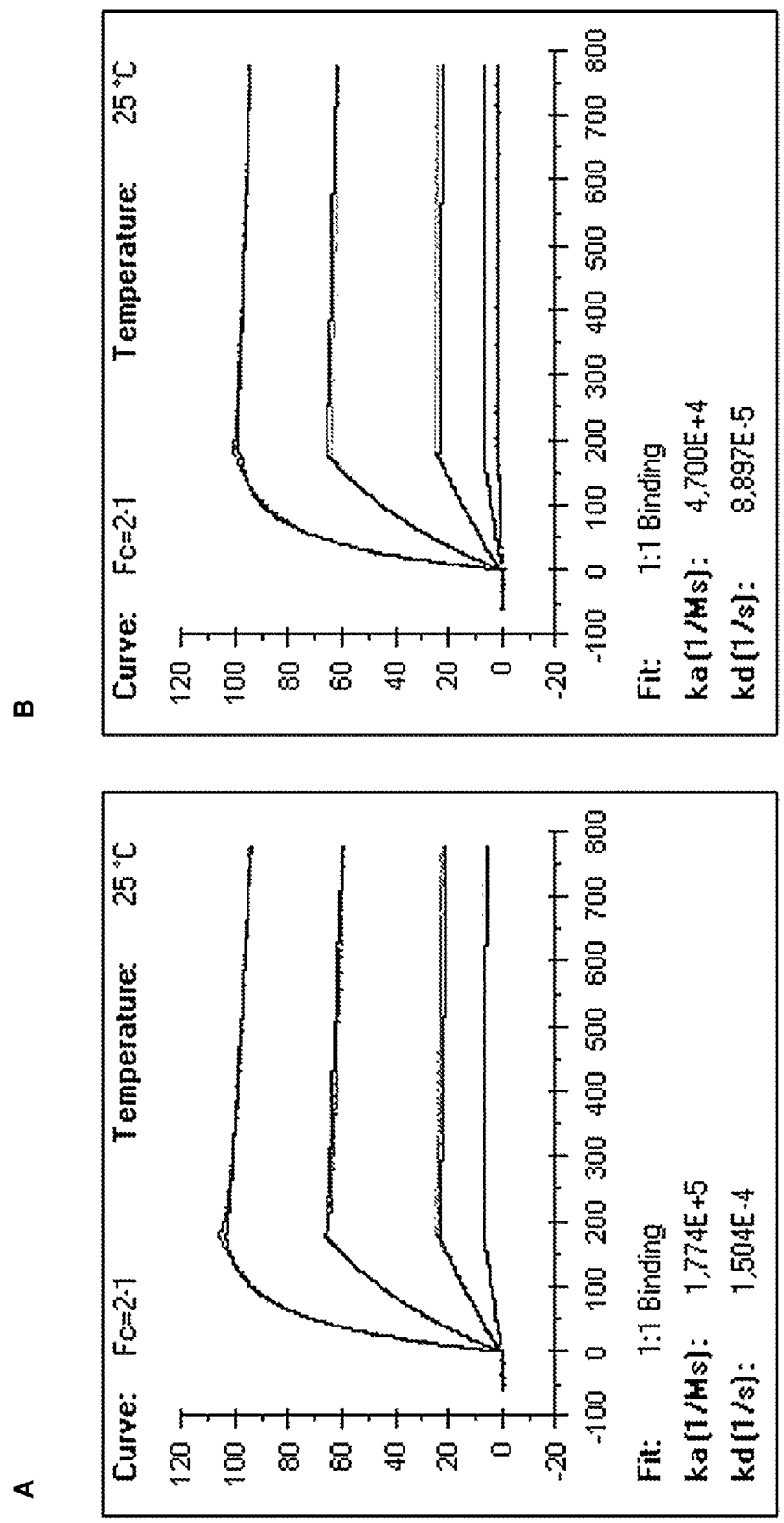
Figure 1:
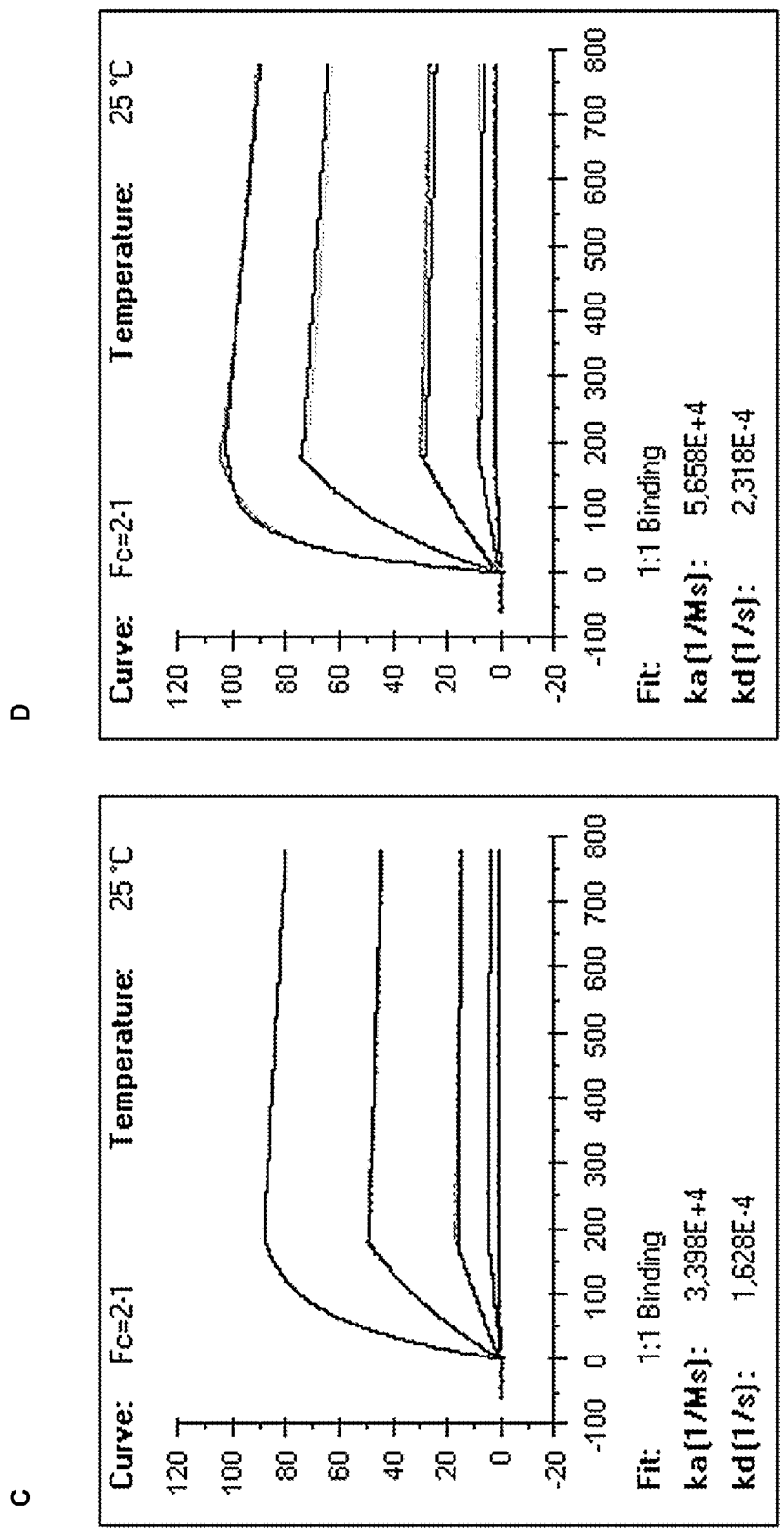

Fisher, et al., "Effects of pH and low density lipoprotein (LDL) on PCSK9-dependent LDL receptor regulation," *The Journal of Biological Chemistry*, Jul. 13, 2007, 282(28):20502-20512.
Flower et al., "The lipocalin protein family: Structural and sequence overview," *Biochimica et Biophysica Acta*, 2000, 1482:9-24.
Flower, "The lipocalin protein family structure and function," *Biochem. J.*, 1996, 318:1-14.
Fuertges et al., "The clinical efficacy of poly(ethylene glycol)-modified proteins," *Journal of Controlled Release*, 1990, 11:139-148.
Gaillard et al., "Diphtheria toxin receptor-targeted brain drug delivery," *International Congress Series*, 2005, 1277:185-198.
Gaillard et al., "Targeted delivery across the blood-brain barrier," *Expert Opin. Drug Deliv.*, 2005, 2(2):299-309.
Goetsch et al., "Identification of B- and T-cell epitopes of BB, a carrier protein derived from the G protein of *Streptococcus* strain G148," *Clinical and Diagnostic Lab Immunology*, Jan. 2003, 10(1):125-132.
Guss et al., "Structure of the IgG-binding regions of streptococcal protein G," *The EMBO Journal*, 1986, 5(7):1567-1575.
Hackbarth et al., "S-peptide epitope tagging for protein purification, expression monitoring, and localization in mammalian cells," *BioTechniques*, Nov. 2004, 37:835-839.
Horton et al., "Molecular biology of PCSK9 its role in LDL metabolism," *TRENDS in Biochemical Sciences*, 2006, 32(2):71-77.
Johansson et al., "Solution structure of the albumin-binding GA module a versatile bacterial protein domain," *J. Mol. Biol.*, 1997, 266:859-865.
Johansson et al., "Structure, specificity, and mode of interaction for bacterial albumin-binding modules," *The Journal of Biological Chemistry*, Mar. 8, 2002, 277(10):8114-8120.
Jonsson et al., "Engineering of a femtomolar affinity binding protein to human serum albumin," *Protein Engineering*, Design & Selection, 2008, 21(8):515-527.
Kay, B.K. et al., "High-throughput screening strategies to identify inhibitors of protein-protein interactions," *Molecular Diversity*, 1995, 1:139-140.
Kim et al., "High-affinity recognition of lanthanide(III) chelate complexes by a reprogrammed human lipocalin 2," *J. Am. Chem. Soc.*, 2009, 131(10):3565-3576.
König, T., & Skerra, A., "Use of an albumin-binding domain for the selective immobilisation of recombinant capture antibody fragments on ELISA plates," *Journal of Immunological Methods*, Jun. 8, 1998, 218:73-83.
Kraulis et al., "The serum albumin-binding domain of streptococcal protein G is a three-helical bundle a heteronuclear NMR study," *FEBS Letters*, Nov. 22, 1995, 378:190-194.
Lowman, H.B., "Bacteriophage display and discovery of peptide leads for drug development," *Annu. Rev. Biophys. Biomol. Struct*, 1997, 26:401-424.
Mateo et al., "Removal of amphipathic epitopes from genetically engineered antibodies: Production of modified immunoglobulins with reduced immunogenicity," *Hybridoma*, Aug. 30, 2000, 19(6):463-471.
Mayer, M. P., "A new set of useful cloning and expression vectors derived from pBlueScript," *Gene*, 1995, 163:41-46.
McBride et al., "An investigation of several deoxynucleoside phosphoramidites useful for synthesizing deoxyoligonucleotides," *Tetrahedron Letters*, 1983, 24(3):245-248.
Murakami, H et al., "Random insertion and deletion of arbitrary number of bases for codon-based random mutation of DNAs," *Nature Biotechnology*, Jan. 2002, 20:76-81.

Naureckiene et al., "Functional characterization of Narc 1, a novel proteinase related to proteinase K," *Archives Biochemistry and Biophysics*, Sep. 4, 2003, 420:55-67.
Olsson et al., "Structure and evolution of the repetitive gene encoding streptococcal protein G," *Eur. J. Biochem.*, May 15, 1987, 168:319-324.
Osborn, B.L. et al., "Pharmacokinetic and pharmacodynamic studies of a human serum albumin-interferon-3B1 fusion protein in cynomolgus monkeys" *The Journal of Pharmacology and Experimental Therapeutics*, Jul. 12, 2002, 303(2):540-548.
Pervaiz et al., "Homology and structure-function correlations between αl-acid glycoprotein and serum retinol-binding protein and its relatives," *FASEB J.*, May 14, 1987, 1:209-214.
Peterson et al., "PCSK9 function and physiology," *Journal of Lipid Research*, 2008, 49:1595-1599.
Pini et al., "Phage Display and Colony Filter Screening for High-Throughput Selection of Antibody Libraries," *Combinatorial Chemistry High Throughput Screening*, 2002, 5:503-510.
Rashid S., et al., "Decreased plasma cholesterol and hypersensitivity to statins in mice lacking Pcsk9," *PNAS*, Apr. 15, 2005, 102(15):5374-5379.
Redl, B. et al., "cDNA cloning and sequencing reveals human tear prealbumin to be a member of the lipophilic-ligand carrier protein superfamily," *The Journal of Biological Chemistry*, Oct. 5, 1992, 267(28):20282-20287.
Rodi et al., "Phage-display technology—finding a needle in a vast molecular haystack," *Current Opinion in Biotechnology*, 1999, 10:87-93.
Rozak et al., "Using offset recombinant polymerase chain reaction to identify functional determinants in a common family," *Biochemistry*, 2006, 45:3263-3271.
Sawyer et al., "Protein structure one fold among many," *Nature*, Jun. 25, 1987, 327:659.
Schlehuber et al., "A novel type of receptor protein, based on the lipocalin scaffold, with specificity for digoxigenin," *J. Mol. Biol.*, 2000, 297:1105-1120.
Schlehuber et al., "Duocalins, engineered ligand-binding proteins with dual specificity derived from the lipocalin fold," *Biol. Chem.*, Sep. 2001, 382:1335-1342.
Schmidt et al., "Molecular interaction between the strep-tag affinity peptide and its cognate target, streptavidin," *J. Mol. Biol.*, 1996, 255:753-766.
Sleep et al., "Albumin as a versatile platform for drug half-life extension." *Biochimica et Biophysica Acta*, 2013, 1830(12):5526-5534.
Smith et al., "Identification of common molecular subsequences," *J. Mol. Biol.*, 1981, 147:195-197.
Stemmer et al., "Single-step assembly of a gene and entire plasmid from large numbers of oligodeoxyribonucleotides," *Gene*, Jun. 23, 1995, 164:49-53.
Vajo et al., "Genetically engineered insulin analogs: diabetes in the new millennium," *Pharmacological Reviews*, 2000, 52(1):1-9.
Venturi et al., "High level production of functional antibody fab fragments in an oxidizing bacterial cytoplasm," *J. Mol. Biol.*, 2002, 315:1-8.
Virnekäs B, et al., "Trinucleotide phosphoramidites: Ideal reagents for the synthesis of mixed oligonucleotides," *Nucleic Acids Research*, Nov. 1, 1994, 22(25):5600-5607.
Wang et al., "Expanding the genetic code of *Escherichia coli*," *Science*, Apr. 20, 2001, 292:498-500.
Wang et al., "Expanding the genetic code," *Chem. Comm.*, 2002, 1:1-11.
Wilson et al., "The use of mRNA display to select high-affinity protein-binding peptides," *PNAS*, Mar. 27, 2001, 98(7):3750-3755.
Zaccolo et al., "An approach to random mutagenesis of DNA using mixtures of triphosphate derivatives of nucleoside analogues," *J. Mol. Biol.*, 1996, 255:589-603.

* cited by examiner

Figure 3:
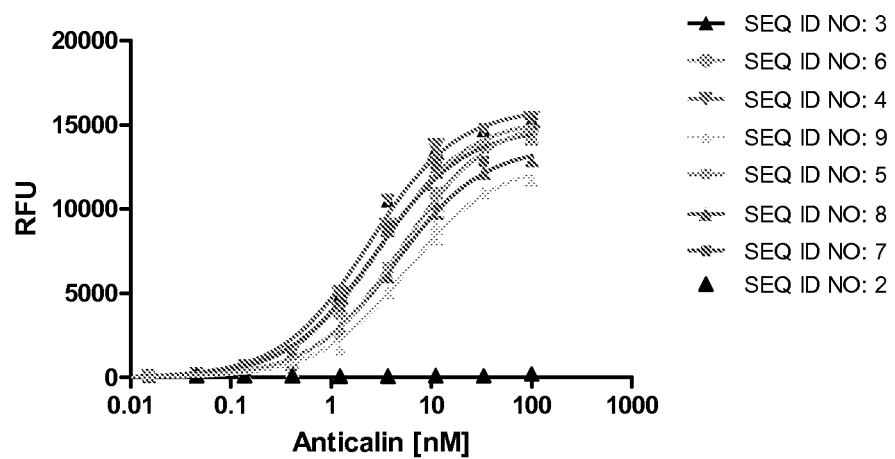
Figure 3:
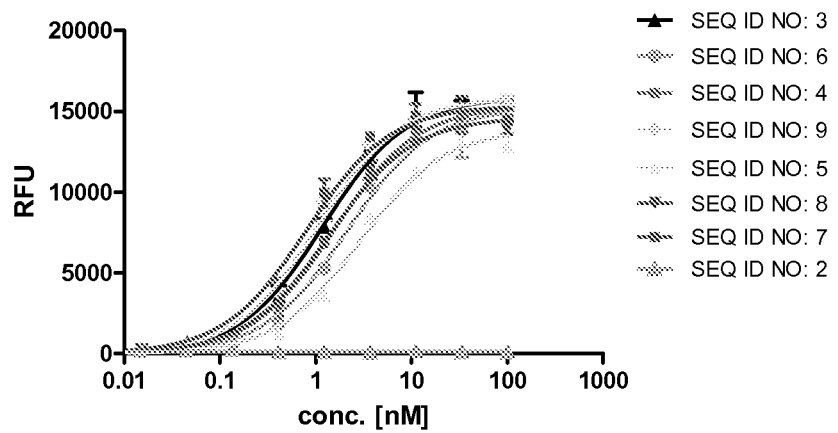

Figure 3 (cont'd)
Fig. 3C
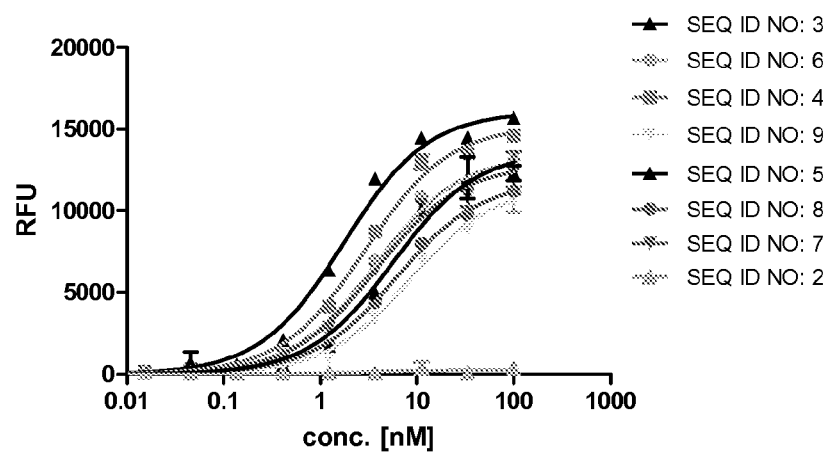
Fig. 3D
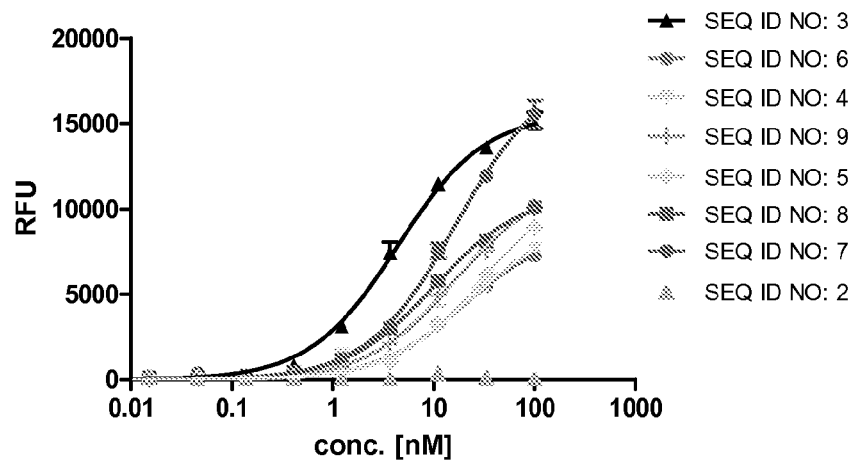

Figure 10

| Molecule | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| SEQ ID NO: 1 | H | H | L | L | A | S | D | E | E | I | Q | D | V | S | G | T | W | Y | L | K | A | M | T |
| SEQ ID NO: 2 | | | | | A | S | D | E | E | I | Q | D | V | S | G | T | W | Y | L | K | A | M | T |
| SEQ ID NO: 3 | | | | | A | S | D | E | E | I | Q | D | V | S | G | T | W | Y | L | K | A | M | T |
| SEQ ID NO: 4 | | | | | A | S | D | E | E | I | Q | D | V | S | G | T | W | Y | L | K | A | M | T |
| SEQ ID NO: 5 | | | | | A | S | D | E | E | I | Q | D | V | S | G | T | W | Y | L | K | A | M | T |
| SEQ ID NO: 6 | | | | | A | S | D | E | E | I | Q | D | V | S | G | T | W | Y | L | K | A | M | T |
| SEQ ID NO: 7 | | | | | A | S | D | E | E | I | Q | D | V | S | G | T | W | Y | L | K | A | M | T |
| SEQ ID NO: 8 | | | | | A | S | D | E | E | I | Q | D | V | S | G | T | W | Y | L | K | A | M | T |
| SEQ ID NO: 9 | | | | | A | S | D | E | E | I | Q | D | V | S | G | T | W | Y | L | K | A | M | T |
| SEQ ID NO: 10 | | | | | A | S | D | E | E | I | Q | D | V | S | G | T | W | Y | L | K | A | M | T |
| SEQ ID NO: 11 | | | | | A | S | D | E | E | I | Q | D | V | S | G | T | W | Y | L | K | A | M | T |
| SEQ ID NO: 103 | | | | | A | S | D | E | E | I | Q | D | V | S | G | T | W | Y | L | K | A | M | T |
| SEQ ID NO: 13 | | | | | A | S | D | E | E | I | Q | D | V | S | G | T | W | Y | L | K | A | M | T |
| SEQ ID NO: 14 | | | | | A | S | D | E | E | I | Q | D | V | S | G | T | W | Y | L | K | A | M | T |
| SEQ ID NO: 15 | | | | | A | S | D | E | E | I | Q | D | V | S | G | T | W | Y | L | K | A | M | T |
| SEQ ID NO: 16 | | | | | A | S | D | E | E | I | Q | D | V | S | G | T | W | Y | L | K | A | M | T |
| SEQ ID NO: 17 | | | | | A | S | D | E | E | I | Q | D | V | S | G | T | W | Y | L | K | A | M | T |
| SEQ ID NO: 18 | | | | | A | S | D | E | E | I | Q | D | V | S | G | T | W | Y | L | K | A | M | T |
| SEQ ID NO: 104 | | | | | A | S | D | E | E | I | Q | D | V | S | G | T | W | Y | L | K | A | M | T |
| SEQ ID NO: 20 | | | | | A | S | D | E | E | I | Q | D | V | S | G | T | W | Y | L | K | A | M | T |
| SEQ ID NO: 21 | | | | | A | S | D | E | E | I | Q | D | V | S | G | T | W | Y | L | K | A | M | T |
| SEQ ID NO: 22 | | | | | A | S | D | E | E | I | Q | D | V | S | G | T | W | Y | L | K | A | M | T |
| SEQ ID NO: 23 | | | | | A | S | D | E | E | I | Q | D | V | S | G | T | W | Y | L | K | A | M | T |
| SEQ ID NO: 24 | | | | | A | S | D | E | E | I | Q | D | V | S | G | T | W | Y | L | K | A | M | T |
| SEQ ID NO: 25 | | | | | A | S | D | E | E | I | Q | D | V | S | G | T | W | Y | L | K | A | M | T |
| SEQ ID NO: 26 | | | | | A | S | D | E | E | I | Q | D | V | S | G | T | W | Y | L | K | A | M | T |
| SEQ ID NO: 27 | | | | | A | S | D | E | E | I | Q | D | V | S | G | T | W | Y | L | K | A | M | T |
| SEQ ID NO: 28 | | | | | A | S | D | E | E | I | Q | D | V | S | G | T | W | Y | L | K | A | M | T |

Figure 10 (Continued)

Figure 10 (Continued)

| 48 | 49 | 50 | 51 | 52 | 53 | 54 | 55 | 56 | 57 | 58 | 59 | 60 | 61 | 62 | 63 | 64 | 65 | 66 | 67 | 68 |
|---|---|---|---|---|---|---|---|---|---|---|---|---|---|---|---|---|---|---|---|---|
| N | L | E | E | A | K | V | T | M | L | I | S | G | R | C | Q | E | V | K | A | V | L |
| N | L | E | E | A | K | V | T | M | L | L | S | G | R | S | Q | E | V | K | A | V | L |
| N | L | E | E | A | K | V | T | M | M | Y | A | R | A | F | Q | E | V | K | A | V | L |
| N | L | E | E | A | K | V | T | M | S | Y | A | G | R | S | Q | E | V | K | A | V | L |
| N | L | E | E | A | K | V | T | M | Q | W | R | G | R | S | Q | E | V | K | A | V | L |
| N | L | E | E | A | K | V | T | M | N | H | A | G | R | S | Q | E | V | K | A | V | L |
| N | L | E | E | A | K | V | T | M | F | Q | W | G | R | S | Q | E | V | K | A | V | L |
| N | L | E | E | A | K | V | T | M | H | T | P | G | R | S | Q | E | V | K | A | V | L |
| N | L | E | E | A | K | V | T | M | F | R | R | G | R | S | Q | E | V | K | A | V | L |
| N | L | E | E | A | K | V | T | M | M | Y | A | G | R | S | Q | E | V | K | A | V | L |
| G | L | E | E | A | K | V | T | M | Q | Y | A | G | R | S | Q | G | V | K | V | A | V | L |
| N | L | E | E | A | K | V | T | M | M | Y | A | G | R | S | Q | E | V | K | A | V | L |
| N | L | E | E | A | K | V | T | M | M | Y | A | G | R | S | Q | E | V | K | V | A | V | L |
| N | L | E | E | A | K | V | T | M | M | Y | A | G | R | S | Q | E | V | K | A | V | L |
| N | L | E | E | A | K | V | T | M | M | Y | A | G | R | S | Q | E | V | K | A | V | L |
| N | L | E | E | A | K | V | T | M | M | Y | A | G | R | S | Q | E | V | K | A | V | L |
| N | L | E | E | A | K | V | T | M | N | W | W | G | R | S | Q | E | V | K | A | V | L |
| N | L | E | E | A | K | V | T | M | N | W | W | G | R | S | Q | E | V | K | A | V | L |
| N | L | E | E | A | K | V | T | M | N | W | W | G | R | S | Q | E | V | K | A | V | L |
| N | L | E | E | A | K | V | T | M | N | W | R | G | R | S | Q | D | V | K | A | V | L |
| N | L | E | E | A | K | V | T | M | N | W | W | G | R | S | Q | E | V | K | A | V | L |

| 118 | 119 | 120 | 121 | 122 | 123 | 124 | 125 | 126 | 127 | 128 | 129 | 130 | 131 | 132 | 133 | 134 | 135 | 136 | 137 | 138 | 139 |
|---|---|---|---|---|---|---|---|---|---|---|---|---|---|---|---|---|---|---|---|---|---|
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |
| R | D | P | K | N | N | L | E | A | L | E | D | F | E | K | A | A | G | A | R | G | L |

Figure 10 (Continued)

| 140 | 141 | 142 | 143 | 144 | 145 | 146 | 147 | 148 | 149 | 150 | 151 | 152 | 153 | 154 | 155 | 156 | 157 | 158 |
|-----|-----|-----|-----|-----|-----|-----|-----|-----|-----|-----|-----|-----|-----|-----|-----|-----|-----|-----|
| S | T | E | S | - | L | - | P | R | Q | S | E | T | C | S | P | G | S | D |
| S | T | E | S | - | L | - | P | R | Q | S | E | T | S |  S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |
| S | T | E | S | - | L | - | P | R | Q | S | E | T | S | S | P | G | | |

Figure 14

| Molecule | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| SEQ ID NO: 1 | H | H | L | L | A | S | D | E | E | I | Q | D | V | S | G | T | W | Y | L | K | A | M | T |
| SEQ ID NO: 13 |   |   |   |   | A | S | D | E | E | I | Q | D | V | S | G | T | W | Y | L | K | A | M | T |
| SEQ ID NO: 63 |   |   |   |   | A | S | D | E | E | I | Q | D | V | S | G | T | W | Y | L | K | A | M | T |
| SEQ ID NO: 64 |   |   |   |   | A | S | D | E | E | I | Q | D | V | S | G | T | W | Y | L | K | A | M | T |
| SEQ ID NO: 65 |   |   |   |   | A | S | D | E | E | I | Q | D | V | S | G | T | W | Y | L | K | A | M | T |
| SEQ ID NO: 66 |   |   |   |   | A | S | D | E | E | I | Q | D | V | S | G | T | W | Y | L | K | A | M | T |
| SEQ ID NO: 67 |   |   |   |   | A | S | D | E | E | I | Q | D | V | S | G | T | W | Y | L | K | A | M | T |
| SEQ ID NO: 68 |   |   |   |   | A | S | D | E | E | I | Q | D | V | S | G | T | W | Y | L | K | A | M | T |
| SEQ ID NO: 69 |   |   |   |   | A | S | D | E | E | I | Q | D | V | S | G | T | W | Y | L | K | A | M | T |
| SEQ ID NO: 70 |   |   |   |   | A | S | D | E | E | I | Q | D | V | S | G | T | W | Y | L | K | A | M | T |
| SEQ ID NO: 71 |   |   |   |   | A | S | D | E | E | I | Q | D | V | S | G | T | W | Y | L | K | A | M | T |
| SEQ ID NO: 22 |   |   |   |   | A | S | D | E | E | I | Q | D | V | S | G | T | W | Y | L | K | A | M | T |
| SEQ ID NO: 62 |   |   |   |   | A | S | D | E | E | I | Q | D | V | S | G | T | W | Y | L | K | A | M | T |

| Molecule | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|---|---|---|---|---|---|---|---|
| SEQ ID NO: 1  | V | D | R | F | F | P | E | M | N | L | E | S | V | T | P | M | T | L | T | T | L | E | G | G |
| SEQ ID NO: 13 | V | D | E | S | R | G | D | A | I | W | T | S | V | T | P | M | T | L | T | T | L | E | G | G |
| SEQ ID NO: 63 | V | D | F | S | R | G | D | A | I | W | T | S | V | T | P | M | T | L | T | T | L | E | G | G |
| SEQ ID NO: 64 | V | D | F | S | R | G | D | A | L | W | T | S | V | T | P | M | T | L | T | T | L | E | G | G |
| SEQ ID NO: 65 | V | D | F | S | R | G | D | A | V | W | T | S | V | T | P | M | T | L | T | T | L | E | G | G |
| SEQ ID NO: 66 | V | D | F | S | R | G | D | A | F | W | T | S | V | T | P | M | T | L | T | T | L | E | G | G |
| SEQ ID NO: 67 | V | D | F | S | R | G | D | A | Y | W | T | S | V | T | P | M | T | L | T | T | L | E | G | G |
| SEQ ID NO: 68 | V | D | F | S | R | G | D | A | L | W | T | S | V | T | P | M | T | L | T | T | L | E | G | G |
| SEQ ID NO: 69 | V | D | F | S | R | G | D | A | M | W | T | S | V | T | P | M | T | L | T | T | L | E | G | G |
| SEQ ID NO: 70 | V | D | F | S | R | G | D | A | T | W | T | S | V | T | P | M | T | L | T | T | L | E | G | G |
| SEQ ID NO: 71 | V | D | F | S | R | G | D | A | N | W | T | S | V | T | P | M | T | L | T | T | L | E | G | G |
| SEQ ID NO: 22 | V | D | R | F | K | I | A | S | W | P | R | S | V | T | P | M | T | L | T | T | L | E | G | G |
| SEQ ID NO: 62 | V | D | R | F | K | I | A | S | W | P | R | S | V | T | P | M | T | L | T | T | L | E | G | G |

| 140 | 141 | 142 | 143 | 144 | 145 | 146 | 147 | 148 | 149 | 150 | 151 | 152 | 153 | 154 | 155 | 156 | 157 | 158 |
|---|---|---|---|---|---|---|---|---|---|---|---|---|---|---|---|---|---|---|
| S | T | E | S | I | L | – | P | R | Q | S | E | T | C | S | P | G | S | D |
| S | T | E | S | I | L | – | P | R | Q | S | E | T | S | S | P | G | | |
| S | T | E | S | I | L | – | P | R | Q | S | E | T | S | S | P | G | | |
| S | T | E | S | I | L | – | P | R | Q | S | E | T | S | S | P | G | | |
| S | T | E | S | I | L | – | P | R | Q | S | E | T | S | S | P | G | | |
| S | T | E | S | I | L | – | P | R | Q | S | E | T | S | S | P | G | | |
| S | T | E | S | I | L | – | P | R | Q | S | E | T | S | S | P | G | | |
| S | T | E | S | I | L | – | P | R | Q | S | E | T | S | S | P | G | | |
| S | T | E | S | I | L | – | P | R | Q | S | E | T | S | S | P | G | | |
| S | T | E | S | I | L | – | P | R | Q | S | E | T | S | S | P | G | | |

US 9,150,629 B2

SEQUENCE LISTING

<160> NUMBER OF SEQ ID NOS: 107

<210> SEQ ID NO 1
<211> LENGTH: 158
<212> TYPE: PRT
<213> ORGANISM: Homo sapiens
<220> FEATURE:
<223> OTHER INFORMATION: Human tear lipocalin

<400> SEQUENCE: 1

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 2
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 2

Ala Ser Asp Glu Glu Ile Gln Asp Val Ser Gly Thr Trp Tyr Leu Lys
1               5                   10                  15

Ala Met Thr Val Asp Arg Glu Phe Pro Glu Met Asn Leu Glu Ser Val
            20                  25                  30

Thr Pro Met Thr Leu Thr Thr Leu Glu Gly Gly Asn Leu Glu Ala Lys
        35                  40                  45

Val Thr Met Leu Ile Ser Gly Arg Ser Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Leu His Gly Lys Pro Val Pro Gly Val Trp Leu Val
            100                 105                 110

Gly Arg Asp Pro Lys Asn Asn Leu Glu Ala Leu Glu Asp Phe Glu Lys
        115                 120                 125

```
Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 3
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 3

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Lys Thr Asp Glu Pro Gly Lys Tyr Thr Ala Met Gly Gly Ser His
65                  70                  75                  80

Val Ala Tyr Ile Ile Arg Ser His Val Lys Asp His Tyr Ile Phe Tyr
                85                  90                  95

Ser Glu Gly Pro Tyr Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 4
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 4

Ala Ser Asp Glu Glu Ile Gln Asp Val Ser Gly Thr Trp Tyr Leu Lys
1               5                   10                  15

Ala Met Thr Val Asp Trp Gln Cys Asp Thr Gly Leu Trp Thr Ser Val
            20                  25                  30

Thr Pro Met Thr Leu Thr Thr Leu Glu Gly Gly Asn Leu Glu Ala Lys
        35                  40                  45

Val Thr Met Ser Tyr Ala Gly Ala Phe Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95
```

```
Ser Glu Gly Glu Cys Gly Gly Trp Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 5
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 5

Ala Ser Asp Glu Glu Ile Gln Asp Val Ser Gly Thr Trp Tyr Leu Lys
1               5                   10                  15

Ala Met Thr Val Asp His Glu Trp Asn Gly His Tyr Tyr Thr Ser Val
            20                  25                  30

Thr Pro Met Thr Leu Thr Thr Leu Glu Gly Gly Asn Leu Glu Ala Lys
        35                  40                  45

Val Thr Met Ser Tyr Arg Gly Arg Ser Gln Glu Val Lys Ala Val Leu
    50                  55                  60

Glu Lys Thr Asp Glu Pro Gly Lys Tyr Thr Ala Pro Gly Gly Gln His
65                  70                  75                  80

Val Ala Tyr Ile Ile Arg Ser His Val Lys Asp His Tyr Ile Phe Tyr
                85                  90                  95

Ser Glu Gly Ser Trp Pro Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 6
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 6

Ala Ser Asp Glu Glu Ile Gln Asp Val Ser Gly Thr Trp Tyr Leu Lys
1               5                   10                  15

Ala Met Thr Val Asp Phe Thr Asp Asn Ser Pro Met Phe Thr Ser Val
            20                  25                  30

Thr Pro Met Thr Leu Thr Thr Leu Glu Gly Gly Asn Leu Glu Ala Lys
        35                  40                  45

Val Thr Met Gln Tyr Ala Gly Arg Ser Gln Glu Val Lys Ala Val Leu
```

```
                50                  55                  60
Glu Lys Thr Asp Glu Pro Gly Lys Tyr Thr Ala Ile Gly Gly Thr His
 65                  70                  75                  80

Val Ala Tyr Ile Ile Arg Ser His Val Lys Asp His Tyr Ile Phe Tyr
                 85                  90                  95

Ser Glu Gly Ala Glu Arg Gly Arg Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 7
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 7

Ala Ser Asp Glu Glu Ile Gln Asp Val Ser Gly Thr Trp Tyr Leu Lys
  1               5                  10                  15

Ala Met Thr Val Asp Arg Phe Lys Ile Ala Ser Trp Pro Arg Ser Val
                 20                  25                  30

Thr Pro Met Thr Leu Thr Thr Leu Glu Gly Gly Asn Leu Glu Ala Lys
             35                  40                  45

Val Thr Met Asn Trp Trp Gly Arg Ser Gln Glu Val Lys Ala Val Leu
         50                  55                  60

Glu Lys Thr Asp Glu Pro Gly Lys Tyr Thr Ala Gln Gly Gly Ser His
 65                  70                  75                  80

Val Ala Tyr Ile Ile Arg Ser His Val Lys Asp His Tyr Ile Phe Tyr
                 85                  90                  95

Ser Glu Gly Asn Arg Gln Gly Asp Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 8
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 8

Ala Ser Asp Glu Glu Ile Gln Asp Val Ser Gly Thr Trp Tyr Leu Lys
  1               5                  10                  15
```

```
Ala Met Thr Val Asp Phe Lys Gly Pro Thr Pro Leu Trp Thr Ser Val
            20                  25                  30

Thr Pro Met Thr Leu Thr Thr Leu Glu Gly Gly Asn Leu Glu Ala Lys
        35                  40                  45

Val Thr Met Phe His Ala Gly Arg Ser Gln Glu Val Lys Ala Val Leu
 50                  55                  60

Glu Lys Thr Asp Glu Pro Gly Lys Tyr Thr Ala Tyr Gly Gly Arg His
 65                  70                  75                  80

Val Ala Tyr Ile Ile Arg Ser His Val Lys Asp His Tyr Ile Phe Tyr
                 85                  90                  95

Ser Glu Gly Ala Ser Val Gly Asn Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150
```

<210> SEQ ID NO 9
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 9

```
Ala Ser Asp Glu Glu Ile Gln Asp Val Ser Gly Thr Trp Tyr Leu Lys
 1               5                  10                  15

Ala Met Thr Val Asp Thr Glu His Leu Ala Asp Trp Ala Asn Ser Val
            20                  25                  30

Thr Pro Met Thr Leu Thr Thr Leu Glu Gly Gly Asn Leu Glu Ala Lys
        35                  40                  45

Val Thr Met His Gln Pro Gly Arg Ser Gln Glu Val Lys Ala Val Leu
 50                  55                  60

Glu Lys Thr Asp Glu Pro Gly Lys Tyr Thr Ala Ile Gly Gly Ser His
 65                  70                  75                  80

Val Ala Tyr Ile Ile Arg Ser His Val Lys Asp His Tyr Ile Phe Tyr
                 85                  90                  95

Ser Glu Gly Ala Tyr Pro Gly Ser Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150
```

<210> SEQ ID NO 10
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

-continued

<223> OTHER INFORMATION: Mutein of human tear lipocalin

<400> SEQUENCE: 10

Ala Ser Asp Glu Glu Ile Gln Asp Val Ser Gly Thr Trp Tyr Leu Lys
1               5                   10                  15

Ala Met Thr Val Asp Arg Ala Asp Met Gly Asp Trp Pro Asn Ser Val
            20                  25                  30

Thr Pro Met Thr Leu Thr Thr Leu Glu Gly Gly Asn Leu Glu Ala Lys
        35                  40                  45

Val Thr Met Phe Thr Arg Gly Arg Ser Gln Glu Val Lys Ala Val Leu
    50                  55                  60

Glu Lys Thr Asp Glu Pro Gly Lys Tyr Thr Ala Thr Gly Gly Glu His
65                  70                  75                  80

Val Ala Tyr Ile Ile Arg Ser His Val Lys Asp His Tyr Ile Phe Tyr
                85                  90                  95

Ser Glu Gly Thr Leu Thr Gly Arg Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 11
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 11

Ala Ser Asp Glu Glu Ile Gln Asp Val Ser Gly Thr Trp Tyr Leu Lys
1               5                   10                  15

Ala Met Thr Val Asp Trp Arg Leu Asp Asn Glu Leu Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Lys Thr Asp Glu Pro Gly Lys Tyr Thr Ala Gln Gly Gly Ser His
65                  70                  75                  80

Val Ala Tyr Ile Ile Arg Ser His Val Lys Asp His Tyr Ile Phe Tyr
                85                  90                  95

Ser Glu Gly Pro Arg Asn Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 12

```
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 12
```

Ala Ser Asp Glu Glu Ile Gln Asp Val Ser Gly Thr Trp Tyr Leu Lys
1               5                   10                  15

Ala Met Thr Leu Asp Trp Gln Cys Asp Thr Gly Leu Trp Thr Ser Val
            20                  25                  30

Thr Pro Met Thr Leu Thr Thr Leu Glu Gly Gly Asn Leu Glu Ala Lys
        35                  40                  45

Val Thr Met Ser Tyr Ala Gly Ala Phe Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Gly Gly Trp Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

```
<210> SEQ ID NO 13
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 13
```

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Arg Thr Asp Glu Pro Gly Lys Tyr Thr Thr Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro His Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg

```
                130                 135                 140
Gln Ser Glu Thr Ser Ser Pro Gly
145                 150

<210> SEQ ID NO 14
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 14

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
50                  55                  60

Glu Lys Thr Asp Glu Pro Gly Lys Tyr Thr Ala Met Gly Gly Ser His
65                  70                  75                  80

Val Ala Tyr Ile Thr Arg Ser His Val Lys Asp His Tyr Ile Phe Tyr
                85                  90                  95

Ser Glu Gly Pro His Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 15
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 15

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Ile Leu Glu Gly Gly Asn Leu Glu Ala Lys
        35                  40                  45

Val Thr Met Met Tyr Ala Gly Arg Ser Gln Gly Val Lys Val Val Leu
50                  55                  60

Glu Lys Thr Asp Glu Pro Gly Lys Tyr Thr Ala Met Gly Gly Ser Gln
65                  70                  75                  80

Val Ala Tyr Ile Ile Arg Ser His Val Lys Asp His Tyr Ile Phe Tyr
                85                  90                  95
```

```
Pro Glu Gly Pro Tyr Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 16
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 16

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Lys Thr Asp Glu Pro Gly Lys Tyr Thr Thr Met Gly Gly Ser His
65                  70                  75                  80

Val Ala Tyr Ile Ile Arg Ser His Val Lys Asp His Tyr Ile Phe Tyr
                85                  90                  95

Ser Glu Gly Pro Tyr Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 17
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 17

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60
```

Glu Lys Thr Asp Glu Pro Gly Lys Tyr Thr Ala Ser Gly Gly Ser His
65                  70                  75                  80

Val Ala Tyr Ile Ile Arg Ser His Val Lys Asp His Tyr Ile Phe Tyr
                85                  90                  95

Ser Glu Gly Pro His Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 18
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 18

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
                20                  25                  30

Thr Pro Met Thr Leu Thr Ala Leu Glu Gly Gly Gly Leu Glu Ala Lys
        35                  40                  45

Val Thr Met Met Tyr Ala Gly Arg Ser Gln Glu Val Lys Val Val Leu
    50                  55                  60

Glu Lys Thr Asp Glu Pro Gly Lys Tyr Thr Ala Met Gly Gly Ser His
65                  70                  75                  80

Gly Ala Tyr Ile Thr Arg Ser His Val Lys Asp His Tyr Ile Phe Tyr
                85                  90                  95

Ser Glu Gly Pro Tyr Arg Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 19
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 19

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val

```
                    20                  25                  30
Thr Pro Met Thr Leu Thr Thr Leu Glu Gly Gly Asn Met Glu Ala Lys
            35                  40                  45

Val Thr Met Met Tyr Ala Gly Arg Ser Gln Glu Val Lys Ala Val Leu
        50                  55                  60

Glu Lys Thr Asp Glu Pro Gly Lys Tyr Thr Ala Met Gly Gly Ser His
65                  70                  75                  80

Val Ala Tyr Ile Ile Arg Ser His Val Lys Asp His Tyr Ile Phe Tyr
                85                  90                  95

Ser Glu Gly Leu Tyr Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 20
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 20

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
            35                  40                  45

Val Thr Met Met Tyr Ala Gly Arg Ser Gln Glu Val Lys Ala Val Leu
        50                  55                  60

Glu Lys Thr Asp Glu Pro Gly Lys Tyr Thr Val Met Gly Gly Ser His
65                  70                  75                  80

Val Ala Ser Ile Ile Arg Ser His Val Lys Asp His Tyr Ile Phe Tyr
                85                  90                  95

Pro Glu Gly Pro Tyr Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 21
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin
```

<400> SEQUENCE: 21

| Ala | Ser | Asp | Glu | Glu | Ile | Gln | Asp | Val | Ser | Gly | Thr | Trp | Tyr | Leu | Lys |
| 1 | | | | 5 | | | | | 10 | | | | | 15 | |

| Ala | Met | Thr | Val | Asp | Phe | Ser | Arg | Gly | Asp | Ala | Ile | Trp | Thr | Ser | Val |
| | | | 20 | | | | | 25 | | | | | 30 | | |

| Thr | Pro | Met | Thr | Leu | Thr | Thr | Leu | Glu | Gly | Gly | Asn | Leu | Glu | Ala | Lys |
| | | | 35 | | | | | 40 | | | | | 45 | | |

| Val | Thr | Met | Met | Tyr | Ala | Gly | Arg | Ser | Gln | Glu | Val | Lys | Ala | Val | Leu |
| | 50 | | | | | 55 | | | | | 60 | | | | |

| Glu | Lys | Thr | Asp | Glu | Pro | Gly | Lys | Tyr | Thr | Ala | Met | Gly | Gly | Ser | His |
| 65 | | | | | 70 | | | | | 75 | | | | | 80 |

| Val | Ala | Tyr | Ile | Leu | Arg | Ser | His | Val | Lys | Asp | His | Tyr | Ile | Phe | Tyr |
| | | | | 85 | | | | | 90 | | | | | 95 | |

| Ser | Glu | Gly | Pro | His | Gln | Gly | Ala | Pro | Val | Pro | Gly | Val | Trp | Leu | Val |
| | | | | 100 | | | | | 105 | | | | | 110 | |

| Gly | Arg | Asp | Pro | Lys | Asn | Asn | Leu | Glu | Ala | Leu | Glu | Asp | Phe | Glu | Lys |
| | | | | 115 | | | | | 120 | | | | | 125 | |

| Ala | Ala | Gly | Ala | Arg | Gly | Leu | Ser | Thr | Glu | Ser | Ile | Leu | Ile | Pro | Arg |
| | | | 130 | | | | | 135 | | | | | 140 | | |

| Gln | Ser | Glu | Thr | Ser | Ser | Pro | Gly |
| 145 | | | | | 150 | | |

<210> SEQ ID NO 22
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 22

| Ala | Ser | Asp | Glu | Glu | Ile | Gln | Asp | Val | Ser | Gly | Thr | Trp | Tyr | Leu | Lys |
| 1 | | | | 5 | | | | | 10 | | | | | 15 | |

| Ala | Met | Thr | Val | Asp | Arg | Phe | Lys | Ile | Ala | Ser | Trp | Pro | Arg | Ser | Val |
| | | | 20 | | | | | 25 | | | | | 30 | | |

| Thr | Pro | Met | Thr | Leu | Thr | Thr | Leu | Glu | Gly | Gly | Asn | Leu | Glu | Ala | Lys |
| | | | 35 | | | | | 40 | | | | | 45 | | |

| Val | Thr | Met | Asn | Trp | Trp | Gly | Arg | Ser | Gln | Glu | Val | Lys | Ala | Val | Leu |
| | 50 | | | | | 55 | | | | | 60 | | | | |

| Glu | Arg | Thr | Asp | Glu | Pro | Gly | Lys | Tyr | Thr | Ala | Gln | Gly | Asp | Arg | His |
| 65 | | | | | 70 | | | | | 75 | | | | | 80 |

| Val | Ala | Tyr | Ile | Ile | Arg | Ser | His | Val | Lys | Asp | His | Tyr | Ile | Phe | Tyr |
| | | | | 85 | | | | | 90 | | | | | 95 | |

| Ser | Glu | Gly | Asn | Leu | Gln | Gly | Glu | Thr | Val | Pro | Gly | Val | Trp | Leu | Val |
| | | | | 100 | | | | | 105 | | | | | 110 | |

| Gly | Arg | Asp | Pro | Lys | Asn | Asn | Leu | Glu | Ala | Leu | Glu | Asp | Phe | Glu | Lys |
| | | | | 115 | | | | | 120 | | | | | 125 | |

| Ala | Ala | Gly | Ala | Arg | Gly | Leu | Ser | Thr | Glu | Ser | Ile | Leu | Ile | Pro | Arg |
| | | | 130 | | | | | 135 | | | | | 140 | | |

| Gln | Ser | Glu | Thr | Ser | Ser | Pro | Gly |
| 145 | | | | | 150 | | |

<210> SEQ ID NO 23
<211> LENGTH: 152

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 23

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
            20                  25                  30

Thr Pro Met Thr Leu Thr Thr Leu Gly Gly Asn Leu Glu Ala Lys
        35                  40                  45

Val Thr Met Asn Trp Trp Gly Arg Ser Gln Glu Val Lys Ala Val Leu
    50                  55                  60

Glu Lys Thr Asp Glu Pro Gly Lys Tyr Thr Ala Gln Gly Gly Ser His
65                  70                  75                  80

Val Glu His Ile Ile Arg Ser His Val Lys Asp His Tyr Ile Phe Tyr
                85                  90                  95

Ser Lys Gly Asn Leu Gln Gly Glu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 24
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 24

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Trp Gly Arg Ser Gln Glu Val Lys Ala Val Leu
    50                  55                  60

Glu Lys Thr Asp Glu Pro Gly Lys Tyr Thr Ala Gln Gly Gly Ser His
65                  70                  75                  80

Val Glu Tyr Ile Ile Arg Ser His Val Lys Asp His Tyr Ile Phe Tyr
                85                  90                  95

Ser Glu Gly Asn Leu Gln Gly Glu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140
```

```
Gln Ser Glu Thr Ser Ser Pro Gly
145                 150

<210> SEQ ID NO 25
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 25

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Trp Gly Arg Ser Gln Asp Val Lys Ala Val Leu
    50                  55                  60

Gly Lys Thr Asp Glu Pro Gly Lys Tyr Thr Ala Gln Gly Asp Ser His
65                  70                  75                  80

Val Ser Tyr Ile Ile Arg Ser His Val Lys Asp His Tyr Ile Leu Tyr
                85                  90                  95

Ser Val Gly Asn Leu Gln Gly Glu Thr Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 26
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 26

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Trp Gly Arg Ser Gln Glu Val Lys Ala Val Leu
    50                  55                  60

Glu Lys Thr Asp Glu Pro Gly Lys Tyr Thr Ala Val Gly Gly Ser His
65                  70                  75                  80

Val Ala Tyr Ile Ile Arg Ser His Val Lys Asp His Tyr Ile Phe Tyr
                85                  90                  95

Ser Glu Gly Lys Leu Gln Gly Glu Pro Val Pro Gly Val Trp Leu Val
```

```
                    100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 27
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 27

Ala Ser Asp Glu Glu Ile Gln Asp Val Ser Gly Thr Trp Tyr Leu Lys
1               5                   10                  15

Ala Met Thr Val Asp Arg Phe Lys Ile Gly Ser Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Arg Gly Arg Ser Gln Glu Val Lys Ala Val Leu
    50                  55                  60

Glu Lys Thr Asp Glu Pro Gly Lys Tyr Thr Ala Gln Gly Gly Ser His
65                  70                  75                  80

Val Ala Tyr Ile Ile Arg Ser His Val Lys Asp His Tyr Ile Phe Tyr
                85                  90                  95

Ser Glu Gly Lys Leu Gln Gly Glu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 28
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 28

Ala Ser Asp Glu Glu Ile Gln Asp Val Ser Gly Thr Trp Tyr Leu Lys
1               5                   10                  15

Ala Met Thr Val Asp Arg Phe Lys Ile Gly Ala Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Trp Gly Arg Ser Gln Glu Val Lys Ala Val Leu
    50                  55                  60
```

```
Glu Lys Thr Asp Glu Pro Gly Lys Tyr Thr Ala Thr Gly Gly Ser His
 65                  70                  75                  80

Val Ala Tyr Ile Ile Arg Ser His Val Lys Asp His Tyr Ile Phe Tyr
                 85                  90                  95

Ser Glu Gly Lys Leu Gln Gly Glu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 29
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the light chain of
      antibody 31H4
<220> FEATURE:
<221> NAME/KEY: SIGNAL
<222> LOCATION: (1)..(20)

<400> SEQUENCE: 29

Met Val Leu Gln Thr Gln Val Phe Ile Ser Leu Leu Trp Ile Ser
  1               5                  10                  15

Gly Ala Tyr Gly Glu Ser Val Leu Thr Gln Pro Ser Val Ser Gly
             20                  25                  30

Ala Pro Gly Gln Arg Val Thr Ile Ser Cys Thr Gly Ser Ser Ser Asn
         35                  40                  45

Ile Gly Ala Gly Tyr Asp Val His Trp Tyr Gln Gln Leu Pro Gly Thr
     50                  55                  60

Ala Pro Lys Leu Leu Ile Ser Gly Asn Ser Asn Arg Pro Ser Gly Val
 65                  70                  75                  80

Pro Asp Arg Phe Ser Gly Ser Lys Ser Gly Thr Ser Ala Ser Leu Ala
                 85                  90                  95

Ile Thr Gly Leu Gln Ala Glu Asp Glu Ala Asp Tyr Tyr Cys Gln Ser
            100                 105                 110

Tyr Asp Ser Ser Leu Ser Gly Ser Val Phe Gly Gly Gly Thr Lys Leu
        115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235
```

```
<210> SEQ ID NO 30
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variant of mutein shown in SEQ ID NO: 22

<400> SEQUENCE: 30

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Trp Gly Arg Ser Gln Glu Val Lys Ala Val Leu
50                  55                  60

Glu Arg Thr Asp Glu Pro Gly Lys Tyr Thr Ala Gln Gly Asp Arg His
65                  70                  75                  80

Val Ala Tyr Ile Ile Arg Ser His Val Lys Asp His Tyr Ile Phe Tyr
                85                  90                  95

Ser Glu Gly Asn Leu Gln Gly Glu Thr Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 31
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variant of mutein shown in SEQ ID NO: 13

<400> SEQUENCE: 31

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
50                  55                  60

Glu Arg Thr Asp Glu Pro Gly Lys Tyr Thr Thr Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro His Gln Gly Ala Pro Val Pro Gly Val Trp Leu Val
            100                 105                 110

Gly Arg Asp Pro Lys Asn Asn Leu Glu Ala Leu Glu Asp Phe Glu Lys
```

```
                115                 120                 125
Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 32
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variant of mutein shown in SEQ ID NO: 20

<400> SEQUENCE: 32

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Lys Thr Asp Glu Pro Gly Lys Tyr Thr Val Met Gly Gly Ser His
65              70                  75                  80

Val Ala Ser Ile Ile Arg Ser His Val Lys Asp His Tyr Ile Phe Tyr
                85                  90                  95

Pro Glu Gly Pro Tyr Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 33
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the heavy chain of
      antibody 31H4
<220> FEATURE:
<221> NAME/KEY: SIGNAL
<222> LOCATION: (1)..(19)

<400> SEQUENCE: 33

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60
```

```
Glu Trp Val Ser Ser Ile Ser Ser Ser Ser Tyr Ile Ser Tyr Ala
65              70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Phe Cys Ala Arg Asp Tyr Asp Phe Trp Ser Ala Tyr Tyr Asp Ala
            115                 120                 125

Phe Asp Val Trp Gly Gln Gly Thr Met Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys
465                 470
```

```
<210> SEQ ID NO 34
<211> LENGTH: 692
<212> TYPE: PRT
<213> ORGANISM: Homo sapiens
<220> FEATURE:
<223> OTHER INFORMATION: Full-length human proprotein convertase
      subtilisin/kexin type 9 (PCSK9) according to SWISS PROT Data Bank
      Accession NO: Q8NBP7

<400> SEQUENCE: 34

Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
             20                  25                  30

Asp Glu Asp Gly Asp Tyr Glu Glu Leu Val Leu Ala Leu Arg Ser Glu
         35                  40                  45

Glu Asp Gly Leu Ala Glu Ala Pro Glu His Gly Thr Thr Ala Thr Phe
     50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
```

```
                355                 360                 365
Ile Gly Ala Ser Ser Asp Cys Ser Thr Cys Phe Val Ser Gln Ser Gly
    370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
            420                 425                 430
Gln Arg Val Leu Thr Pro Asn Leu Val Ala Ala Leu Pro Pro Ser Thr
                435                 440                 445
His Gly Ala Gly Trp Gln Leu Phe Cys Arg Thr Val Trp Ser Ala His
            450                 455                 460
Ser Gly Pro Thr Arg Met Ala Thr Ala Ile Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
                500                 505                 510
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
            595                 600                 605
Lys Val Lys Glu His Gly Ile Pro Ala Pro Gln Glu Gln Val Thr Val
            610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Glu Ala Val
            660                 665                 670
Thr Ala Val Ala Ile Cys Cys Arg Ser Arg His Leu Ala Gln Ala Ser
            675                 680                 685
Gln Glu Leu Gln
    690

<210> SEQ ID NO 35
<211> LENGTH: 580
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Plasmid pTLPC26 (XbaI-HindIII)

<400> SEQUENCE: 35
tctagataac gagggcaaaa aatgaaaaag acagctatcg cgattgcagt ggctctggct      60
```

```
ggcttcgcta ccgtagcgca ggccgcctca gacgaggaga ttcaggatgt gtcagggacg      120
tggtatctga aggccatgac ggtggacagg gagttccctg agatgaatct ggaatcggtg      180
acacccatga ccctcacgac cctggaaggg ggcaacctgg aagccaaggt caccatgctg      240
ataagtggcc ggagccagga ggtgaaggcc gtcctggaga aaactgacga gccgggaaaa      300
tacacggccg acggggggcaa gcacgtggca tacatcatca ggtcgcacgt gaaggaccac      360
tacatctttt actctgaggg cgagctccac gggaagccgg tcccagggg gtggctcgtg       420 ggcagagacc ccaagaacaa cctggaagcc ttggaggact ttgagaaagc cgcaggagcc      480
cgcggactca gcacggagag catcctcatc cccaggcaga gcgaaaccag ctctccaggg      540
agcgcttggt ctcacccgca gttcgaaaaa taataagctt                            580
```

<210> SEQ ID NO 36
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 3

<400> SEQUENCE: 36

```
gcctcagacg aggagattca ggatgtgtca gggacgtggt atctgaaggc catgacggtg       60
gacttcagcc gcggggacgc gatatggacg agcgtaacac cgatgaccct gactacactg      120
gagggcggca acctggaggc gaaggtcacc atgatgtatg ccggccgcag ccaggaagtc      180
aaagcggttt tagaaaagac cgacgaaccg ggcaaataca ccgcgatggg tggcagccat      240
gtggcgtaca tcattcgtag ccatgttaaa gatcactata tcttttattc cgaaggtccg      300
tatcagggcg cgccggtgcc aggggtgtgg ctcgtgggca gagaccccaa gaacaacctg      360
gaagccttgg aggactttga gaagccgcag gagcccgcg gactcagcac ggagagcatc      420
ctcatcccca ggcagagcga aaccagctct ccaggg                                 456
```

<210> SEQ ID NO 37
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 4

<400> SEQUENCE: 37

```
gcctcagacg aggagattca ggatgtgtca gggacgtggt atctgaaggc catgacggtg       60
gattggcaat gtgatactgg gctgtggact tctgttacgc caatgactct gactacccTT      120
gaaggcggca atctggaggc taaggtcacc atgtcttacg caggggcatt tcaggaggtg      180
aaagcagtgt tagagaagac agatgaaccg gtaaatata cggccgatgg cggtaaacat      240
gttgcctata tcattcgcag ccatgtgaaa gatcattaca tcttttatag cgagggcgag      300 tgtgggggt ggcctgttcc aggggtgtgg ctcgtgggca gagaccccaa gaacaacctg       360
gaagccttgg aggactttga gaagccgca ggagcccgcg gactcagcac ggagagcatc      420
ctcatcccca ggcagagcga aaccagctct ccaggg                                 456
```

<210> SEQ ID NO 38

```
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 5

<400> SEQUENCE: 38
gcctcagacg aggagattca ggatgtgtca gggacgtggt atctgaaggc catgacggtg     60
gaccacgaat ggaacggcca ttactatacg agcgtaacac cgatgaccct gactacactg    120
gagggcggca acctggaggc gaaggtcacc atgtcttatc gcggccgcag ccaggaagtc    180
aaagcggttt tagaaaagac cgacgaaccg ggcaaataca ccgcgccggg tggccaacat    240
gtggcgtaca tcattcgtag ccatgttaaa gatcactata tctttttattc cgaaggttct    300 tggccgggct atccggtgcc aggggtgtgg ctcgtgggca gagaccccaa gaacaacctg    360
gaagccttgg aggactttga gaagccgca ggagcccgcg gactcagcac ggagagcatc     420
ctcatcccca ggcagagcga aaccagctct ccaggg                              456

<210> SEQ ID NO 39
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 6

<400> SEQUENCE: 39
gcctcagacg aggagattca ggatgtgtca gggacgtggt atctgaaggc catgacggtg     60
gacttcaccg acaactctcc catgtttacg agcgtaacac cgatgaccct gactacactg    120
gagggcggca acctggaggc gaaggtcacc atgcagtatg ccggccgcag ccaggaagtc    180
aaagcggttt tagaaaagac cgacgaaccg ggcaaataca ccgcgatagg tggcacccat    240
gtggcgtaca tcattcgtag ccatgttaaa gatcactata tctttttattc cgaaggtgcc    300 gaacgcggcc gtccggtgcc aggggtgtgg ctcgtgggca gagaccccaa gaacaacctg    360
gaagccttgg aggactttga gaagccgca ggagcccgcg gactcagcac ggagagcatc     420
ctcatcccca ggcagagcga aaccagctct ccaggg                              456

<210> SEQ ID NO 40
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 7

<400> SEQUENCE: 40
gcctcagacg aggagattca ggatgtgtca gggacgtggt atctgaaggc catgacggtg     60
gaccgcttta aaatcgccag ctggccccgc agcgtaacac cgatgaccct gactacactg    120
gagggcggca acctggaggc gaaggtcacc atgaattggt ggggccgcag ccaggaagtc    180
aaagcggttt tagaaaagac cgacgaaccg ggcaaataca ccgcgcaggg tggcagccat    240
gtggcgtaca tcattcgtag ccatgttaaa gatcactata tctttttattc cgaaggtaat    300
```

```
cgtcagggcg atccggtgcc aggggtgtgg ctcgtgggca gagaccccaa gaacaacctg      360
gaagccttgg aggactttga gaaagccgca ggagcccgcg gactcagcac ggagagcatc      420
ctcatcccca ggcagagcga aaccagctct ccaggg                                 456

<210> SEQ ID NO 41
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 8

<400> SEQUENCE: 41
gcctcagacg aggagattca ggatgtgtca gggacgtggt atctgaaggc catgacggtg      60
gacttcaagg gccccacgcc cctctggacg agcgtaacac cgatgaccct gactacactg     120
gagggcggca acctggaggc gaaggtcacc atgttccatg ccggccgcag ccaggaagtc     180
aaagcggttt tagaaaagac cgacgaaccg ggcaaataca ccgcgtacgg tggccgtcat     240
gtggcgtaca tcattcgtag ccatgttaaa gatcactata tcttttattc cgaaggtgcc     300
agcgtgggca acccggtgcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                                 456

<210> SEQ ID NO 42
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 9

<400> SEQUENCE: 42
gcctcagacg aggagattca ggatgtgtca gggacgtggt atctgaaggc catgacggtg      60
gacacggaac acttagccga ttgggcgaat agcgtaacac cgatgaccct gactacactg     120
gagggcggca acctggaggc gaaggtcacc atgcaccaac cggccgcag ccaggaagtc      180 aaagcggttt tagaaaagac cgacgaaccg ggcaaataca ccgcgatagg tggcagccat     240
gtggcgtaca tcattcgtag ccatgttaaa gatcactata tcttttattc cgaaggtgcc     300
tatccgggca gcccggtgcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                                 456

<210> SEQ ID NO 43
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 10

<400> SEQUENCE: 43
gcctcagacg aggagattca ggatgtgtca gggacgtggt atctgaaggc catgacggtg      60
```

```
gaccgcgcgg acatgggcga ttggcccaat agcgtaacac cgatgaccct gactacactg     120
gagggcggca acctggaggc gaaggtcacc atgttcaccc gcggccgcag ccaggaagtc     180
aaagcggttt tagaaaagac cgacgaaccg ggcaaataca ccgcgacggg tggcgaacat     240
gtggcgtaca tcattcgtag ccatgttaaa gatcactata tcttttattc cgaaggtacg     300
ttaacaggcc gtccggtgcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                                456

<210> SEQ ID NO 44
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 11

<400> SEQUENCE: 44
gcctcagacg aggagattca ggatgtgtca gggacgtggt atctgaaggc catgacggtg     60
gactggcgtc tcgataatga actctggacg agcgtaacac cgatgaccct gactacactg    120
gagggcggca acctggaggc gaaggtcacc atgatgtatg ccggccgcag ccaggaagtc    180
aaagcggttt tagaaaagac cgacgaaccg ggcaaataca ccgcgcaggg tggcagccat    240
gtggcgtaca tcattcgtag ccatgttaaa gatcactata tcttttattc cgaaggtccg    300
cgtaatggcg cgccggtgcc aggggtgtgg ctcgtgggca gagaccccaa gaacaacctg    360
gaagccttgg aggactttga gaaagccgca ggagcccgcg gactcagcac ggagagcatc    420
ctcatcccca ggcagagcga aaccagctct ccaggg                                456

<210> SEQ ID NO 45
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 12

<400> SEQUENCE: 45
gcctcagacg aggagattca ggatgtgtca gggacgtggt atctgaaggc catgactttg     60
gattggcaat gtgatactgg gctgtggact tctgttacgc caatgactct gactacccct    120
gaaggcggca atctggaggc taaggtcacc atgtcttacg cagggcatt tcaggaggtg    180 aaagcagtgt tagagaagac agatgaaccg ggtaaatata cggccgatgg cggtaaacat    240
gttgcctata tcattcgcag ccatgtgaaa gatcattaca tcttttatag cgagggcgag    300 tgtgggggt ggcctgttcc aggggtgtgg ctcgtgggca gagaccccaa gaacaacctg    360
gaagccttgg aggactttga gaaagccgca ggagcccgcg gactcagcac ggagagcatc    420
ctcatcccca ggcagagcga aaccagctct ccaggg                                456

<210> SEQ ID NO 46
<211> LENGTH: 456
<212> TYPE: DNA
<213> ORGANISM: Artificial Sequence
<220> FEATURE:
<223> OTHER INFORMATION: Description of Artificial Sequence: Synthetic
``` polynucleotide
<220> FEATURE:
<223> OTHER INFORMATION: DNA sequence of mutein shown in SEQ ID NO: 13

<400> SEQUENCE: 46

```
gcctcagacg aggagattca ggatgtgtca gggacgtggt atctgaaggc catgacggtg      60
gacttcagcc gcggggacgc gatatggacg agcgtaacac cgatgaccct gactacactg     120
gagggcggca acctggaggc gaaggtcacc atgatgtatg ccggccgcag ccaggaagtc     180
aaagcggttt tagaaaggac cgacgaaccg ggcaaataca ccacgatggg tggcagccat     240
gtggcgtaca tcatccgtag ccctgtcaaa gatcactata tcttttattc cgaaggcccg     300
catcagggcg cgccggtgcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                               456
```

<210> SEQ ID NO 47
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 14

<400> SEQUENCE: 47

```
gcctcagacg aggagattca ggatgtgtca gggacgtggt atctgaaggc catgacggtg      60
gacttcagcc gcggggacgc gatatggacg agcgtaacac cgatgaccct gactacactg     120
gagggcggca acctggaggc gaaggtcacc atgatgtatg ccggccgcag ccaggaagtc     180
aaagcggtct tagaaaagac cgacgaaccg ggcaaataca ccgcgatggg tggcagccat     240
gtggcgtaca tcactcgtag ccatgttaaa gatcactata tcttttattc cgaaggtccg     300
catcagggcg cgccggtgcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                               456
```

<210> SEQ ID NO 48
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 15

<400> SEQUENCE: 48

```
gcctcagacg aggagattca ggatgtgtca gggacgtggt atctgaaggc catgacggtg      60
gacttcagcc gcggggacgc gatatggact agcgtaacac cgatgaccct gactatactg     120
gagggcggca acctggaggc gaaggtcacc atgatgtatg ccggccgcag ccagggagtc     180
aaagtggttt tagaaaagac cgacgaaccg ggcaaataca ccgcgatggg tggcagccaa     240
gtggcgtaca tcattcgtag ccatgttaaa gatcactata tcttttatcc cgaaggtccg     300
tatcagggcg cgccggtgcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                               456
```

<210> SEQ ID NO 49
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 16

<400> SEQUENCE: 49

```
gcctcagacg aggagattca ggatgtgtca gggacgtggt atctgaaggc catgacggtg      60
gacttcagcc gcggggacgc gatatggacg agcgttacgc caatgactct gactacccttt    120 gaaggcggca atctggaggc taaggtcacc atgatgtatg ccggccgcag ccaggaagtc     180
aaagcggttt tagaaaagac cgacgaaccg ggcaaataca ccacgatggg tggcagccat     240
gtggcgtaca tcattcgtag ccacgttaaa gatcactata tcttttattc cgaaggcccg     300
tatcagggcg cgccggttcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                              456
```

<210> SEQ ID NO 50
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 17

<400> SEQUENCE: 50

```
gcctcagacg aggagattca ggatgtgtca gggacgtggt atctgaaggc catgacggtg      60
gacttttcga gggggatgc gatttggacg agcgtaacac cgatgaccct gactacactg      120
gagggcggca acctggaggc gaaggtcacc atgatgtatg ctggccggag ccaggaggtg     180
aaagcggttt tagaaaagac cgacgaaccg ggcaaataca ccgccagtgg gggctctcat     240
gtggcgtaca tcattcgtag ccatgttaaa gatcactata tcttttattc cgaaggtcct     300 catcagggggg ctccggtgcc aggggtgtgg ctcgtgggca gagaccccaa gaacaacctg    360
gaagccttgg aggactttga gaaagccgca ggagcccgcg gactcagcac ggagagcatc     420
ctcatcccca ggcagagcga aaccagctct ccaggg                              456
```

<210> SEQ ID NO 51
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 18

<400> SEQUENCE: 51

```
gcctcagacg aggagattca ggatgtgtca gggacgtggt atctgaaggc catgacggtg      60
gacttcagcc gcggggacgc gatatggacg agcgtaacac cgatgaccct gactgcactg     120
gagggcggcg gcctggaggc gaaggtcacc atgatgtatg ccggccgcag ccaggaagtc     180
aaagtggttt tagaaaagac cgacgaaccg ggcaaataca ccgcgatggg tggcagccat     240
```

```
ggggcgtaca tcactcgtag ccatgttaaa gatcactata tcttttattc cgaaggtccg    300
tatcggggcg cgccggtgcc aggggtgtgg ctcgtgggga gagacccccaa gaacaacctg   360 gaagccttgg aggactttga gaaagccgca ggagcccgcg gactcagcac ggagagcatc    420
ctcatcccca ggcagagcga aaccagctct ccaggg                              456
```

<210> SEQ ID NO 52
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 19

<400> SEQUENCE: 52

```
gcctcagacg aggagattca ggatgtgtca gggacgtggt atctgaaggc catgacggtg    60
gacttcagcc gcggggacgc gatatggacg agcgtaacac cgatgaccct gactacactg    120
gagggcggca acatggaggc gaaggtcacc atgatgtatg ccggccgcag ccaggaagtc    180
aaagcggttt tagaaaagac cgacgaaccg ggcaaataca ccgcgatggg tggcagccat    240
gtggcgtaca tcattcgtag ccatgttaaa gatcactata tcttttattc cgaaggtctg    300
tatcagggcg cgccggtgcc aggggtgtgg ctcgtgggga gacccccaa gaacaacctg    360 gaagccttgg aggactttga gaaagccgca ggagcccgcg gactcagcac ggagagcatc    420
ctcatcccca ggcagagcga aaccagctct ccaggg                              456
```

<210> SEQ ID NO 53
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 20

<400> SEQUENCE: 53

```
gcctcagacg aggagattca ggatgtgtca gggacgtggt atctgaaggc catgacggtg    60
gacttcagcc gcggggacgc gatatggacg agcgtaacac cgatgaccct gactacactg    120
gagggcggca acctggaggc gaaggtcacc atgatgtatg ccggccgcag ccaggaagtc    180
aaagcggttt tagaaaagac cgacgagccg ggcaaataca ccgtgatggg aggtagccat    240
gtggcgtcca tcattcgtag ccatgttaag gatcactata tcttttaccc cgaaggtccg    300
tatcagggcg cgccggtgcc aggggtgtgg ctcgtgggca gacccccaa gaacaacctg    360 gaagccttgg aggactttga gaaagccgca ggagcccgcg gactcagcac ggagagcatc    420
ctcatcccca ggcagagcga aaccagctct ccaggg                              456
```

<210> SEQ ID NO 54
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 21

<400> SEQUENCE: 54

```
gcctcagacg aggagattca ggatgtgtca gggacgtggt atctgaaggc catgacggtg    60
gacttcagcc gcggggacgc gatatggacg agcgtaacgc cgatgaccct gactacactg   120
gagggcggta acctggaggc gaaggtcacc atgatgtatg ccggccgcag tcaggaagtc   180
aaagcggttt tagaaaagac cgacgagccg ggcaaataca ccgcaatggg tggcagccat   240
gtggcgtaca tccttcgtag ccatgttaaa gatcactata tcttttattc cgaaggtccg   300
catcagggcg cgccggtgcc aggggtgtgg ctcgtgggca gagacccaa  gaacaacctg   360 gaagccttgg aggactttga gaaagccgca ggagcccgcg gactcagcac ggagagcatc   420
ctcatcccca ggcagagcga aaccagctct ccaggg                             456
```

<210> SEQ ID NO 55
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 22

<400> SEQUENCE: 55

```
gcctcagacg aggagattca ggatgtgtca gggacgtggt atctgaaggc catgacggtg    60
gaccgcttta aaatcgccag ctggccccgc agcgtaactc cgatgaccct gactacactg   120
gagggcggca acctggaggc gaaggtcacc atgaattggt ggggccgcag ccaggaagtc   180
aaagcggttt tagaaaggac cgacgaaccg ggcaaataca ccgcgcaggg tgaccgccat   240
gtggcgtaca tcattcgtag ccatgttaaa gatcactata tcttttattc cgaaggtaat   300
cttcagggcg aaacggtccc aggggtgtgg ctcgtgggca gagacccaa  gaacaacctg   360 gaagccttgg aggactttga gaaagccgca ggagcccgcg gactcagcac ggagagcatc   420
ctcatcccca ggcagagcga aaccagctct ccaggg                             456
```

<210> SEQ ID NO 56
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 23

<400> SEQUENCE: 56

```
gcctcagacg aggagattca ggatgtgtca gggacgtggt atctgaaggc catgacggtg    60
gaccgcttta aaatcgccag ctggccccgc agcgtaacac cgatgaccct gactacactg   120
gggggcggca acctggaggc gaaggtcacc atgaattggt ggggccgcag ccaggaagtc   180
aaagctgttt tagaaaagac cgacgaaccg ggcaaataca ccgcgcaggg tggtagccat   240
gtggagcata tcattcgtag ccatgttaaa gatcactata tcttttattc caaaggtaat   300
cttcagggcg aaccggtccc aggggtgtgg ctcgtgggca gagacccaa  gaacaacctg   360 gaagccttgg aggactttga gaaagccgca ggagcccgcg gactcagcac ggagagcatc   420
ctcatcccca ggcagagcga aaccagctct ccaggg                             456
```

<210> SEQ ID NO 57
<211> LENGTH: 456
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 24

<400> SEQUENCE: 57
gcctcagacg aggagattca ggatgtgtca gggacgtggt atctgaaggc catgacggtg      60
gaccgcttta aaatcgccag ctggccccgc agcgtaacac cgatgaccct gactacactg     120
gagggcggca acctggaggc gaaggtcacc atgaattggt ggggccgcag ccaggaagtc     180
aaagcggttt tagaaaagac cgacgaaccg ggcaaataca ccgcgcaggg tggcagccat     240
gtggagtaca tcattcgtag ccatgttaaa gatcactata tcttttattc cgaaggtaat     300
cttcagggcg aaccggtccc aggggtgtgg ctcgtgggca gagacccaa gaacaacctg      360 gaagccttgg aggactttga gaaagccgca ggagcccgcg gactcagcac ggagagcatc     420
ctcatcccca ggcagagcga aaccagctct ccaggg                              456

<210> SEQ ID NO 58
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 25

<400> SEQUENCE: 58
gcctcagacg aggagattca ggatgtgtca gggacgtggt atctgaaggc catgacggtg      60
gaccgcttta aaatcgccag ctggccccgc agcgtaacac cgatgaccct gacaacactg     120
gagggcggca acctggaggc gaaggtcacc atgaattggt ggggccgcag ccaggatgtc     180
aaagcggttt taggaaagac cgacgaaccg ggcaaataca ccgcgcaggg tgacagccat     240
gtgtcgtaca tcattcgtag ccatgttaaa gatcactata tcttttattc cgtaggtaat     300
cttcagggcg aaacggtccc aggggtgtgg ctcgtgggca gagacccaa gaacaacctg      360 gaagccttgg aggactttga gaaagccgca ggagcccgcg gactcagcac ggagagcatc     420
ctcatcccca ggcagagcga aaccagctct ccaggg                              456

<210> SEQ ID NO 59
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 26

<400> SEQUENCE: 59
gcctcagacg aggagattca ggatgtgtca gggacgtggt atctgaaggc catgacggtg      60
gacaggttta agattgcttc gtggcctagg agcgtaacac cgatgaccct gactacactg     120
gagggcggca acctggaggc gaaggtcacc atgaattggt ggggccggag ccaggaggtg     180
aaagcggttt tagaaaagac cgacgaaccg ggcaaataca ccgccgtggg gggctctcat     240
gtggcgtaca tcattcgtag ccatgttaaa gatcactata tcttttattc cgaaggtaag     300 ttgcagggggg agccggtgcc aggggtgtgg ctcgtgggca gagacccaa gaacaacctg     360
```
gaagccttgg aggactttga aaagccgca ggagcccgcg gactcagcac ggagagcatc    420
ctcatcccca ggcagagcga aaccagctct ccaggg                             456

<210> SEQ ID NO 60
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 27

<400> SEQUENCE: 60
gcctcagacg aggagattca ggatgtgtca gggacgtggt atctgaaggc catgacggtg    60
gacaggttta agattgggtc gtggcctagg agcgtaacac cgatgaccct gactacactg   120
gagggcggca acctggaggc gaaggtcacc atgaattggc ggggccggag ccaggaggtg   180
aaagcggttt tagaaaagac cgacgaaccg ggcaaataca ccgcccaggg gggctctcat   240
gtggcgtaca tcattcgtag ccatgttaaa gatcactata tcttttattc cgaaggtaag   300
ctgcaggggg agccggtgcc aggggtgtgg ctcgtgggca gagacccaa gaacaacctg    360 gaagccttgg aggactttga aaagccgca ggagcccgcg gactcagcac ggagagcatc    420
ctcatcccca ggcagagcga aaccagctct ccaggg                             456

<210> SEQ ID NO 61
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 28

<400> SEQUENCE: 61
gcctcagacg aggagattca ggatgtgtca gggacgtggt atctgaaggc catgacggtg    60
gacaggttta agattggtgc gtggccgagg agcgtaacac cgatgaccct gactacactg   120
gagggcggca acctggaggc gaaggtcacc atgaattggt ggggccggag ccaggaggtg   180
aaagcggttt tagaaaagac cgacgaaccg ggcaaataca ccgccacggg gggctctcat   240
gtggcgtaca tcattcgtag ccatgttaaa gatcactata tcttttattc cgaaggtaag   300
ttgcaggggg agccggtgcc aggggtgtgg ctcgtgggca gagacccaa gaacaacctg    360 gaagccttgg aggactttga aaagccgca ggagcccgcg gactcagcac ggagagcatc    420
ctcatcccca ggcagagcga aaccagctct ccaggg                             456

<210> SEQ ID NO 62
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 62

Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val

Thr Pro Met Thr Leu Thr Thr Leu Glu Gly Gly Asn Leu Glu Ala Lys
            20                  25                  30
                35                  40                  45

Val Thr Met Asn Trp Trp Gly Arg Ser Gln Glu Val Lys Ala Val Leu
            50                  55                  60

Glu Arg Thr Asp Glu Pro Gly Lys Tyr Thr Ala Gln Gly Asp Arg His
65                  70                  75                  80

Val Ala Tyr Ile Ile Arg Ser Pro Val Lys Asp His Tyr Ile Phe Tyr
                85                  90                  95

Ser Glu Gly Asn Leu Gln Gly Glu Thr Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 63
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 63

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
                35                  40                  45

Val Thr Met Met Tyr Ala Gly Arg Ser Gln Glu Val Lys Ala Val Leu
            50                  55                  60

Glu Arg Thr Asp Glu Pro Gly Lys Tyr Thr Val Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Gly Gln Gly Ala Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 64
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 64

```
Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
50                  55                  60

Glu Arg Thr Asp Glu Pro Gly Lys Tyr Thr Val Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Arg Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150
```

<210> SEQ ID NO 65
<211> LENGTH: 152
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Mutein of human tear lipocalin

<400> SEQUENCE: 65

```
Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
50                  55                  60

Glu Arg Thr Asp Glu Pro Gly Lys Tyr Thr Thr Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Ala Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150
```

<210> SEQ ID NO 66
<211> LENGTH: 152

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 66

```
Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Arg Thr Asp Glu Pro Gly Lys Tyr Thr Val Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Asp Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 67
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 67

```
Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Arg Thr Asp Glu Pro Gly Lys Tyr Thr Met Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Val Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140
```

```
Gln Ser Glu Thr Ser Ser Pro Gly
145                 150

<210> SEQ ID NO 68
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 68

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Arg Thr Asp Glu Pro Gly Lys Tyr Thr Val Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Pro Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 69
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 69

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Arg Thr Asp Glu Pro Gly Lys Tyr Thr Val Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Lys Gln Gly Ala Pro Val Pro Gly Val Trp Leu Val
```

```
                    100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 70
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 70

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60

Glu Arg Thr Asp Glu Pro Gly Lys Tyr Thr Thr Met Gly Gly Ser His
65                  70                  75                  80

Val Ala Tyr Ile Ile Arg Ser Pro Val Lys Asp His Tyr Ile Phe Tyr
                85                  90                  95

Ser Glu Gly Pro Arg Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 71
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 71

Ala Ser Asp Glu Glu Ile Gln Asp Val Ser Gly Thr Trp Tyr Leu Lys
1               5                   10                  15

Ala Met Thr Val Asp Phe Ser Arg Gly Asp Ala Ile Trp Thr Ser Val
            20                  25                  30

Thr Pro Met Thr Leu Thr Thr Leu Glu Gly Gly Asn Leu Glu Ala Lys
        35                  40                  45

Val Thr Met Met Tyr Ala Gly Arg Ser Gln Glu Val Lys Ala Val Leu
    50                  55                  60
```

Glu Arg Thr Asp Glu Pro Gly Lys Tyr Thr Val Met Gly Gly Ser His
 65                  70                  75                  80

Val Ala Tyr Ile Ile Arg Ser Pro Val Lys Asp His Tyr Ile Phe Tyr
                 85                  90                  95

Ser Glu Gly Pro Leu Gln Gly Ala Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 72
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 62

<400> SEQUENCE: 72
gcctcagacg aggagattca ggatgtgtca gggacgtggt atctgaaggc catgacggtg      60
gaccgcttta aaatcgccag ctggccccgc agcgtaactc cgatgaccct gactacactg     120
gagggcggca acctggaggc gaaggtcacc atgaattggt ggggccgcag ccaggaagtc     180
aaagcggttt tagaaaggac cgacgaaccg ggcaaataca ccgcgcaggg tgaccgccat     240
gtggcgtaca tcattcgtag cccggttaaa gatcactata tctttttattc cgaaggtaat     300 cttcagggcg aaacggtccc aggggtgtgg ctcgtgggca gagaccccaa gaacaacctg     360
gaagccttgg aggactttga aaagccgca ggagcccgcg gactcagcac ggagagcatc     420
ctcatcccca ggcagagcga aaccagctct ccaggg                               456

<210> SEQ ID NO 73
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 63

<400> SEQUENCE: 73
gcctcagacg aggagattca ggatgtgtca gggacgtggt atctgaaggc catgacggtg      60
gacttcagcc gcggggacgc gatatggacg agcgtaacac cgatgaccct gactacactg     120
gagggcggca acctggaggc gaaggtcacc atgatgtatg ccggccgcag ccaggaagtc     180
aaagcggttt tagaaaggac cgacgaaccg ggcaaataca ccgttatggg tggcagccat     240
gtggcgtaca tcatccgtag ccctgtcaaa gatcactata tctttttattc cgaaggcccg     300 ggcagggcg cgccggtgcc aggggtgtgg ctcgtgggca gagaccccaa gaacaacctg     360
gaagccttgg aggactttga aaagccgca ggagcccgcg gactcagcac ggagagcatc     420
ctcatcccca ggcagagcga aaccagctct ccaggg                               456

<210> SEQ ID NO 74
<211> LENGTH: 456

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 64

<400> SEQUENCE: 74
gcctcagacg aggagattca ggatgtgtca gggacgtggt atctgaaggc catgacggtg      60
gacttcagcc gcggggacgc gatatggacg agcgtaacac cgatgaccct gactacactg     120
gagggcggca acctggaggc gaaggtcacc atgatgtatg ccggccgcag ccaggaagtc     180
aaagcggttt tagaaaggac cgacgaaccg ggcaaataca ccgtgatggg tggcagccat     240
gtggcgtaca tcatccgtag ccctgtcaaa gatcactata tcttttattc cgaaggcccg     300
cgtcagggcg cgccggtgcc aggggtgtgg ctcgtgggca gagaccccaa gaacaacctg     360
gaagccttgg aggactttga gaaagccgca ggagcccgcg gactcagcac ggagagcatc     420
ctcatccccg gcagagcgaa accagctct ccaggg                                456

<210> SEQ ID NO 75
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 65

<400> SEQUENCE: 75
gcctcagacg aggagattca ggatgtgtca gggacgtggt atctgaaggc catgacggtg      60
gacttcagcc gcggggacgc gatatggacg agcgtaacac cgatgaccct gactacactg     120
gagggcggca acctggaggc gaaggtcacc atgatgtatg ccggccgcag ccaggaagtc     180
aaagcggttt tagaaaggac cgacgaaccg ggcaaataca ccgtgatggg tggcagccat     240
gtggcgtaca tcatccgtag ccctgtcaaa gatcactata tcttttattc cgaaggcccg     300
gctcagggcg cgccggtgcc aggggtgtgg ctcgtgggca gagaccccaa gaacaacctg     360
gaagccttgg aggactttga gaaagccgca ggagcccgcg gactcagcac ggagagcatc     420
ctcatccccg gcagagcgaa accagctct ccaggg                                456

<210> SEQ ID NO 76
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 66

<400> SEQUENCE: 76
gcctcagacg aggagattca ggatgtgtca gggacgtggt atctgaaggc catgacggtg      60
gacttcagcc gcggggacgc gatatggacg agcgtaacac cgatgaccct gactacactg     120
gagggcggca acctggaggc gaaggtcacc atgatgtatg ccggccgcag ccaggaagtc     180
aaagcggttt tagaaaggac cgacgaaccg ggcaaataca ccatgatggg tggcagccat     240
gtggcgtaca tcatccgtag ccctgtcaaa gatcactata tcttttattc cgaaggcccg     300
gatcagggcg cgccggtgcc aggggtgtgg ctcgtgggca gagaccccaa gaacaacctg     360
```

```
gaagccttgg aggactttga gaaagccgca ggagcccgcg gactcagcac ggagagcatc    420
ctcatcccca ggcagagcga aaccagctct ccaggg                              456

<210> SEQ ID NO 77
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 67

<400> SEQUENCE: 77
gcctcagacg aggagattca ggatgtgtca gggacgtggt atctgaaggc catgacggtg    60
gacttcagcc gcggggacgc gatatggacg agcgtaacac cgatgaccct gactacactg    120
gagggcggca acctggaggc gaaggtcacc atgatgtatg ccggccgcag ccaggaagtc    180
aaagcggttt tagaaaggac cgacgaaccg ggcaaataca ccatgatggg tggcagccat    240
gtggcgtaca tcatccgtag ccctgtcaaa gatcactata tcttttattc cgaaggcccg    300
gttcagggcg cgccggtgcc aggggtgtgg ctcgtgggca gagacccaa gaacaacctg    360 gaagccttgg aggactttga gaaagccgca ggagcccgcg gactcagcac ggagagcatc    420
ctcatcccca ggcagagcga aaccagctct ccaggg                              456

<210> SEQ ID NO 78
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 68

<400> SEQUENCE: 78
gcctcagacg aggagattca ggatgtgtca gggacgtggt atctgaaggc catgacggtg    60
gacttcagcc gcggggacgc gatatggacg agcgtaacac cgatgaccct gactacactg    120
gagggcggca acctggaggc gaaggtcacc atgatgtatg ccggccgcag ccaggaagtc    180
aaagcggttt tagaaaggac cgacgaaccg ggcaaataca ccatgatggg tggcagccat    240
gtggcgtaca tcatccgtag ccctgtcaaa gatcactata tcttttattc cgaaggcccg    300
ccgcagggcg cgccggtgcc aggggtgtgg ctcgtgggca gagacccaa gaacaacctg    360 gaagccttgg aggactttga gaaagccgca ggagcccgcg gactcagcac ggagagcatc    420
ctcatcccca ggcagagcga aaccagctct ccaggg                              456

<210> SEQ ID NO 79
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 69

<400> SEQUENCE: 79
gcctcagacg aggagattca ggatgtgtca gggacgtggt atctgaaggc catgacggtg    60
gacttcagcc gcggggacgc gatatggacg agcgtaacac cgatgaccct gactacactg    120
```

```
gagggcggca acctggaggc aaggtcacc atgatgtatg ccggccgcag ccaggaagtc    180
aaagcggttt tagaaaggac cgacgaaccg ggcaaataca ccgttatggg tggcagccat    240
gtggcgtaca tcatccgtag ccctgtcaaa gatcactata tcttttattc cgaaggcccg    300
aagcagggcg cgccggtgcc aggggtgtgg ctcgtgggca gaaccccaa gaacaacctg    360 gaagccttgg aggactttga gaaagccgca ggagcccgcg gactcagcac ggagagcatc    420
ctcatcccca ggcagagcga aaccagctct ccaggg                              456

<210> SEQ ID NO 80
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 70

<400> SEQUENCE: 80
gcctcagacg aggagattca ggatgtgtca gggacgtggt atctgaaggc catgacggtg     60
gacttcagcc gcggggacgc gatatggacg agcgtaacac cgatgaccct gactacactg    120
gagggcggca acctggaggc gaaggtcacc atgatgtatg ccggccgcag ccaggaagtc    180
aaagcggttt tagaaaggac cgacgaaccg ggcaaataca ccgtgatggg tggcagccat    240
gtggcgtaca tcatccgtag ccctgtcaaa gatcactata tcttttattc cgaaggcccg    300
aggcagggcg cgccggtgcc aggggtgtgg ctcgtgggca gagaccccaa gaacaacctg    360
gaagccttgg aggactttga gaaagccgca ggagcccgcg gactcagcac ggagagcatc    420
ctcatcccca ggcagagcga aaccagctct ccaggg                              456

<210> SEQ ID NO 81
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 71

<400> SEQUENCE: 81
gcctcagacg aggagattca ggatgtgtca gggacgtggt atctgaaggc catgacggtg     60
gacttcagcc gcggggacgc gatatggacg agcgtaacac cgatgaccct gactacactg    120
gagggcggca acctggaggc gaaggtcacc atgatgtatg ccggccgcag ccaggaagtc    180
aaagcggttt tagaaaggac cgacgaaccg ggcaaataca ccatgatggg tggcagccat    240
gtggcgtaca tcatccgtag ccctgtcaaa gatcactata tcttttattc cgaaggcccg    300
ctgcagggcg cgccggtgcc aggggtgtgg ctcgtgggca gagaccccaa gaacaacctg    360
gaagccttgg aggactttga gaaagccgca ggagcccgcg gactcagcac ggagagcatc    420
ctcatcccca ggcagagcga aaccagctct ccaggg                              456

<210> SEQ ID NO 82
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: Mutein of human tear lipocalin

<400> SEQUENCE: 82

```
Gly Ala Ser Asp Glu Glu Ile Gln Asp Val Ser Gly Thr Trp Tyr Leu
1               5                   10                  15

Lys Ala Met Thr Val Asp Arg Phe Lys Ile Ala Ser Trp Pro Arg Ser
            20                  25                  30

Val Thr Pro Met Thr Leu Thr Thr Leu Glu Gly Gly Asn Leu Glu Ala
        35                  40                  45

Lys Val Thr Met Asn Trp Trp Gly Arg Ser Gln Glu Val Lys Ala Val
    50                  55                  60

Leu Glu Arg Thr Asp Glu Pro Gly Lys Tyr Thr Ala Gln Gly Asp Arg
65                  70                  75                  80

His Val Ala Tyr Ile Ile Arg Ser His Val Lys Asp His Tyr Ile Phe
                85                  90                  95

Tyr Ser Glu Gly Asn Leu Gln Gly Glu Thr Val Pro Gly Val Trp Leu
            100                 105                 110

Val Gly Arg Asp Pro Lys Asn Asn Leu Glu Ala Leu Glu Asp Phe Glu
        115                 120                 125

Lys Ala Ala Gly Ala Arg Gly Leu Ser Thr Glu Ser Ile Leu Ile Pro
    130                 135                 140

Arg Gln Ser Glu Thr Ser Ser Pro Gly
145                 150
```

<210> SEQ ID NO 83
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 83

```
Ala Ser Asp Glu Glu Ile Gln Asp Val Ser Gly Thr Trp Tyr Leu Lys
1               5                   10                  15

Ala Met Thr Val Asp Arg Phe Lys Ile Ala Ser Trp Pro Arg Ser Val
            20                  25                  30

Thr Pro Met Thr Leu Thr Thr Leu Glu Gly Gly Asn Leu Glu Ala Lys
        35                  40                  45

Val Thr Met Asn Trp Trp Gly Arg Ser Gln Glu Val Lys Ala Val Leu
    50                  55                  60

Glu Arg Thr Asp Glu Pro Gly Lys Tyr Thr Ala Gln Gly Asp Arg His
65                  70                  75                  80

Val Ala Tyr Ile Ile Arg Ser Pro Val Lys Asp His Tyr Ile Phe Tyr
                85                  90                  95

Ser Glu Gly Asn Leu Gln Gly Glu Thr Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly Gly Gly Ser Leu Ala Glu Ala
145                 150                 155                 160

Lys Glu Ala Ala Asn Ala Glu Leu Asp Ser Tyr Gly Val Ser Asp Phe
```

```
                    165                 170                 175
Tyr Lys Arg Leu Ile Asp Lys Ala Lys Thr Val Glu Gly Val Glu Ala
                180                 185                 190

Leu Lys Asp Ala Ile Leu Ala Ala Leu Pro Gly
        195                 200
```

<210> SEQ ID NO 84
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutein of human tear lipocalin

<400> SEQUENCE: 84

```
Gly Ala Ser Asp Glu Glu Ile Gln Asp Val Ser Gly Thr Trp Tyr Leu
1               5                   10                  15

Lys Ala Met Thr Val Asp Arg Phe Lys Ile Ala Ser Trp Pro Arg Ser
                20                  25                  30

Val Thr Pro Met Thr Leu Thr Thr Leu Glu Gly Gly Asn Leu Glu Ala
            35                  40                  45

Lys Val Thr Met Asn Trp Trp Gly Arg Ser Gln Glu Val Lys Ala Val
        50                  55                  60

Leu Glu Arg Thr Asp Glu Pro Gly Lys Tyr Thr Ala Gln Gly Asp Arg
65                  70                  75                  80

His Val Ala Tyr Ile Ile Arg Ser His Val Lys Asp His Tyr Ile Phe
                85                  90                  95

Tyr Ser Glu Gly Asn Leu Gln Gly Glu Thr Val Pro Gly Val Trp Leu
                100                 105                 110

Val Gly Arg Asp Pro Lys Asn Asn Leu Glu Ala Leu Glu Asp Phe Glu
            115                 120                 125

Lys Ala Ala Gly Ala Arg Gly Leu Ser Thr Glu Ser Ile Leu Ile Pro
        130                 135                 140

Arg Gln Ser Glu Thr Ser Ser Pro Gly Lys Leu Gly Gly Gly Gly Ser
145                 150                 155                 160

Leu Ala Glu Ala Lys Glu Ala Ala Asn Ala Glu Leu Asp Ser Tyr Gly
                165                 170                 175

Val Ser Asp Phe Tyr Lys Arg Leu Ile Asp Lys Ala Lys Thr Val Glu
            180                 185                 190

Gly Val Glu Ala Leu Lys Asp Ala Ile Leu Ala Ala Leu Pro Gly Lys
        195                 200                 205

Leu Asn
    210
```

<210> SEQ ID NO 85
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Albumin binding domain (ABD)

<400> SEQUENCE: 85

```
Ser Leu Ala Glu Ala Lys Glu Ala Ala Asn Ala Glu Leu Asp Ser Tyr
1               5                   10                  15
```

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro Gly
        35                  40                  45

<210> SEQ ID NO 86
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 62

<400> SEQUENCE: 86
gcaagtgatg aagaaattca ggatgttagc ggcacctggt atctgaaagc aatgaccgtt    60
gatcgcttta aaatcgcaag ctggcctcgt agcgttaccc cgatgaccct gaccaccctg   120
gaaggtggta atctgaaagc aaaagttacc atgaattggg gggtcgtag ccaagaagtt    180 aaagcagttc tggaacgtac cgatgaaccg gtaaataca ccgcacaggg tgatcgtcat    240
gttgcatata tcattcgtag ccctgtgaaa gaccactaca tcttttatag cgaaggtaat    300
ctgcagggtg aaaccgttcc gggtgtttgg ctggttggtc gtgatccgaa aaataacctg   360
gaagcactgg aagattttga aaaagcagcc ggtgcacgtg gtctgagcac cgaaagcatt    420
ctgattccgc gtcagagcga aaccagcagt ccggga                             456

<210> SEQ ID NO 87
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 82

<400> SEQUENCE: 87
ggtgcaagtg atgaagaaat tcaggatgtt agcggcacct ggtatctgaa agcaatgacc    60
gttgatcgct ttaaaatcgc aagctggcct cgtagcgtta ccccgatgac cctgaccacc   120
ctggaaggtg gtaatctgga agcaaaagtt accatgaatt ggtggggtcg tagccaagaa   180
gttaaagcag ttctggaacg taccgatgaa ccgggtaaat acaccgcaca gggtgatcgt    240
catgttgcat atatcattcg tagccatgtg aaagaccact acatctttta tagcgaaggt    300
aatctgcagg gtgaaaccgt tccgggtgtt tggctggttg gtcgtgatcc gaaaaataac    360
ctggaagcac tggaagattt tgaaaaagca gccggtgcac gtggtctgag caccgaaagc    420
attctgattc cgcgtcagag cgaaaccagc agtccggga                          459

<210> SEQ ID NO 88
<211> LENGTH: 609
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 83

<400> SEQUENCE: 88
gcgagcgatg aagagatcca agacgtcagc ggcacctggt acctgaaagc aatgactgtc    60

```
gaccgtttta agatcgcgag ctggccgcgt agcgttacgc caatgaccct gacgaccctg    120
gagggcggca acttggaagc gaaggtgacg atgaattggt ggggtcgcag ccaagaagtg    180
aaagccgttc tggagcgcac ggacgagccg ggtaagtata ccgcgcaggg tgatcgtcat    240
gtggcatata tcattcgcag cccggtgaag gaccactaca ttttctactc tgagggtaat    300
ttgcagggtg aaaccgttcc tggcgtttgg ctggtcggtc gtgatccgaa aaacaatctg    360
gaagcactgg aggattttga aaagctgccg gtgcgcgtg gcctgtcgac cgagtctatt     420
ctgattccgc gccagtccga aacctccagc ccgggtggcg gtggtagcct ggcagaggcg    480
aaagaagcgg ctaacgctga gctgacagc tacggcgtga gcgatttcta taaacgtctg     540
atcgataagg ccaagaccgt cgagggtgtt gaagcgctga agacgccat cctggcggca     600 ttgccgggt                                                            609
```

```
<210> SEQ ID NO 89
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence of mutein shown in SEQ ID NO: 84

<400> SEQUENCE: 89
```

```
ggtgcaagtg atgaagaaat tcaggatgtt agcggcacct ggtatctgaa agcaatgacc    60
gttgatcgct ttaaaatcgc aagctggcct cgtagcgtta ccccgatgac cctgaccacc   120
ctggaaggtg gtaatctgga agcaaaagtt accatgaatt ggtggggtcg tagccaagaa   180
gttaaagcag ttctggaacg taccgatgaa ccgggtaaat acaccgcaca gggtgatcgt   240
catgttgcat atatcattcg tagccatgtg aaagaccact acatcttta tagcgaaggt   300 aatctgcagg gtgaaaccgt tccgggtgtt tggctggttg gtcgtgatcc gaaaaataac    360
ctggaagcac tggaagattt tgaaaaagca gccggtgcac gtggtctgag caccgaaagc    420
attctgattc gcgtcagag cgaaaccagc agtccgggta gcttggagg tggcggaagc     480 ctggcagaag caaaagaagc agcaaacgca gaactggata gctatggtgt tagcgatttc   540
tataaacgcc tgatcgataa agccaaaacc gttgaaggtg ttgaagcact gaaagatgca   600
attctggcag cactgccggg taagcttaat                                     630
```

```
<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Tyr Lys Asp Asp Asp Asp Lys Gly
1               5

<210> SEQ ID NO 91
<211> LENGTH: 10
<212> TYPE: PRT
<213> ORGANISM: Unknown
<220> FEATURE:
<223> OTHER INFORMATION: Description of Unknown: T7
      epitope peptide

<400> SEQUENCE: 91
```

```
Ala Ser Met Thr Gly Gly Gln Gln Met Gly
1               5                   10

<210> SEQ ID NO 92
<211> LENGTH: 11
<212> TYPE: PRT
<213> ORGANISM: Herpes simplex virus

<400> SEQUENCE: 92

Gln Pro Glu Leu Ala Pro Glu Asp Pro Glu Asp
1               5                   10

<210> SEQ ID NO 93
<211> LENGTH: 9
<212> TYPE: PRT
<213> ORGANISM: Herpes simplex virus

<400> SEQUENCE: 93

Tyr Pro Tyr Asp Val Pro Asp Tyr Ala
1               5

<210> SEQ ID NO 94
<211> LENGTH: 11
<212> TYPE: PRT
<213> ORGANISM: Vesicular stomatitis Indiana virus

<400> SEQUENCE: 94

Cys Tyr Thr Asp Ile Glu Met Asn Arg Leu Lys
1               5                   10

<210> SEQ ID NO 95
<211> LENGTH: 13
<212> TYPE: PRT
<213> ORGANISM: Unknown
<220> FEATURE:
<223> OTHER INFORMATION: Description of Unknown: E
      epitope tag peptide

<400> SEQUENCE: 95

Gly Ala Pro Val Pro Tyr Pro Asp Pro Leu Glu Pro Arg
1               5                   10

<210> SEQ ID NO 96
<211> LENGTH: 12
<212> TYPE: PRT
<213> ORGANISM: Unknown
<220> FEATURE:
<223> OTHER INFORMATION: Description of Unknown: E2
      epitope tag peptide

<400> SEQUENCE: 96

Gly Val Ser Ser Thr Ser Ser Asp Phe Arg Asp Arg
1               5                   10

<210> SEQ ID NO 97
<211> LENGTH: 12
<212> TYPE: PRT
<213> ORGANISM: Unknown
<220> FEATURE:
<223> OTHER INFORMATION: Description of Unknown: Tag-100
      mammalian MAPK/ERK epitope tag peptide

<400> SEQUENCE: 97

Glu Glu Thr Ala Arg Phe Gln Pro Gly Tyr Arg Ser
1               5                   10
```

<210> SEQ ID NO 98
<211> LENGTH: 15
<212> TYPE: PRT
<213> ORGANISM: Unknown
<220> FEATURE:
<223> OTHER INFORMATION: Description of Unknown: S-tag
      peptide

<400> SEQUENCE: 98

Lys Glu Thr Ala Ala Ala Lys Phe Glu Arg Gln His Met Asp Ser
1               5                   10                  15

<210> SEQ ID NO 99
<211> LENGTH: 10
<212> TYPE: PRT
<213> ORGANISM: Unknown
<220> FEATURE:
<223> OTHER INFORMATION: Description of Unknown: myc
      epitope transcription factor peptide

<400> SEQUENCE: 99

Glu Gln Lys Leu Ile Ser Glu Glu Asp Leu
1               5                   10

<210> SEQ ID NO 100
<211> LENGTH: 14
<212> TYPE: PRT
<213> ORGANISM: Simian virus 5

<400> SEQUENCE: 100

Gly Lys Pro Ile Pro Asn Pro Leu Leu Gly Leu Asp Ser Thr
1               5                   10

<210> SEQ ID NO 101
<211> LENGTH: 15
<212> TYPE: PRT
<213> ORGANISM: Unknown
<220> FEATURE:
<223> OTHER INFORMATION: Description of Unknown: S-peptide
      epitope

<400> SEQUENCE: 101

Lys Glu Thr Ala Ala Ala Lys Phe Glu Arg Gln His Met Asp Ser
1               5                   10                  15

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Ala Trp Ser His Pro Gln Phe Glu Lys
1               5                   10

<210> SEQ ID NO 103
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ala Ser Asp Glu Glu Ile Gln Asp Val Ser Gly Thr Trp Tyr Leu Lys

```
                1               5                  10                 15
Ala Met Thr Val Asp Arg Lys Asn Met Gly Gln Trp Pro Gly Ser Val
                20                 25                 30

Thr Pro Met Thr Leu Thr Thr Leu Glu Gly Gly Asn Leu Glu Ala Lys
                35                 40                 45

Val Thr Met Gln Arg Ala Gly Arg Ser Gln Glu Val Lys Ala Val Leu
                50                 55                 60

Glu Lys Thr Asp Glu Pro Gly Lys Tyr Thr Ala Ile Gly Gly Gln His
 65                 70                 75                  80

Val Ala Tyr Ile Ile Arg Ser His Val Lys Asp His Tyr Ile Phe Tyr
                    85                 90                 95

Ser Glu Gly Asp Arg Leu Gly Thr Pro Val Pro Gly Val Trp Leu Val
                    100                105                110

Gly Arg Asp Pro Lys Asn Asn Leu Glu Ala Leu Glu Asp Phe Glu Lys
                    115                120                125

Ala Ala Gly Ala Arg Gly Leu Ser Thr Glu Ser Ile Leu Ile Pro Arg
                130                135                140

Gln Ser Glu Thr Ser Ser Pro Gly
145                 150

<210> SEQ ID NO 104
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Ser Asp Glu Glu Ile Gln Asp Val Ser Gly Thr Trp Tyr Leu Lys
 1               5                  10                 15

Ala Met Thr Val Asp Phe Ser Arg Gly Asp Ala Ile Trp Thr Ser Val
                20                 25                 30

Thr Pro Met Thr Leu Thr Thr Leu Gly Gly Gly Asn Leu Glu Ala Lys
                35                 40                 45

Val Thr Met Met Tyr Ala Gly Arg Ser Gln Glu Val Lys Ala Val Leu
                50                 55                 60

Val Lys Thr Asp Glu Pro Gly Lys Tyr Thr Ala Met Gly Ser Ser His
 65                 70                 75                  80

Val Ala Tyr Ile Ile Arg Ser His Val Lys Asp His Tyr Ile Phe Tyr
                    85                 90                 95

Ser Glu Gly Pro Tyr Gln Gly Ala Pro Val Pro Gly Val Trp Leu Val
                    100                105                110

Gly Arg Asp Pro Lys Asn Asn Leu Glu Ala Leu Glu Asp Phe Glu Lys
                    115                120                125

Ala Ala Gly Ala Arg Gly Leu Ser Thr Glu Ser Ile Leu Ile Pro Arg
                130                135                140

Gln Ser Glu Thr Ser Ser Pro Gly
145                 150

<210> SEQ ID NO 105
<211> LENGTH: 4
<212> TYPE: PRT
<213> ORGANISM: Homo sapiens

<400> SEQUENCE: 105

His His Leu Leu
```

```
<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 106

His His His His His His
1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 107

Lys Leu Gly Gly Gly Gly
1               5
```

HUMAN TEAR LIPOCALINS WHICH BIND PCSK9 AND METHODS OF USE THEREOF

CROSS-REFERENCE TO RELATED APPLICATIONS

This application claims priority from U.S. Provisional Application No. 61/781,511, filed Mar. 14, 2013, and European Patent Application No. EP 13175023, filed Jul. 4, 2013, the entire contents of which are incorporated herein by reference.

The instant application contains a Sequence Listing which has been submitted in ASCII format via EFS-WEB and is hereby incorporated by reference in its entirety. Said ASCII copy, created on May 22, 2014, is named sequence.txt and is 122,037 bytes in size.

BACKGROUND

Human proprotein convertase subtilisin/kexin type 9 (PCSK9) is a secreted protein expressed primarily in the kidneys, liver and intestines. It has three domains: an inhibitory pro-domain (amino acids 1-152; including a signal sequence at amino acids 1-30), a serine protease domain (or catalytic domain; at amino acids 153-448), and a C-terminal domain (or cysteine/histidine-rich domain) of 210 residues in length (at amino acids 449-692), which is rich in cysteine residues. PCSK9 is synthesized as a zymogen that undergoes autocatalytic cleavage between the pro-domain and catalytic domain in the endoplasmic reticulum. The pro-domain remains bound to the mature protein after cleavage, and the complex is secreted. The cysteine-rich domain may play a role analogous to the P-(processing) domains of other Furin/Kexin/Subtilisin-like serine proteases, which appear to be essential for folding and regulation of the activated protease.

PCSK9 is a member of the proteinase K secretory subtilisin-like subfamily of serine proteases (Naureckiene et al., 2003 *Arc. Biochem. Biophys.* 420:55-67) and functions as a strong negative regulator of hepatic low density lipoprotein receptors (LDL-R). PCSK9 plays a critical role in cholesterol metabolism by controlling the levels of low density lipoprotein (LDL) particles that circulate in the bloodstream. Elevated levels of PCSK9 have been shown to reduce LDL-R levels in the liver, resulting in high levels of low density lipoprotein cholesterol (LDL-c) in the plasma and increased susceptibility to coronary artery disease. (Peterson et a.l, *J Lipid Res.* 49(7): 1595-9 (2008)).

The low-density lipoprotein receptor (LDL-R) prevents atherosclerosis and hypercholesterolemia through the clearance of the low-density lipoproteins (LDL) in the bloodstream. LDL-R is regulated at the posttranslational level by PCSK9. PCSK9 knockout mice showed an approximate 50% reduction in the plasma LDL-c levels and showed enhanced sensitivity to statins in reducing plasma LDL-c (Rashid S, et al (2005) Proc Natl Acad Sci 102:5374-5379. Human genetic data also support the role of PCSK9 in homeostasis. Mutations in PCSK9 are associated with abnormal levels of LDL-c in the blood plasma (Horton et al., 2006 *Trends. Biochem. Sci.* 32(2):71-77). Two mutations were recently identified that are presumably "loss-of-function" mutations in PCSK9. The individuals with these mutations have an approximately 40% reduction in the plasma levels of LDL-c which translates into an approximate 50-90% decrease in coronary heart disease.

Therefore, it would be highly advantageous to produce an inhibitor of PCSK9 that antagonizes the activity of PCSK9 and blocks or reduces the corresponding role PCSK9 plays in various pathologic conditions.

DEFINITIONS

The following list defines terms, phrases, and abbreviations used throughout the instant specification. All terms listed and defined herein are intended to encompass all grammatical forms.

As used herein, the term "lipocalin" refers to a polypeptide defined by its supersecondary structure, namely cylindrical β-pleated sheet supersecondary structural region comprising eight β-strands connected pair-wise by four loops at one end to define thereby a binding pocket. Lipocalins (Pervaiz and Brew, *FASEB J.* 1 (1987), 209-214) are a family of small, often monomeric secretory proteins which have been isolated from various organisms (Flower, *Biochem. J.* 318 (1996), 1-12). The lipocalins bear relatively little mutual sequence similarity and their belonging to the same protein structural family was first eluicidated by X-ray structure analysis (Sawyer et al., *Nature* 327 (1987), 659).

In this regard, a "lipocalin mutein", as used in the present discussed, refers to a mutein derieved from a lipocalin and having a cylindrical β-pleated sheet supersecondary structural region comprising eight β-strands connected pair-wise by four loops at one end to define thereby a binding pocket, wherein at least one amino acid of each of at least three of said four loops has been mutated (see, for example, PCT publication WO 199916873). In some particular embodiments, said lipocalin mutein may be derived from human tear lipocalin. In some other particular embodiments, however, said lipocalin mutein may be derived from a lipocalin other than human tear lipocalin.

As used herein, the term "subject" includes any vertebrates e.g., mammals. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "proprotein convertase subtilisin kexin type 9" ("PCSK9," interchangeable with "NARC-1") as used herein, refers to any native PCSK9 from any vertebrate source, including mammals such as primates (e.g. humans) and rodents (e.g., mice and rats), unless otherwise indicated. The term encompasses "full-length," unprocessed PCSK9 as well as any form of PCSK9 that results from processing in the cell or any fragment thereof. The term also encompasses naturally occurring variants of PCSK9, e.g., splice variants or allelic variants.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acid sequences to which they are operatively linked. Such vectors are referred to herein as "expression vectors."

DESCRIPTIONS OF FIGURES

FIG. 1A-1D: provides typical measurements of on-rate and off-rate by Surface Plasmon Resonance for the lipocalin muteins SEQ ID NO: 3, SEQ ID NO: 4, SEQ ID NO: 6 and SEQ ID NO: 11. The resulting dissociation constants ($K_D$) to human PCSK9 ("hPCSK9") (SEQ ID NO: 34), the association rates ($k_{on}$), and the dissociation rates ($k_{off}$) are summarized in Table 1 of Example 6.

Figure 2:
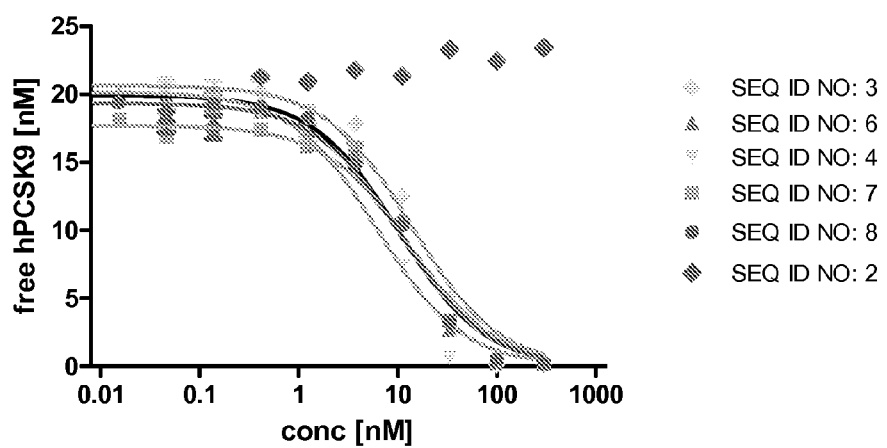
Figure 2:
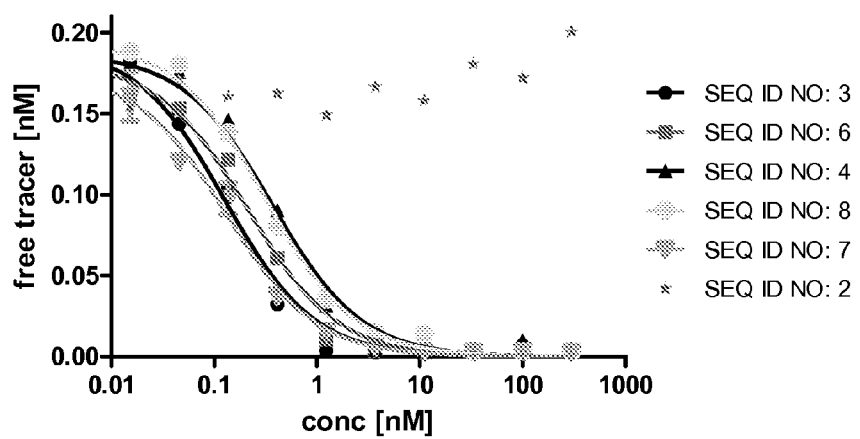

FIG. 2A-2B: demonstrates that the lipocalin muteins SEQ ID NO: 3, SEQ ID NO: 4, SEQ ID NO: 6, SEQ ID NO: 7 and SEQ ID NO: 8 were capable of blocking the interaction between PCSK9 and its receptor LDL-R. Either biotinylated hPCSK9 (FIG. 2A) or biotinylated hPCSK9_D374Y mutant (FIG. 2B) were pre-incubated with variable concentrations of said muteins and non-neutralized PCSK9 was quantified on an ELISA plate with immobilized soluble LDL-R. Negative control SEQ ID NO: 2 had no competitive effect. Data were fitted with a single-site binding model. Resulting IC50 values are summarized in Table 2 of Example 7.

FIG. 3A-3D: shows the crossreactivity profile of the lipocalin muteins of SEQ ID NO: 3, SEQ ID NO: 4, SEQ ID NO: 5, SEQ ID NO: 6, SEQ ID NO: 7, SEQ ID NO: 8 and SEQ ID NO: 9 as measured in an ELISA format. Full cross-reactivity of the lipocalin muteins to hPCSK9_D374Y mutant and to cynomolgus monkey PCSK9 is evident from nearly identical $K_D$ values (see Table 3). Within the concentration range tested, there is also crossreactivity to mouse PCSK9 but with lower affinities. No binding was detected of the negative control (SEQ ID NO: 2). Data were fitted with a single-site binding model.

Figure 4:
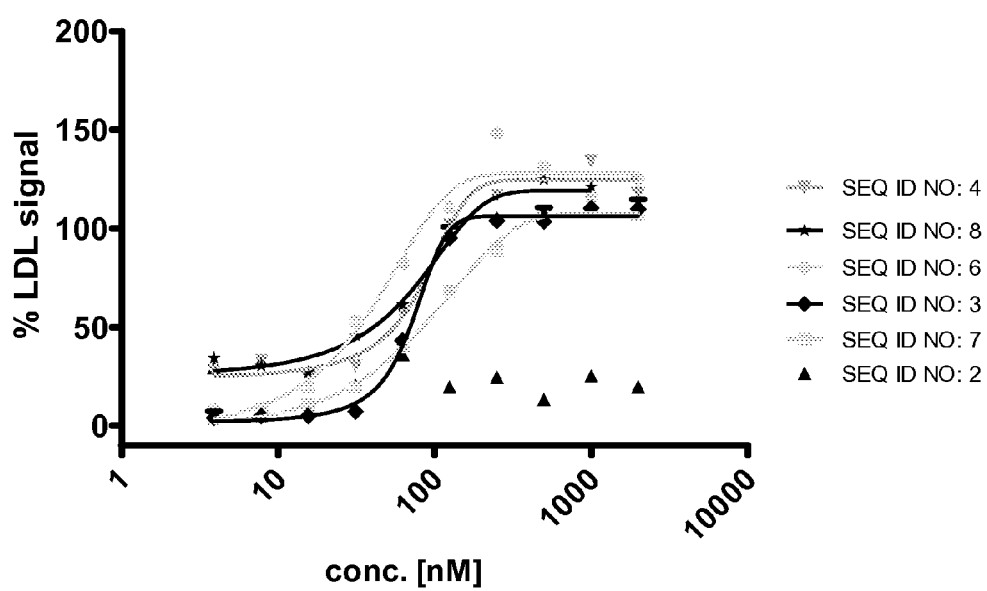

FIG. 4: illustrates that the lipocalin muteins of SEQ NO: 3, SEQ NO: 4, SEQ NO: 6, SEQ NO: 7, and SEQ NO: 8 are effective in blocking hPCSK9 binding to its receptor LDL-R in a cell-based assay. The assay is based on PCSK9-induced internalization of LDL-R on HepG2 cells leading to reduced intracellular uptake of fluorescence-labeled Dil-LDL. Cells are incubated with a fixed concentration of hPCSK9 (100 nM) and titrated with the lipocalin muteins. Plotted is the normalized fluorescence signal of intracellular Dil-LDL measured at 485535 nm using a BMG PheraStar reader, against the concentration of lipocalin muteins. The resulting IC50 values for the lipocalin muteins of SEQ NO: 3, SEQ NO: 4, SEQ NO: 6, SEQ NO: 7 and SEQ NO: 8 are given in Table 4. Binding of lipocalin muteins to PCSK9 restored PCSK9-mediated reduction of Dil-LDL uptake into cells whereas the negative control of SEQ ID NO: 2 had no effect. The curves were fitted by GraphPad Prism 4 using nonlinear regression "sigmoidal dose—response, variable slope" model (5PL fit). Data were normalized by the value of PCSK9 stimulated and non-stimulated cells.

FIG. 5A-5C: provides typical measurements of on-rate and off-rate for binding and unbinding of lipocalin muteins of SEQ ID NO: 13 (FIG. 5C), SEQ ID NO: 20 (FIG. 5A) and SEQ ID NO: 21 (FIG. 5B) to hPCSK9 as measured by Surface Plasmon Resonance. The resulting $K_D$s are summarized in Table 5 (see Example 10).

FIG. 6A-6C: provides typical measurements of on-rate and off-rate for binding and unbinding of lipocalin mutein (SEQ ID NO: 20) to various PCSK9 species as measured by Surface Plasmon Resonance. The resulting $K_D$ for lipocalin mutein SEQ ID NO: 20 and for other muteins are summarized in Table 6 (see Example 11).

Figure 7:
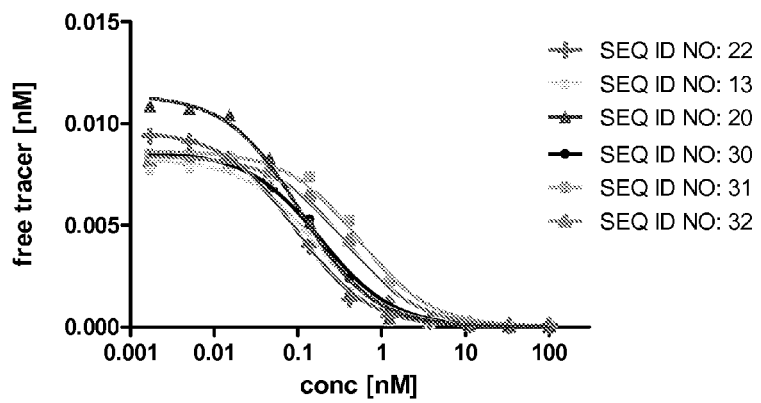

FIG. 7: demonstrates that the PEGylated versions of lipocalin muteins of SEQ ID NO: 30, SEQ ID NO: 31 and SEQ ID NO: 32 are capable of binding to hPCSK9 with an IC50 of 0.19, 0.53, and 0.37 nM, respectively, similar to the unmodified lipocalin mutein of SEQ ID NO: 13, which displayed an IC50 of 0.16 nM. Biotinylated hPCSK9 was pre-incubated with variable concentrations of the lipocalin muteins and non-neutralized hPCSK9 was quantified on an ELISA plate immobilized with a benchmark antibody (its light chain is represented by SEQ ID NO: 29 while its heavy chain is represented by SEQ ID NO: 33), which was used as a positive control to compete with the lipocalin muteins for binding to hPCSK9. Data were fitted with a single-site binding model.

Figure 8:
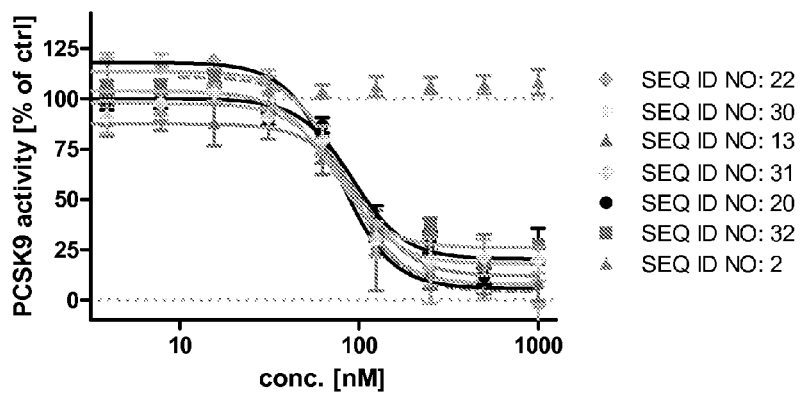

FIG. 8: demonstrates that the lipocalin muteins of SEQ ID NO: 22, SEQ ID NO: 13 and SEQ ID NO: 20 and their respective PEGylated variants of SEQ ID NO: 30, SEQ ID NO: 31 and SEQ ID NO: 32 are capable of blocking biological activity of hPCSK9 in a cell-based LDL-R depletion assay. Dilution series of the tested lipocalin muteins and negative control of SEQ ID NO: 2 are incubated with a constant concentration of hPCSK9 on LDL starved HepG2 cells. Levels of LDL-R on the HepG2 surface were assessed by using a specific goat anti-hLDL-R antibody (R&D Cat. No. AF2148). PCSK9-induced maximal LDL-R internalization was set up at 100%. Addition of lipocalin muteins blocked PCSK9's activity in a dose-dependent manner. In this regard, IC50 values for lipocalin muteins of SEQ ID NO: 22, SEQ ID NO: 13 and SEQ ID NO: 20 were 76 nM, 103 nM and 91 nM, respectively. Thus, PEGylation did not affect lipocalin muteins' blocking ability since IC50 measured for the PEGylated lipocalin muteins (comprising SEQ ID NOs: 30-32, respectively, which represent amino acid sequences of variants of three lipocalin muteins of the disclosure but do not include sequence of the polyethylene glycol (PEG) molecule) did not differ from their respective unPEGylated forms (SEQ ID NOs: 13, 20 and 22, respectively). Negative control of SEQ ID NO: 2 had no effect on PCSK9's activity. In summary, the lipocalin muteins inhibited biological activity of PCSK9 and therefore restore LDL-R on the cell surface. The data was fitted with a sigmoidal dose-response model.

Figure 9:
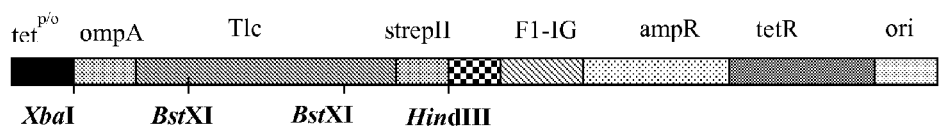

FIG. 9: shows the expression vector pTLPC26 (also called pTlc26) which encodes a fusion protein comprising the OmpA signal sequence (OmpA) and a human tear lipocalin mutein followed by the Strep-tag II. Both the BstXI-restriction sites used for the cloning of the mutated gene cassette and the restriction sites flanking the structural gene are labeled. Gene expression is under the control of the tetracycline promoter/operator)($tet^{p/o}$). Transcription is terminated at the lipoprotein transcription terminator ($t_{lpp}$). The vector further comprises an origin of replication (ori), the intergenic region of the filamentous phage f1 (f1-IG), the ampicillin resistance gene (amp) and the tetracycline repressor gene (tetR). A relevant segment of the nucleic acid sequence of pTLPC26 is given in the sequence listing as SEQ ID NO: 35. The segment begins with the XbaI restriction site and ends with the HindIII restriction site. The vector elements outside this region are identical with the vector pASK75, the complete nucleotide sequence of which is given in the German patent publication DE 44 17 598 A1.

FIG. 10: depicts an alignment of amino acid sequences of certain human tear lipocalin based muteins (listed as SEQ ID NOs: 2-11, 103, 13-18, 104 and 20-28) in comparison with the polypeptide sequence of mature human tear lipocalin (SEQ ID NO: 1).

Figure 11:
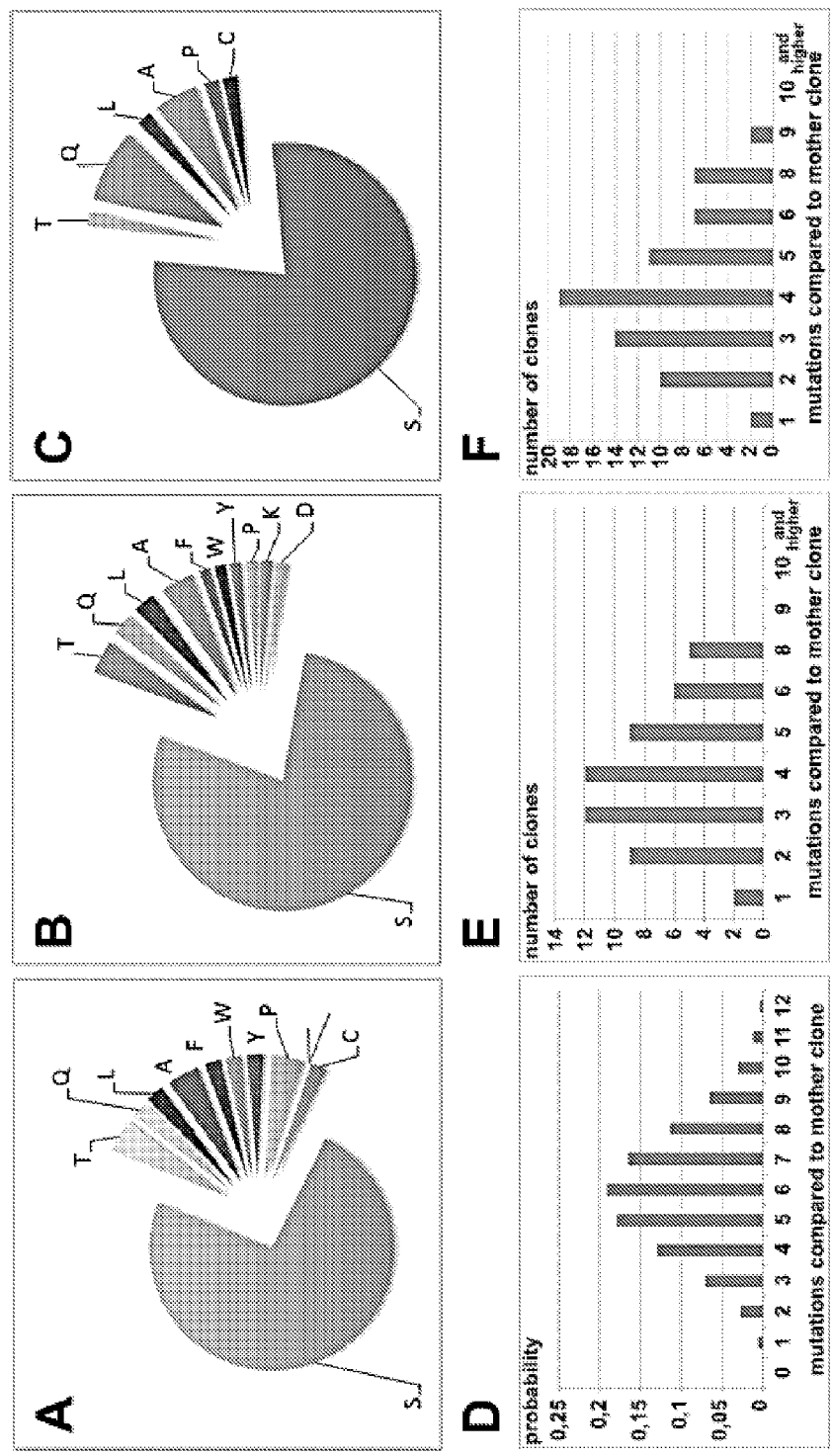

FIG. 11A-11F: FIG. 11A provides the expected distribution of amino acids encoded for Example 3. Note that for clarity, all amino acids having a frequency of less than 1% are omitted; the amber stop codon (TAG) is taken as encoding glutamine because a codon suppresor bacterial strain, TG1 F, is used in the phage display process. In addition, experimental data obtained from the sequencing of maturation libraries (FIG. 11B and FIG. 11 C) shows that there is a good match between the expected and the experimental distribution, albeit with the frequency of serine being higher than desired, reflecting either biases in oligo synthesis or oligo assembly by PCR. In line with this finding, the experimentally obtained frequency of mutation distributions for two libraries (FIG.

11E and FIG. 11F) are close to the theoretically expected distribution (FIG. 11D), but shifted to a lower frequency.

Figure 12:
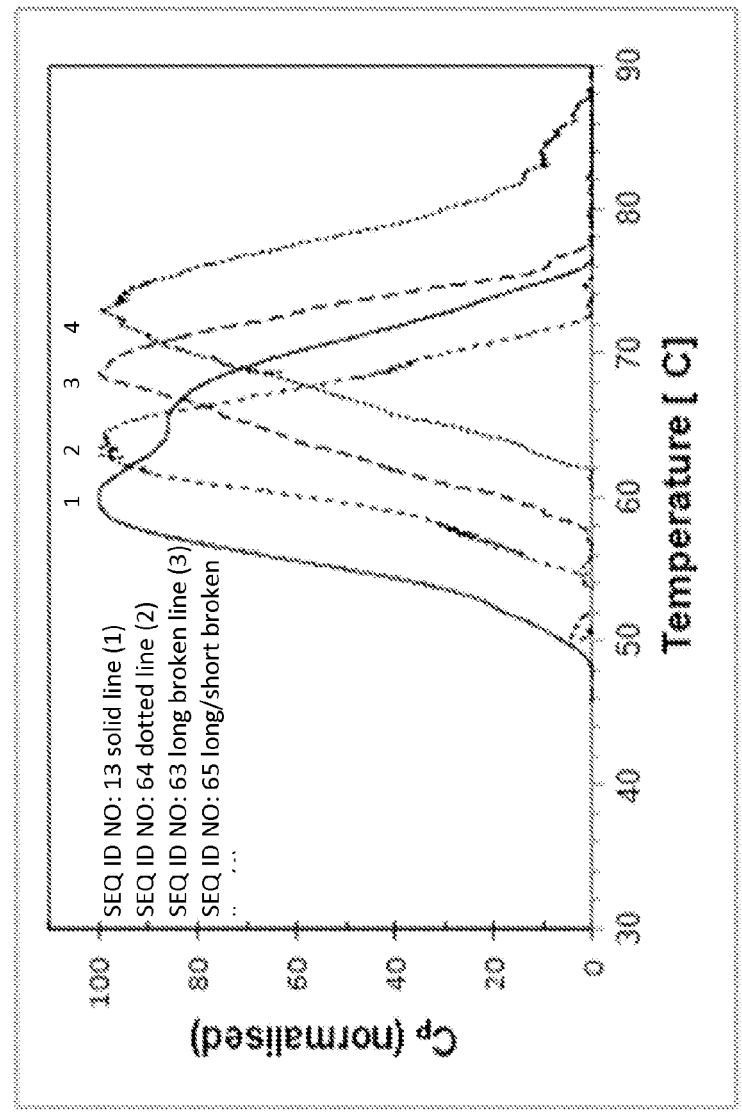

FIG. 12: depicts a thermogram, obtained from a nano Differential Scanning calorimeter ("nanoDSC") measurement using a capillary nanoDSC instrument (Q2000, TA Instruments), representing overlays of melting curves of lipocalin muteins (SEQ ID NO: 13 and SEQ ID NOs: 63-65). Melting curves of thermo-stabilized derivatives (SEQ ID NOs: 63-65) are significantly shifted compared to SEQ ID NO: 13.

FIG. 13A-13J: provides typical measurements of on-rate and off-rate by Surface Plasmon Resonance for the lipocalin muteins (SEQ ID NOs: 62-71). FIG. 13A-FIG. 13J corresponds to SEQ ID NOs: 62-71 respectively. The resulting dissociation constants (KD), the association rates (kon) and the dissociation rates (koff) to human PCSK9 ("hPCSK9") (SEQ ID NO: 34) are summarized in Table 10 of Example 17.

Figure 14:
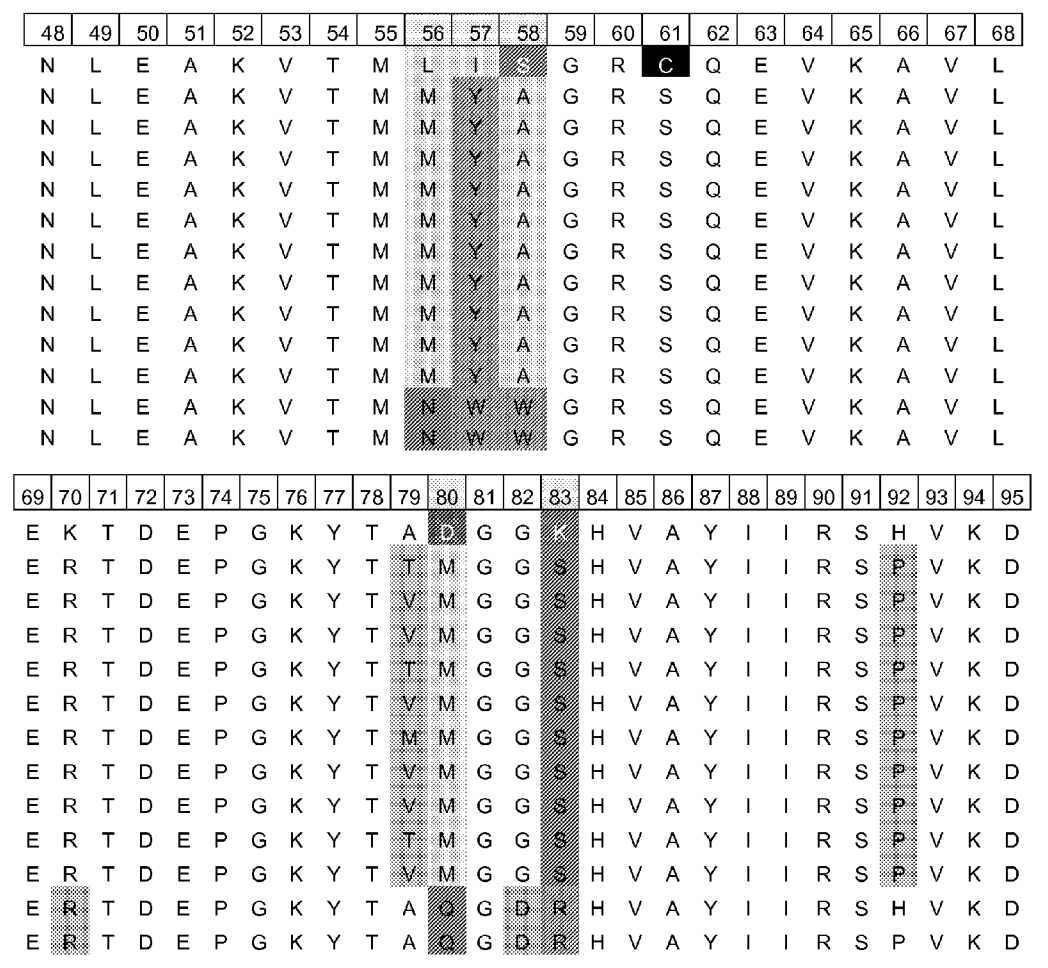
Figure 14:
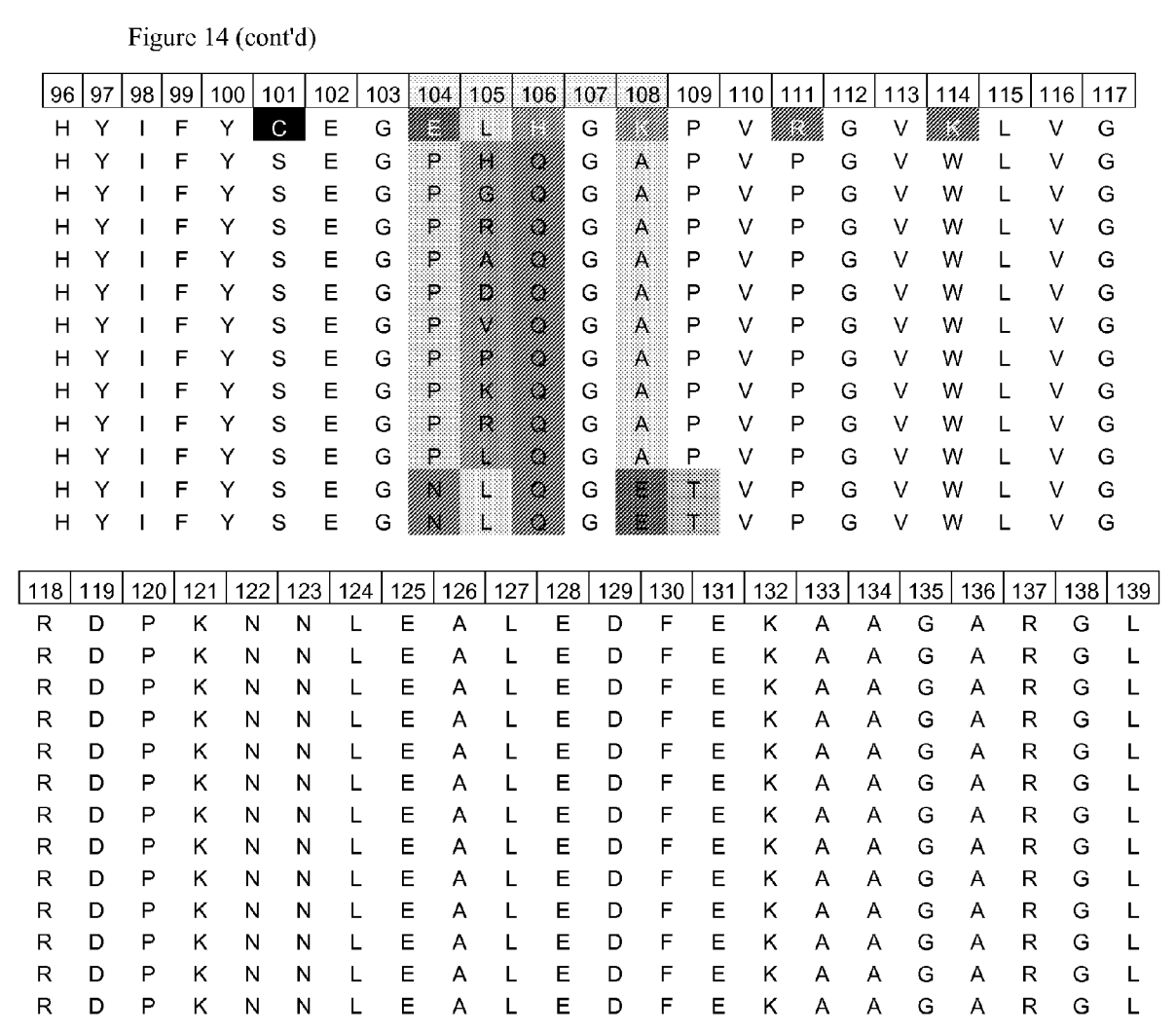

FIG. 14: depicts an alignment of amino acid sequences of certain human tear lipocalin based muteins (listed as SEQ ID NOs: 13, 22, 62-71) in comparison with the polypeptide sequence of mature human tear lipocalin (SEQ ID NO: 1).

DETAILED DESCRIPTION OF THE DISCLOSURE

In one aspect, the present disclosure provides muteins of human tear lipocalin that bind to proprotein convertase subtilisin/kexin type 9 or PCSK9. In some embodiments, the lipocalin muteins have a high affinity for PCSK9. PCSK9 as a target of a mutein of the present disclosure is typically a mammalian protein, for example, a non-human primate protein or a human protein. Full-length human PCSK9 has the amino acid sequence shown in SEQ ID NO: 34.

A lipocalin mutein of the disclosure may also be able to bind an immunogenic fragment of PCSK9. An immunogenic fragment of PCSK9 is a fragment that has one or more epitopes, mimotopes or other antigenic determinants, and is thus capable of inducing an immune response or against which an antibody can be raised. The immunogenic fragment may include a single epitope or may have a plurality of epitopes. Since an antigen-presenting system, e.g. a carrier protein, may be used to provide the size required for recognition by an immune system, no particular size limitation applies to the immunogenic fragment. Hence, the immunogenic fragment may also be a "hapten", i.e. a fragment that need not be antigenic per se or may have low immunogenicity, in particular due to its small molecular weight and accordingly size. Typically an immunogenic fragment can, alone or when presented on a carrier, be bound by an immunoglobulin. An immunogenic fragment of PCSK9 is typically capable of interacting with LDL-R and thereby modulating low density lipoprotein (LDL) particles that circulate in the bloodstream. In some embodiments, an immunogenic fragment of PCSK9 retains the capability of the full length ligand to be recognized and/or bound by a lipocalin mutein according to the disclosure. For example, the immunogenic fragment may be an N-terminally and/or C-terminally shortened protein or peptide.

In various embodiments, the lipocalin muteins of the disclosure are able to bind PCSK9 of a non-human primate PCSK9 (e.g., cynomolgus monkey PCSK9 or chimpanzee PCSK9) or an immunogenic fragment thereof with detectable affinity, i.e. with a $K_D$ of at least 200 nM. In some embodiments a lipocalin mutein of the disclosure may bind a non-human primate PCSK9 or an immunogenic fragment thereof with a $K_D$ equal to or less than about 10 nM, about 1 nM or about 0.3 nM. In various embodiments, antigen binding portion binds to mouse PCSK9 or an immunogenic fragment thereof with a $K_D$ equal to or less than about 10 nM, about 1 nM or about 0.5 nM.

In various embodiments, one or more lipocalin muteins of the disclosure are able to bind human PCSK9 or an immunogenic fragment thereof with detectable affinity, i.e. with a $K_D$ of at least 200 nM. In some embodiments a lipocalin mutein of the disclosure may bind human PCSK9 or an immunogenic fragment thereof with a $K_D$ equal to or less than about 10 nM, about 1 nM, about 0.1 nM, about 0.5 nM, about 0.25 nM, about 10 μM or even less.

In some further embodiments, binding affinities of one or more lipocalin muteins to human PCSK9 or an immunogenic fragment thereof have been found to be of a $K_D$ below 0.1 nM and in some embodiments be of a $K_D$ equal to or less than about 1 picomolar (pM) (see FIG. 7).

The binding affinity of a lipocalin mutein to a selected target, in the present case PCSK9, can be measured and thereby $K_D$ values of a mutein-ligand complex be determine by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Examples for such methods are detailed below (See e.g. Example 7).

In one embodiment, a lipocalin mutein of the disclosure may act as an antagonist of PCSK9. The term "antagonist of PCSK9," as used herein, refers to an agent that is capable of interfere with the binding between PCSK9 and LDL-R. In some cases, a PCSK9 antagonist can be identified by its ability to fully or partially inhibit the binding between PCSK9 and LDL-R.

Furthermore, a lipocalin mutein of the disclosure may be competitive for binding of LDL-R to PCSK9 (see Example 7).

In addition, a lipocalin mutein of the disclosure may be competitive for binding of a monoclonal antibody comprising SEQ ID NO: 29 and SEQ ID NO: 33 to PCSK9 (see Example 12).

In a further embodiment, a lipocalin mutein of the disclosure may be able to fully or partially inhibit PCSK9-mediated downregulation of LDL-R Inhibition occurs, for example, where PCSK9-mediated downregulation of LDL-R, when exposed to a lipocalin mutein of the disclosure, is at least about 10% less, e.g. at least about 25%, 50%, 75% less, or totally inhibited, in comparison to PCSK9-mediated downregulation of LDL-R in the presence of a control or in the absence of the lipocalin mutein. In some still further embodiments, a lipocalin mutein of the disclosure may be able to inhibit PCSK9-mediated downregulation of LDL-R in a dose-dependent manner. In some still further embodiments, the inhibition of PCSK9-mediated downregulation of LDL-R can be demonstrated in a HEPG2-cell-based assay as essentially described in Example 13.

In yet another embodiment, a lipocalin mutein of the disclosure may be able to restore LDL uptake in the presence of PCSK9. In some further embodiments, the restorage of LDL updtake in the presence of PCSK9 can be demonstrated in a HEPG2-cell-based assay as essentially described in Example 11. In some still furtherembodiments, to set up the assay, HEPG2 cells may be incubated with a fixed concentration of hPCSK9 (e.g. 100 nM) and then may be titrated with one or more lipocalin muteins.

PCSK9 can be taken to define a non-natural ligand of human tear lipocalin. The term "non-natural ligand" refers to a compound, which does not bind to mature human tear lipocalin under physiological conditions. The term "human tear lipocalin" as used herein refers to the mature human tear lipocalin corresponding to the protein of the SWISS-PROT Data Bank Accession Number P31025, while the mature human tear lipocalin (SEQ ID NO: 1) does not include the N-terminal signal peptide that is included in the sequence of SWISS-PROT Accession Number P31025.

The amino acid sequence of a mutein of the disclosure has a high sequence identity to mature human tear lipocalin (SEQ ID NO: 1). In this context, the amino acid sequence of a mutein of the disclosure may be substantially similar to the amino acid sequence of mature human tear lipocalin. A respective sequence of a lipocalin mutein of the disclosure, being substantially similar to the sequences of mature human tear lipocalin, may have in various embodiments at least 70%, at least 75%, at least 80%, at least 82%, at least 85%, at least 87% or at least 90% identity, including at least 95% identity, to the sequence of mature human tear lipocalin (see, for example, FIG. 10 and FIG. 14), with the proviso that the altered position or sequence is retained.

By "identity" is meant a property of sequences that measures their similarity or relationship. Identity is measured by dividing the number of identical residues by the total number of residues and multiplying the product by 100. As two illustrative examples, the mutein of the SEQ ID NO: 3 has a sequence identity of 82.28% with the amino acid sequence of mature human tear lipocalin, and the mutein of the SEQ ID NO: 7 has an amino acid sequence identity of 83.54% with mature human tear lipocalin.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) *Nucleic Acids Res.* 25, 3389-3402), Blast2 (Altschul, et al. (1990) *J. Mol. Biol.* 215, 403-410), and Smith-Waterman (Smith, et al. (1981) *J. Mol. Biol.* 147, 195-197).

The term "mutated" or "mutein" in reference to a nucleic acid or a polypeptide of the disclosure refers to the exchange, deletion, or insertion of one or more nucleotides or amino acids, respectively, compared to the naturally occurring nucleic acid or polypeptide. A mutein of the present disclosure includes at least three substitutions in comparison to the corresponding native human tear lipocalin.

In some embodiments, a mutein of human tear lipocalin according to the disclosure includes at least 2 including 3, 4, 5, 6, 8, 10, 12, 14, 15, 16, 17 or 18 mutated amino acid residues at any one of the sequence positions 26-34, 56-58, 80, 83, 104-106 and 108 of the linear polypeptide sequence of mature human tear lipocalin (SEQ ID NO: 1). The positions 26-34 are included in the AB loop, the positions 56-58 are included in the CD loop. The position 80 is located in a α-helical region. Position 83 is a single loop-defining amino acid between this α-helical region and a beta-sheet (βF). The positions 104-106 and 108 are included in the GH loop in the binding site at the open end of the β-barrel structure of tear lipocalin. The definition of these regions is used herein in accordance with Flower (Flower, 1996, supra, Flower, et al., 2000, supra) and Breustedt et al. (2005, supra).

In some embodiments, a human lipocalin mutein according to the disclosure may further include an amino acid substitution of a native cysteine residue at positions 61 and/or 153 by a serine residue. In this context it is noted that it has been found that removal of the structural disulfide bond (on the level of a respective native nucleic acid library) of mature human tear lipocalin that is formed by the cysteine residues 61 and 153 (cf. Breustedt, et al., 2005, supra) provides human tear lipocalin muteins that are not only stably folded but in addition are also able to bind a given non-natural ligand with high affinity. Without wishing to be bound by theory, it is also believed that the elimination of the structural disulfide bond provides the further advantage of allowing for the (spontaneous) generation or deliberate introduction of non-natural artificial disulfide bonds into muteins of the disclosure (see Examples), thereby increasing the stability of the muteins, for example. However, human tear lipocalin muteins that binds PCSK9 and that have the disulfide bond formed between Cys 61 and Cys 153 are also part of the present disclosure.

In some embodiments, a human tear lipocalin mutein of the disclosure includes the amino acid substitutions Cys 61→Ala, Phe, Lys, Arg, Thr, Asn, Tyr, Met, Ser, Pro or Trp and/or Cys 153→Ser or Ala.

In some embodiments, a human tear lipocalin mutein according to the disclosure includes an amino acid substitution of a native cysteine residue at position 101 by a serine residue. Further, in some embodiments, a human tear lipocalin mutein according to the disclosure includes an amino acid substitution of a native arginine residue at positions 111 by a proline residue. In some embodiments, a human tear lipocalin mutein according to the disclosure includes an amino acid substitution of a native lysine residue at positions 114 by a tryptophan residue.

In some embodiments, a human tear lipocalin mutein of the disclosure includes at least one amino acid substitution, which may be an additional amino acid substitution, selected from Arg 111→Pro and Lys 114→Trp. A human tear lipocalin mutein of the disclosure may further include the cysteine at position 101 of the sequence of mature human tear lipocalin substituted by another amino acid. This substitution may, for example, be the mutation Cys 101→Ser or Cys 101→Pro.

In some embodiments a human tear lipocalin mutein of the disclosure includes one or more of the following amino acid substitutions in comparison to mature human tear lipocalin: Arg 26→Ser, Phe, Trp, His or Thr, Glu 34→Asn, Thr, Arg or Gly, Leu 56→Met, Ser, Gln, Phe, His or Asn and Ser 58→Lys, Ala, Arg, Trp or Pro.

In some embodiments, a human tear lipocalin mutein according to the disclosure contains at least one of the following amino acid substitutions in comparison to mature human tear lipocalin: Met 31→Ala, Gly, His, Pro, Ser Aps, Glu or Gln, Leu 33→Tyr, Trp, Tyr, Phe, Pro or Ala, Ser 61→Trp or Phe, Asp 80→Ser, Met, Pro, Ile, Gln, Tyr, Ser, Val or Thr, Glu 104→Leu, Pro, Ser, Ala, Asn, Thr, Lys or Asp, His 106→Pro, Gln, Gly, Arg, Val, Thr, Asn or Leu and Lys 108→Gln, Ala, Trp, Tyr, Arg, Asp, Asn, Ser, Glu or Thr.

In some embodiments, a human tear lipocalin mutein according to the disclosure includes one or more of the following amino acid substitutions in comparison to mature human tear lipocalin: Glu 27→Arg, Ser, Gln, Thr, Phe, Lys, Ala or Arg, Pro 29→Gly, Asp, Asn, Ile, Leu or Met, Asn 32→Ile, Leu, Tyr, Met or Trp and Leu 105→Cys, Tyr, Trp, Glu, Arg, Ser, His, Ala, Val, Asp, Pro, Gly or Lys.

In some embodiments, a human tear lipocalin mutein according to the disclosure contains at least one of the following amino acid substitutions in comparison to mature human tear lipocalin: Phe 28→Cys, Arg, Lys, Trp, Asp, Gly, His, Leu or Asn; Glu 30→Arg, Asp, Thr, Ser, Gly, Ala or Asn, Ile 57→Tyr, Trp, His, Gln, Thr or Arg, Lys 83→Arg, Ser, Gln, Thr or Glu.

In some embodiments, a human tear lipocalin mutein according to the disclosure includes the combination of amino acid substitutions: Arg 26→Phe; Asn 32→Ile; Glu 34→Thr; Leu 56→Met; Ser 58→Ala and Lys 83→Ser, in comparison to mature human tear lipocalin. In some embodiments, a human tear lipocalin mutein according to the disclosure includes the combination of amino acid substitutions: Arg 26→Trp; Asn 32→Leu; Glu 34→Thr; Leu 56→Ser and Ser 58→Ala, in comparison to mature human tear lipocalin. In some embodiments, a human tear lipocalin mutein according to the disclosure includes the combination of amino acid substitutions: Arg 26→His; Asn 32→Tyr; Glu 34→Thr; Leu 56→Ser; Ser 58→Arg and Lys 83→Gln; in comparison to mature human tear lipocalin. In some embodiments, a human tear lipocalin mutein according to the disclosure includes the combination of amino acid substitutions: Arg 26→Phe; Asn 32→Met; Glu 34→Thr; Leu 56→Gln; Ser 58→Ala and Lys 83→Thr; in comparison to mature human tear lipocalin. In some embodiments, a human tear lipocalin mutein according to the disclosure includes the combination of amino acid substitutions: Asn 32→Trp; Glu 34→Arg; Leu 56→Asn; Ser 58→Trp and Lys 83→Ser, in comparison to mature human tear lipocalin. In some embodiments, a human tear lipocalin mutein according to the disclosure includes the combination of amino acid substitutions: Arg 26→Phe; Asn 32→Leu; Glu 34→Thr; Leu 56→Phe; Ser 58→Ala and Lys 83→Arg, in comparison to mature human tear lipocalin. In some embodiments, a human tear lipocalin mutein according to the disclosure includes the combination of amino acid substitutions: Arg 26→Thr; Asn 32→Trp; Glu 34→Asn; Leu 56→His; Ser 58→Pro and Lys 83→Ser, in comparison to mature human tear lipocalin. In some embodiments, a human tear lipocalin mutein according to the disclosure includes the combination of amino acid substitutions: Asn 32→Trp; Glu 34→Asn; Leu 56→Phe; Ser 58→Arg and Lys 83→Glu, in comparison to mature human tear lipocalin. In some embodiments, a human tear lipocalin mutein according to the disclosure includes the combination of amino acid substitutions: Arg 26→Trp; Asn 32→Leu; Glu 34→Thr; Leu 56→Met; Ser 58→Ala and Lys 83→Ser, in comparison to mature human tear lipocalin. In some embodiments, a human tear lipocalin mutein according to the disclosure includes the combination of amino acid substitutions: Asn 32→Trp; Glu 34→Gly; Leu 56→Gln; Ser 58→Ala and Lys 83→Gln, in comparison to mature human tear lipocalin.

In some embodiments, a human tear lipocalin mutein of the disclosure includes one of the following sets of amino acid substitutions:

(1) Glu 27→Ser; Phe 28→Arg; Pro 29→Gly; Glu 30→Asp; Met 31→Ala; Leu 33→Trp; Ile 57→Tyr; Asp 80→Met; Glu 104→Pro; Leu 105→Tyr; His 106→Gln; Lys 108→Ala, (2) Glu 27→Gln; Phe 28→Cys; Pro 29→Asp; Glu 30→Thr; Met 31→Gly; Leu 33→Trp; Ile 57→Tyr; Leu 105→Cys; His 106→Gly; Lys 108→Trp, (3) Glu 27→Glu; Phe 28→Trp; Pro 29→Asn; Glu 30→Gly; Met 31→His; Leu 33→Tyr; Ile 57→Tyr; Asp 80→Pro; Glu 104→Ser; Leu 105→Trp; His 106→Pro; Lys 108→Tyr, (4) Glu 27→Thr; Phe 28→Asp; Pro 29→Asn; Glu 30→Ser; Met 31→Pro; Leu 33→Phe; Ile 57→Tyr; Asp 80→Ile; Glu 104→Ala; Leu 105→Glu; His 106→Arg; Lys 108→Arg, (5) Glu 27→Phe; Phe 28→Lys; Pro 29→Ile; Glu 30→Ala; Met 31→Ser; Leu 33→Pro; Ile 57→Trp; Asp 80→Gln; Glu 104→Asn; Leu 105→Arg; His 106→Gln; Lys 108→Asp, (6) Glu 27→Lys; Phe 28→Gly; Pro 29→Pro; Glu 30→Thr; Met 31→Pro; Leu 33→Trp; Ile 57→His; Asp 80→Tyr; Glu 104→Ala; Leu 105→Ser; His 106→Val; Lys 108→Asn, (7) Glu 27→Glu; Phe 28→His; Pro 29→Leu; Glu 30→Ala; Met 31→Asp; Leu 33→Ala; Ile 57→Gln; Asp 80→Ile; Glu 104→Ala; Leu 105→Tyr; His 106→Pro; Lys 108→Ser, (8) Glu 27→Ala; Phe 28→Asp; Pro 29→Met; Glu 30→Gly; Met 31→Asp; Leu 33→Pro; Ile 57→Thr; Asp 80→Thr; Glu 104→Thr; His 106→Thr; Lys 108→Arg, (9) Glu 27→Arg; Phe 28→Leu; Pro 29→Asp; Glu 30→Asn; Met 31→Glu; Leu 33→Trp; Ile 57→Tyr; Asp 80→Gln; Glu 104→Pro; Leu 105→Arg; His 106→Asn; Lys 108→Ala,

(10) Glu 27→Lys; Phe 28→Asn; Pro 29→Met; Glu 30→Gly; Met 31→Gln; Leu 33→Pro; Ile 57→Arg; Asp 80→Ile; Glu 104→Asp; Leu 105→Arg; His 106→Leu; Lys 108→Thr, or

(11) Glu 27→Ser; Phe 28→Arg; Pro 29→Gly; Glu 30→Asp; Met 31→Ala; Leu 33→Trp; Ile 57→Tyr; Asp 80→Met; Glu 104→Pro; Leu 105→Gly; His 106→Gln; Lys 108→Ala.

In a particular embodiment, a human tear lipocalin mutein according to the disclosure includes the combination of amino acid substitutions: Arg 26→Phe; Glu 27→Ser; Phe 28→Arg; Pro 29→Gly; Glu 30→Asp; Met 31→Ala; Asn 32→Ile; Leu 33→Trp; Glu 34→Thr; Leu 56→Met; Ile 57→Tyr; Ser 58→Ala; Lys 83→Ser; Glu 104→Pro and Lys 108→Thr, in comparison to mature human tear lipocalin. In a still further embodiments, the human tear lipocalin mutein includes one or more of the following amino acid substitutions in comparison to mature human tear lipocalin: Thr 43→Ile or Ala, Glu 45→Gly, Asn 48→Gly, Glu 63→Gly, Ala 66→Vla, Glu 69→Vla, Lys 70→Arg, Ala 79→Thr, Met or Vla, Asp 80→Met or Ser, Gly 82→Ser, His 84→Gln, Vla 85→Gly, Tyr 87→Ser, Ile 88→Thr or Leu, His 92→Pro, Leu 105→His, Gly or Tyr and His 106→Gln or Arg.

In yet another particular embodiment, a human tear lipocalin mutein according to the disclosure includes the combination of amino acid substitutions: Glu 27→Phe; Phe 28→Lys; Pro 29→Ile; Asn 32→Trp; Leu 33→Pro; Glu 34→Arg; Leu 56→Asn; Ile 57→Trp; His 106→Gln and Lys 108→Glu, in comparison to mature human tear lipocalin. In a still further embodiments, the human tear lipocalin mutein includes one or more of the following amino acid substitutions in comparison to mature human tear lipocalin: Glu 43→Gly or Ala, Glu 45→Gly, Ser 58→Trp or Arg, Glu 63→Asp, Glu 69→Gly, Lys 70→Arg, Asp 80→Gln, Val or Thr, Gly 82→Asp, Lys 83→Ser or Arg, Ala 86→Glu or Ser, Phe 99→Leu, Glu 102→Lys or Val, Glu 104→Asn or Lys and Pro 106→Thr.

In some further embodiments, a human tear lipocalin mutein according to the disclosure comprises one or more mutated amino acid residues at any one of the amino acid sequence positions 79, 92 and 105 of the linear polypeptide sequence of mature human tear lipocalin. For example, a human tear lipocalin mutein of the disclosure may include the following amino acid substitutions: Ala 79→Met, Thr or Val, His 92→Pro and/or Leu 105→Ala, Val, Asp, Pro, Arg, Gly, Lys or His.

As defined above, a human tear lipocalin mutein of the disclosure includes at least one amino acid substitution, which is located at a sequence position of the positions 26, 27, 28, 30, 31, 33, 34, 57, 61, 80, 83, 104-106 and 108 of the linear polypeptide sequence of the mature human tear lipocalin (SEQ ID NO: 1). In some embodiments a mutein of the disclosure includes two or more, such as 3, 4, 5, 6, 7, 8, 9, 10, 11, 12, 13, 14, 15 or 16 amino acid substitutions of these sequence positions of the mature human tear lipocalin. In one particular embodiment, the mutein has a mutated amino acid residue at each of the sequence positions 26, 27, 28, 30, 31, 33, 53, 57, 61, 64, 66, 80, 83, 104-106 and 108 of the linear polypeptide sequence of the mature human tear lipocalin (see, for example, FIG. 10 and FIG. 14).

In some embodiments, a human tear lipocalin mutein of the disclosure may also include with respect to the amino acid sequence of mature human tear lipocalin one or more, including at least two, at least three or at least four amino acid substitutions of native amino acid residues by cysteine residues at any of positions within the loop regions of mature human tear lipocalin. In some embodiments, a mutein according to the disclosure includes an amino acid substitution of a native amino acid by a cysteine residue at positions 28 or 105 with respect to the amino acid sequence of mature human tear lipocalin.

In the residual region, i.e. the region differing from sequence positions 26-34, 56-58, 80, 83, 104-106 and 108, a human tear lipocalin mutein of the disclosure may include the wild type (natural) amino acid sequence outside the mutated amino acid sequence positions. In some embodiments, a human tear lipocalin mutein according to the disclosure may also carry one or more amino acid mutations at a sequence position positions as long as such a mutation does, at least essentially not hamper or not interfere with the binding activity and the folding of the mutein. Such mutations can be accomplished very easily on DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein (see for example, the experimental section in which muteins with truncated N- and C-terminus are generated).

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulfide bond formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulfide linkages. Exemplary possibilities of such a mutation to introduce a cysteine residue into the amino acid sequence of a human tear lipocalin mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective tear lipocalin mutein.

The present disclosure also encompasses muteins as defined above, in which the first four N-terminal amino acid residues of the sequence of mature human tear lipocalin (His-His-Leu-Leu; positions 1-4 (SEQ ID NO: 105)) and/or the last two C-terminal amino acid residues (Ser at position 157 and Asp at positions 158) of the sequence of mature human tear lipocalin have been deleted (see FIG. 10 and FIG. 14). Another possible mutation of the wild type sequence is to change the amino acid sequence at sequence positions 5 to 7 (Ala Ser Asp) to Gly Gly Asp as described in PCT publication WO 2005/019256.

The human tear lipocalin mutein of the disclosure may include, consist essentially of or consist of any one of the amino acid sequences set forth in SEQ ID NOs: 3-28, 62-71 and 82 or a fragment or variant thereof.

The term "fragment" as used herein in connection with the lipocalin muteins of the disclosure relates to proteins or peptides derived from full-length mature lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature lipocalin and are usually detectable in an immunoassay of the mature lipocalin.

The term "variant" as used in the present disclosure relates to derivatives of a lipocalin mutein of the disclosure that include modifications of the amino acid sequence, for example by substitution, deletion, insertion or chemical modification. Such modifications do in some embodiments not reduce the functionality of the mutein. For example, to generate such variant, one or more amino acids of a mutein of the disclosure can be replaced by their respective D-stereoisomers or by amino acids other than the naturally occurring 20 amino acids, such as, e.g. ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

A lipocalin mutein of the disclosure may exist as a monomeric protein. In some embodiments a lipocalin mutein according to the disclosure may be able to spontaneously dimerise or oligomerise. The use of lipocalin muteins that form stable monomers may be advantageous in some applications, e.g. because of faster diffusion and better tissue penetration. In other embodiments the use of a lipocalin mutein that spontaneously forms stable homodimers or multimers may be advantageous, since such multimers can provide (further) increased affinity and/or avidity to a given target. Furthermore, oligomeric forms of the lipocalin mutein may have slower dissociation rates or prolonged serum half-life. If dimerisation or multimerisation of muteins that form stable monomers is desired, this can for example be achieved by fusing respective oligomerization domains such as jun-fos domains or leucin-zippers to muteins of the disclosure or by the use of "Duocalins" (see also below).

A tear lipocalin mutein according to the present disclosure can be obtained by means of mutagenesis of a naturally occurring form of human tear lipocalin. The term "mutagenesis" as used herein means that the experimental conditions are chosen such that the amino acid naturally occurring at a given sequence position of human tear lipocalin (Swiss-Prot data bank entry P31025) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. PCT publication WO 2005/019256 which is incorporated by reference in its entirety herein). The term "random mutagenesis" means that no predetermined single amino acid (mutation) is present at a certain sequence position but that at least two amino acids can be incorporated with a certain probability at a predefined sequence position during mutagenesis.

The coding sequence of human tear lipocalin (Redl, B. et al. (1992) *J. Biol. Chem.* 267, 20282-20287) is used as a starting point for the mutagenesis of the peptide segments selected in the present disclosure. For the mutagenesis of the recited amino acid positions, the person skilled in the art has at his disposal the various established standard methods for site-directed mutagenesis. A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine, cytosine or thymine; K=guanine or thymine; S=adenine or cytosine) allows incorporation of all 20 amino acids plus the amber stop codon during mutagenesis, whereas the codon VVS (wherein V=adenine, guanine or cytosine) limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocysteine or pyrrolysine can also be incorporated into a nucleic acid of a mutein. It is also possible, as described by Wang, L., et al. (2001) *Science* 292, 498-500, or Wang, L., and Schultz, P. G. (2002) *Chem. Comm.* 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2'-deoxy-β-D-ribofuranosyl)-3,4-dihydro-8H-pyrimindo-1,2-oxazine-7-one (Zaccolo et al. (1996) *J. Mol. Biol.* 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekäs B, et al., (1994) *Nucleic Acids Res* 22, 5600-5607).

One possible strategy for introducing mutations in the selected regions of the respective polypeptides is based on the use of four oligonucleotides, each of which is partially derived from one of the corresponding sequence segments to be mutated. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid that includes the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning. For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

In an exemplary method according to the disclosure, a nucleic acid molecule encoding a human tear lipocalin is subjected to mutagenesis at one or more of the amino acid sequence positions 26-34, 56-58, 80, 83, 104-106 and 108 of the linear polypeptide sequence of mature human tear lipocalin (SEQ ID NO: 1). In some embodiments, the nucleic acid molecule is further subjected to mutagenesis at one or more of the amino acid sequence positions 61, 101, 111, 114 and 153 of the linear polypeptide sequence of the mature human tear lipocalin.

In one embodiment of the disclosure, a method for the generation of a mutein of human tear lipocalin includes mutating at least 2, 3, 4, 5, 6, 8, 10, 12, 14, 15, 16, or 17 of the codons of any of the amino acid sequence positions 26-34, 56-58, 80, 83, 104-106 and 108 of the linear polypeptide sequence of mature human tear lipocalin. In one embodiment, all 18 of the codons of amino acid sequence positions 26, 27, 28, 29, 30, 31, 32, 33, 34, 56, 57, 58, 80, 83, 104, 105, 106 and 108 of the linear polypeptide sequence of mature human tear lipocalin are mutated.

In a further embodiment of the disclosure, the methods according to the disclosure include the mutation of both of the codons encoding cysteine at positions 61 and 153 in the linear polypeptide sequence of mature human tear lipocalin (SEQ ID NO: 1). In one embodiment position 61 is mutated to encode an alanine, phenylalanine, lysine, arginine, threonin, asparagine, tyrosine, methionine, serine, proline or a tryptophane residue, to name only a few possibilities. In embodiments where position 153 is mutated, an amino acid such as a serine or alanine can be introduced at position 153.

In another embodiment of the disclosure as described herein, the codons encoding amino acid sequence positions 111 and/or 114 of the linear polypeptide sequence of mature human tear lipocalin are mutated to encode for example an arginine at position 111 and a tryptophane at position 114.

Another embodiment of the methods of the disclosure, involves mutagenesis of the codon encoding the cysteine at position 101 of the linear polypeptide sequence of mature human tear lipocalin so that this codon encodes any other amino acid. In one embodiment the mutated codon encoding position 101 encodes a serine. Accordingly, in some embodiments either two or all three of the cysteine codons at position 61, 101 and 153 are replaced by a codon of another amino acid.

According to the method of the disclosure, a lipocalin mutein is obtained starting from a nucleic acid molecule encoding human tear lipocalin. Such a nucleic acid molecule is subjected to mutagenesis and introduced into a suitable bacterial or eukaryotic host organism by means of recombinant DNA technology. Obtaining a nucleic acid library of lipocalin muteins can be carried out using any suitable technique that is known in the art for generating lipocalin muteins with antibody-like properties, i.e. muteins that have affinity towards a given target. Examples of such combinatorial methods are described in detail in the PCT publications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in its entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

The resulted nucleic acid molecules encoding one or more lipocalin muteins of the disclosure may be expressed using any suitable expression system. The obtained lipocalin mutein or lipocalin muteins can be further selected. The selection may for example be carried out under competitive conditions. Competitive conditions as used herein means that selection of lipocalin muteins encompasses at least one step in which the lipocalin muteins and the given non-natural ligand of wide-type lipocalin are brought in contact in the presence of an additional ligand, which competes with binding of the muteins to such non-natural ligand. This additional ligand may be a physiological ligand of the target, an excess of the target itself or any other non-physiological ligand of the target that binds at least an overlapping epitope to the epitope recognized by the muteins of the disclosure and thus interferes with target binding of the muteins. Alternatively, the additional ligand competes with binding of the muteins by complexing an epitope distinct from the binding site of the muteins to the target by allosteric effects.

An embodiment of the phage display technique (reviewed in Kay, B. K. et al. (1996), supra; Lowman, H. B. (1997) supra or Rodi, D. J., & Makowski, L. (1999), supra) using temperate M13 phage is given as an example of a selection method that can be employed in the present disclosure. Another embodiment of the phage display technology that can be used for selection of muteins of the disclosure is the hyperphage phage technology as described by Broders et al. (Broders et al. (2003) "Hyperphage. Improving antibody presentation in phage display." *Methods Mol. Biol.* 205:295-302). Other temperate phage such as f1 or lytic phage such as T7 may be employed as well. For the exemplary selection method, M13 phagemids are produced which allow the expression of the mutated lipocalin nucleic acid sequence as a fusion with a signal sequence at the N-terminus, such as the OmpA-signal sequence, and with the capsid protein pIII of the phage M13 or fragments thereof capable of being incorporated into the phage capsid at the C-terminus. The C-terminal fragment ΔpIII of the phage capsid protein that includes amino acids 217 to 406 of the wild type sequence is may be used to produce the fusion proteins. In one embodiment a C-terminal fragment of pIII is used, in which the cysteine residue at position 201 is missing or is replaced by another amino acid.

Accordingly, a further embodiment of the methods of the disclosure involves operably fusing a nucleic acid molecule coding for the one or more lipocalin muteins and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may include additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, such as an amber stop codon, is at least partially translated into an amino acid during translation in a suitable suppressor strain.

For example, the plasmid vector pTLPC27 (see, for example, FIG. 20 and SEQ ID NO: 9 of PCT publication WO 2008/015239), also called pTlc27, can be used for the preparation of a phagemid library encoding human tear lipocalin muteins. The inventive nucleic acid molecules coding for the tear lipocalin muteins may be inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

The resulting library is subsequently superinfected in liquid culture with an appropriate M13-helper phage or hyperphage in order to produce functional phagemids. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. In case of hyperphage display, the hyperphagemids display the lipocalin muteins on their surface as a fusion with the infective coat protein pIII but no native capsid protein. During or after infection with helper phage or hyperphage, gene expression of the fusion protein between the lipocalin mutein and the capsid protein pIII can be induced, for example by addition of anhydrotetracycline. The induction conditions are chosen such that a substantial fraction of the phagemids obtained displays at least one lipocalin mutein on their surface. In case of hyperphage display induction conditions result in a population of hyperphagemids carrying between three and five fusion proteins consisting of the lipocalin mutein and the capsid protein pIII. Various methods are known for isolating the phagemids, such as precipitation with polyethylene glycol. Isolation typically occurs after an incubation period of 6-8 hours.

The isolated plasmids can then be subjected to selection by incubation with the desired target, wherein the target is presented in a form allowing at least temporary immobilization of those phagemids which carry muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene. Microtiter plates suitable for ELISA techniques or so-called "immuno-sticks" can for instance be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin. If the target is fused to an Fc portion of an immunoglobulin, immobilization can also be achieved with surfaces, for example, microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. One such method is the elution using buffers of pH 2.2, wherein the eluate is subsequently neutralized. Alternatively, a solution of the free target can be added in order to compete with the immobilized target for binding to the phagemids or target-specific phagemids can be eluted by competition with immunoglobulins or natural liganding proteins which specifically bind to the target of interest.

Afterwards, *E. coli* cells are infected with the eluted phagemids. Alternatively, the nucleic acid sequences can be extracted from the eluted phagemids and used for sequence analysis, amplification or transformation of cells in another manner. Starting from the *E. coli* clones obtained in this way, fresh phagemids or hyperphagemids are again produced by superinfection with M13 helper phages or hyperphage according to the method described above and the phagemids amplified in this way are once again subjected to a selection on the immobilized target. Multiple selection cycles are often necessary in order to obtain the phagemids with the lipocalin muteins of the disclosure in optimized form. The number of selection cycles is in some embodiments chosen in such a way that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an *E. coli* strain is infected with the phagemids obtained from the selection cycles and the corresponding double stranded plasmid DNA is isolated. Starting from this plasmid DNA, or also from the single-stranded DNA extracted from the phagemids, the nucleic acid sequences of the selected muteins of the disclosure can be determined by the methods known in the art and the amino acid sequence can be deduced therefrom. The mutated region or the sequence of the entire lipocalin mutein can be subcloned on another expression vector and expressed in a suitable host organism. For example, the vector pTLPC26 (as referred in the description of FIG. 9), also called pTlc26, can be used for expression in *E. coli* strains such as *E. coli* TG1. A lipocalin mutein thus produced can be purified by various biochemical methods. A lipocalin mutein produced, for example with pTlc26, may carry an affinity peptide, a so called affinity tag, for instance at its C-terminus and can therefore be purified by affinity chromatography. Examples of an affinity tag include, but are not limited to biotin, the Strep-tag, Strep-tag II (Schmidt et al., supra), oligohistidine, polyhistidine, an immunoglobulin domain, maltose-binding protein, glutathione-S-transferase (GST) or calmodulin binding peptide (CBP).

Some affinity tags are haptens, for example but not limited to, dinitrophenol and digoxigenin. Some affinity tags are epitope tags, such as the FLAG®-peptide (Asp-Tyr-Lys-Asp-Asp-Asp-Asp-Lys-Gly) (SEQ ID NO: 90), the T7 epitope (Ala-Ser-Met-Thr-Gly-Gly-Gln-Gln-Met-Gly) (SEQ ID NO: 91), maltose binding protein (MBP), the HSV epitope of the sequence Gln-Pro-Glu-Leu-Ala-Pro-Glu-Asp-Pro-Glu-Asp (SEQ ID NO: 92) of herpes simplex virus glycoprotein D, the hemagglutinin (HA) epitope of the sequence Tyr-Pro-Tyr-Asp-Val-Pro-Asp-Tyr-Ala, (SEQ ID NO: 93), the VSV-G epitope of the Vesicular Stomatitis viral glycoprotein (Cys-Tyr-Thr-Asp-Ile-Glu-Met-Asn-Arg-Leu-Lys) (SEQ ID NO: 94), the E epitope tag of the sequence Gly-Ala-Pro-Val-Pro-Tyr-Pro-Asp-Pro-Leu-Glu-Pro-Arg (SEQ ID NO: 95), the E2 epitope tag of the sequence Gly-Val-Ser-Ser-Thr-Ser-Ser-Asp-Phe-Arg-Asp-Arg (SEQ ID NO: 96), the Tag-100 epitope tag of C-termini of mammalian MAPK/ERK kinases of the sequence Glu-Glu-Thr-Ala-Arg-Phe-Gln-Pro-Gly-Tyr-Arg-Ser (SEQ ID NO: 97), the S-tag of the sequence Lys-Glu-Thr-Ala-Ala-Ala-Lys-Phe-Glu-Arg-Gln-His-Met-Asp-Ser (SEQ ID NO: 98), the "myc" epitope of the transcription factor c-myc of the sequence Glu-Gln-Lys-Leu-Ile-Ser-Glu-Glu-Asp-Leu (SEQ ID NO: 99) and the small V5 epitope present on the P and V proteins of the paramyxovirus of Simian Virus 5 (Gly-Lys-Pro-Ile-Pro-Asn-Pro-Leu-Leu-Gly-Leu-Asp-Ser Thr) (SEQ ID NO: 100). In addition, but generally not as a single tag, a solubility-enhancing tag such as NusA, thioredoxin (TRX), small ubiquitin-like modifier (SUMO), and ubiquitin (Ub) may be used. Haptens and epitope tags may be used in combination with a corresponding antibody or an antibody like proteinaceous molecule as binding partner. The S-peptide epitope of the sequence Lys-Glu-Thr-Ala-Ala-Ala-Lys-Phe-Glu-Arg-Gln-His-Met-Asp-Ser (SEQ ID NO: 101) may be used as an epitope tag in connection with a respective antibody or in combination with the S-protein as a binding partner (Hackbarth, J S, et al., BioTechniques (2004) 37, 5, 835-839).

The selection can also be carried out by means of other methods. Many corresponding embodiments are known to the person skilled in the art or are described in the literature. Moreover, a combination of methods can be applied. For example, clones selected or at least enriched by "phage display" can additionally be subjected to "colony screening". This procedure has the advantage that individual clones can directly be isolated with respect to the production of a lipocalin mutein with detectable binding affinity for a target.

In addition to the use of *E. coli* as host organism in the "phage display" technique or the "colony screening" method, other bacterial strains, yeast or also insect cells or mammalian cells can be used for this purpose. Further to the selection of a lipocalin mutein from a random library as described above, evolutive methods including limited mutagenesis can also be applied in order to optimize a mutein that already possesses some binding activity for the target with respect to affinity or specificity for the target after repeated screening cycles.

It is readily apparent to the skilled person that complex formation is dependent on many factors such as concentration of the binding partners, the presence of competitors, ionic strength of the buffer system etc. Selection and enrichment is generally performed under conditions allowing the isolation of lipocalin muteins having, in complex with the desired target, a dissociation constant of at least 200 nM. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate. Alternatively, selection can be performed under conditions, which favor fast formation of the complex between the mutein and the target, or in other words a high $k_{on}$ rate. As a further illustrative alternative, the screening can be performed under conditions that select for improved thermo-stability of the muteins (compared to either wild type lipocalin or a mutein that already has affinity towards a pre-selected target).

Once a lipocalin mutein with affinity to a given target has been selected, it is additionally possible to subject such a mutein to another mutagenesis in order to subsequently select variants of even higher affinity or variants with improved properties such as higher thermo-stability, improved serum stability, thermodynamic stability, improved solubility, improved monomeric behavior, improved resistance against thermal denaturation, chemical denaturation, proteolysis, or detergents, etc. This further mutagenesis, which in case of aiming at higher affinity can be considered as in vitro "affinity maturation", can be achieved by site specific mutation based on rational design or a random mutation. Another possible approach for obtaining a higher affinity or improved proper- ties is the use of error-prone PCR, which results in point mutations over a selected range of sequence positions of the lipocalin mutein. The error-prone PCR can be carried out in accordance with any known protocol such as the one described by Zaccolo et al. (1996) *J. Mol. Biol.* 255, 589-603. Other methods of random mutagenesis that are suitable for such purposes include random insertiondeletion (RID) mutagenesis as described by Murakami, H et al. (2002) *Nat. Biotechnol.* 20, 76-81 or nonhomologous random recombination (NRR) as described by Bittker, J. A et al. (2002) *Nat. Biotechnol.* 20, 1024-1029. If desired, affinity maturation can also be carried out according to the procedure described in WO 00/75308 or Schlehuber, S. et al. (2000) *J. Mol. Biol.* 297, 1105-1120, where muteins of the bilin-binding protein having high affinity to digoxigenin were obtained.

In this regard, it is clear to the skilled person that the affinity's $K_D$ values (dissociation constant of the complex formed between the respective mutein and its ligand) may vary within a certain experimental range, depending on the method and experimental setup that is used for determining the affinity of a particular lipocalin mutein for a given ligand. This means, there may be a slight deviation in the measured $K_D$ values or a tolerance range depending, for example, on whether the $K_D$ value was determined by surface plasmon resonance (Biacore) or by competition ELISA.

Also included in the scope of the present disclosure are forms of the above muteins, in which the respective mutein has been altered or modified with respect to its potential immunogenicity.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. In order to reduce immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249, 244-250).

Such an approach may also be utilized to identify potential T-cell epitopes in the muteins of the disclosure and to make depending on its intended use a selection of a specific mutein on the basis of its predicted immunogenicity. It may be furthermore possible to subject peptide regions which have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19, 6, 463-471) and may be adapted to the muteins of the present disclosure.

The muteins thus obtained may possess a minimized immunogenicity, which is desirable for their use in therapeutic and diagnostic applications, such as those described below.

For several applications of the lipocalin muteins disclosed herein, the inventive lipocalin muteins may be fused, for example at their N-terminus or their C-terminus, to a moiety, which can be protein, a protein domain or a peptide such as a signal sequence and/or an affinity tag.

Affinity tags such as the Strep-Tag® or Strep-Tag® II (Schmidt, T. G. M. et al. (1996) *J. Mol. Biol.* 255, 753-766), the myc-tag, the FLAG-tag, the $His_6$-tag (SEQ ID NO: 106) or the HA-tag or proteins such as glutathione-S-transferase also allow easy detection and/or purification of recombinant proteins are further examples of suitable fusion partners.

Finally, proteins with chromogenic or fluorescent properties such as the green fluorescent protein (GFP) or the yellow fluorescent protein (YFP) are suitable fusion partners for a lipocalin mutein of the disclosure as well. For example, when used in the experiments described in Examples below, the lipocalin muteins disclosed herein carry a C-terminal Strep-Tag®II purification tag (IBA GmbH) consisting of 10 amino acids (SAWSHPQFEK) (SEQ ID NO: 102).

For some applications, it is also useful to employ the muteins of the disclosure in a labeled form. Accordingly, the disclosure is also directed to lipocalin muteins which are conjugated to a label moiety selected from the group consisting of enzyme labels, radioactive labels, colored labels, fluorescent labels, chromogenic labels, luminescent labels, haptens, digoxigenin, biotin, metal complexes, metals, and colloidal gold. The mutein may also be conjugated to a low molecular weight organic compound. The term "low molecular weight organic compound" as used herein denotes a monomeric carbon-based compound, which may have aliphatic, alicyclic and/or aromatic moieties. In typical embodiments the low molecular weight organic compound is an organic compound that has a main chain of at least two carbon atoms, and in some embodiments not more than 7 or 12 rotatable carbon bonds. Such a compound has a molecular weight in the range from about 100 to about 2000 Dalton, such as from about 100 to about 1000 Dalton. It may optionally include one or two metal atoms.

In general, it is possible to label the lipocalin mutein with any appropriate chemical substance or enzyme, which directly or indirectly generates a detectable compound or signal in a chemical, physical, optical, or enzymatic reaction. An example for a physical reaction and at the same time optical reactionmarker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present disclosure. The muteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonistsantagonists of a cell surface receptor or peptides competing for a protein binding site on a given cellular target). The lipocalin muteins of the disclosure may, however, also be conjugated with therapeutically active nucleic acid molecules such as antisense nucleic acid molecules, small interfering RNAs, micro RNAs or ribozymes. Such conjugates can be produced by methods well known in the art.

In one embodiment, the muteins of the disclosure may also be coupled to a moiety that can target a specific body region, organism, tissue, organ or cell within a subject in order to deliver the inventive muteins of the disclosure to a desired body region, organism, tissue, organ or cell of such subject. One example wherein such modification may be desirable is the crossing of the blood-brain-barrier. In order to cross the blood-brain barrier, the muteins of the disclosure may be coupled to moieties that facilitate the active transport across this barrier (see Gaillard P J, et al., Diphtheria-toxin receptor-targeted brain drug delivery. *International Congress Series,* 2005 1277, 185-198 or Gaillard P J, et al. Targeted delivery across the blood-brain barrier. *Expert Opin Drug Deliv.* 2005 2, 299-309. Such moieties are for example available under the trade name 2B-Trans™ (to-BBB technologies BV, Leiden, NL).

As indicated above, a lipocalin mutein of the disclosure may in some embodiments be conjugated to a moiety that can extend the serum half-life of the mutein (in this regard see also PCT publication WO 2006/56464 where such conjugation strategies are described with references to muteins of human neutrophile gelatinase-associated lipocalin with binding affinity for CTLA-4). When used in this specification, the term "conjugate" or "conjugation" includes that a moiety is linked to a lipocalin mutein by way of a chemical agent, e.g., a cross-linking agent or an agent which couples a moiety to a side group of an amino acid or the like. Also, said term when used herein is understood to include that a moiety is genetically fused to a lipocalin mutein at the either terminal end by way of forming a covalent bond, e.g., by translationally fusing a moiety that extends the half-life to a lipocalin mutein. The skilled person will understand from the context where said term is used whether a chemical agent is used for conjugation or whether a translational fusion is meant which is achieved by genetic engineering. The moiety that extends the serum half-life may be a polyalkylene glycol molecule, hydroxyethyl starch, fatty acid molecules, such as palmitic acid (Vajo & Duckworth (2000) *Pharmacol. Rev.* 52, 1-9), an Fc part of an immunoglobulin, a CH3 domain of an immunoglobulin, a CH4 domain of an immunoglobulin, albumin or a fragment thereof, an albumin binding peptide, or an albumin binding protein, transferrin to name only a few. The albumin binding protein may be a bacterial albumin binding protein, an albumin binding peptide, an engineered albumin binding polypeptide, an antibody, an antibody fragment including domain antibodies (see U.S. Pat. No. 6,696,245, for example), or a lipocalin mutein with binding activity for albumin. Accordingly, suitable conjugation partners for extending the half-life of a lipocalin mutein of the disclosure include albumin (Osborn, B. L. et al. (2002) *J. Pharmacol. Exp. Ther.* 303, 540-548), or an albumin binding protein, for example, a bacterial albumin binding domain, such as the one of streptococcal protein G (Konig, T., & Skerra, A. (1998) *J. Immunol. Methods* 218, 73-83). Examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002) *J. Biol. Chem.* 277, 35035-35043).

Streptococcal protein G (SpG) is a bi-functional receptor present on the surface of certain strains of streptococci and is capable of binding to both IgG and serum albumin (Bjorck et al, Mol Immunol 24:1 113, 1987). The structure is highly repetitive with several structurally and functionally different domains (Cuss et al, EMBO J. 5:1567, 1986), more precisely three Ig-binding domains and three serum albumin binding domains (Olsson et al, Eur J Biochem 168:319, 1987). The structure of one of the three serum albumin binding domains in SpG has been determined, showing a three-helix bundle fold (Kraulis et al, FEBS Lett 378:190, 1996, Johansson et al, J. Biol. Chem. 277:81 14-20, 2002). A 46 amino acid motif was defined as ABD (albumin binding domain) and has subsequently also been designated G148-GA3 (GA for protein G-related albumin binding). For example, in PCT publication WO 2009/016043, albumin binding variants of the 46 amino acid motif ABD are disclosed.

Other bacterial albumin binding domains than the ones in protein G have also been identified, some of which are structurally similar to the ones of protein G. Examples of proteins containing such albumin binding domains are the PAB, PPL, MAG and ZAG proteins (Kozak et al, Biochemistry 45:3263-3271, 2006). Studies of structure and function of such albumin binding domains have been carried out and reported e.g. by Johansson and coworkers (Johansson et al, J Mol Biol 266:859-865, 1997). Furthermore, Rozak et al have reported on the creation of artificial variants of G148-GA3, which were selected and studied with regard to different species specificity and stability (Rozak et al, Biochemistry 45:3263-3271, 2006), whereas Jonsson et al developed artificial variants of G148-GA3 having very much improved affinity for human serum albumin (Jonsson et al., Prot Eng Des Sel 21:515-27, 2008). For some of the variants a higher affinity was achieved at the cost of reduced thermal stability.

In addition to the three-helix containing proteins described above, there are also other unrelated bacterial proteins that bind albumin.

Recently, a few T- and B-cell epitopes were experimentally identified within the albumin binding region of Streptococcal protein G strain 148 (G148) (Goetsch et al, Clin Diagn Lab Immunol 10:125-32, 2003). The authors behind the study were interested in utilizing the T-cell epitopes of G148 in vaccines, i.e. to utilize the inherent immune-stimulatory property of the albumin binding region. Goetsch et al additionally found a B-cell epitope, i.e. a region bound by antibodies after immunization, in the sequence of G148.

However, in pharmaceutical compositions for human administration no immune-response is desired. Therefore, the albumin binding domain G148 is as such unsuitable for use in such compositions due to its abovementioned immune-stimulatory properties. Such drawbacks and deficiencies are overcome or alleviated by, for example, engineered albumin binding polypeptides disclosed in PCT publication WO 2012/004384, which is incorporated by reference in its entirety herein.

In this regard, lipocalin muteins of the disclosure may be conjugated to an albumin binding protein, which binds to human serum albumin ("HSA"), via one or more peptide-bond linkers, such as GGG and KLGGGG (SEQ ID NO: 107) as unlimiting examples. In some embodiments, such albumin binding protein may be an albumin binding domain such as Streptococcal protein G strain 148 (G148). In some other embodiments, the albumin binding protein may be an engineered albumin binding polypeptide. For example, the albumin binding polypeptide may have an amino acid sequence comprising SEQ ID NO: 85. The albumin binding polypeptide of SEQ ID NO. 85 may in some embodiments thus have additional amino acid residue(s) which is/are attached to the either terminal end, e.g. such as the three amino acids KLN. In this regard, the present disclosure provides exemplary conjugated lipocalin muteins, which comprises an amino acid sequence as set forth in any one of SEQ ID NOs: 83-84.

In other embodiments, albumin itself or a biological active fragment of albumin can be used as conjugation partner of a lipocalin mutein of the disclosure. The term "albumin" includes all mammal albumins such as human serum albumin ("HSA") or bovine serum albumin or rat albumin. The albumin or fragment thereof can be recombinantly produced as described in U.S. Pat. No. 5,728,553 or European patent applications EP 0 330 451 and EP 0 361 991. As a representative example, recombinant human albumin (Recombumin®) Novozymes Delta Ltd. (Nottingham, UK) can be conjugated or fused to a lipocalin mutein in order to extend the half-life of the mutein.

If the albumin-binding protein is an antibody fragment it may be a domain antibody. Domain Antibodies are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the disclosure, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the disclosure, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility and production efficiency.

Yet another alternative to prolong the half-life of a lipocalin mutein of the disclosure is to fuse long, unstructured, flexible glycine-rich sequences (for example, poly-glycine with about 20 to 80 consecutive glycine residues) to the N- or C-terminus of a lipocalin mutein of the disclosure. This approach disclosed in WO2007/038619, for example, has also been term "rPEG" (recombinant PEG).

If polyalkylene glycol molecule is used for the purpose to prolong the serum half-life of the muteins of the disclosure, the polyalkylene glycol can be substituted, unsubstituted, linear or branched. It can also be an activated polyalkylene derivative. Examples of suitable compounds are polyethylene glycol (PEG) molecules or activated derivatives thereof as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins J. Control. Release 11, 139-148). The molecular weight of such a polymer, such as polyethylene glycol, may range from about 300 to about 70,000 Dalton, including, for example, polyethylene glycol with a molecular weight of about 10,000, of about 20,000, of about 30,000 or of about 40,000 Dalton. Moreover, as e.g. described in U.S. Pat. Nos. 6,500,930 or 6,620,413, carbohydrate oligo- and polymers such as starch or hydroxyethyl starch (HES) can be conjugated to a mutein of the disclosure for the purpose of serum half-life extension. In some further embodiments, for the purpose to prolong the serum half-life of the muteins of the disclosure, PEG30 or PEG40 would be suggested in animals/humans with normal renal filtration rather than shorter PEGs, because i.e. the faster elimination of PEG12 or PEG20 may limit the effectiveness and duration of PEG-conjugated (PEGylated) lipocalin muteins of the disclosure. In this regard, the present disclosure provides exemplary lipocalin muteins as shown in SEQ ID NOs: 30-32 that can be PEG-conjugated.

In another embodiment, a lipocalin mutein of the disclosure may be fused to one or more moieties that can confer new characteristics to the fusion such as enzymatic activity or binding affinity for other molecules. Examples of such suitable moieties are alkaline phosphatase, horseradish peroxidase, glutathione-S-transferase, the albumin-binding domain of protein G, protein A, antibody fragments, oligomerization domains, lipocalin muteins of same or different binding specificity (which results in the formation of "Duocalins", cf. Schlehuber, S., and Skerra, A. (2001), Duocalins, engineered ligand-binding proteins with dual specificity derived from the lipocalin fold. *Biol. Chem.* 382, 1335-1342) or toxins.

In particular, it may be possible to fuse a lipocalin mutein of the disclosure with a separate enzyme active site such that both "components" of the resulting fusion may act together on a given therapeutic target. For example, when fused together, the binding domain of the lipocalin mutein can attach to a disease-causing target, thereby allowing the enzyme domain to abolish the biological function of the target.

If one of the above moieties is conjugated to the human tear lipocalin mutein of the disclosure, conjugation to an amino acid side chain can be advantageous. Suitable amino acid side chains may occur naturally in the amino acid sequence of human tear lipocalin or may be introduced by mutagenesis. In case a suitable binding site is introduced via mutagenesis, one possibility is the replacement of an amino acid at the appropriate position by a cysteine residue. In one embodiment, such mutation includes at least one of Thr 40→Cys, Glu 73→Cys, Arg 90→Cys, Asp 95→Cys or Glu 131→Cys substitution. The newly created cysteine residue at any of these positions can in the following be utilized to conjugate the mutein to moiety prolonging the serum half-life of the mutein, such as PEG or an activated derivative thereof.

In another embodiment, in order to provide suitable amino acid side chains for conjugating one of the above moieties to the muteins of the disclosure artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

In some embodiments, the lipocalin muteins according to the disclosure may contain a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences are known in the art. An illustrative signal sequence for secretion a polypeptide into the periplasm of *E. coli* is the OmpA-signal sequence.

The present disclosure also relates to nucleic acid molecules (DNA and RNA) that include nucleotide sequences coding for muteins as described herein. Since the degeneracy of the genetic code permits substitutions of certain codons by other codons specifying the same amino acid, the disclosure is not limited to a specific nucleic acid molecule encoding a mutein of the disclosure but encompasses all nucleic acid molecules that include nucleotide sequences encoding a functional mutein. In this regard, the present disclosure provides nucleic acid sequences (as shown in SEQ ID NOs: 36-61, 72-81 and 86-89) encoding certain lipocalin muteins of the disclosure.

Therefore, the present disclosure includes a nucleic acid sequence encoding a mutein according to the disclosure that has a mutation at at least one codon of any of the amino acid sequence positions 26-34, 56-58, 80, 83, 104-106 and 108 of the linear polypeptide sequence of mature human tear lipocalin, wherein the codons encoding at least one of the cysteine residues at sequence positions 61 and 153 of the linear polypeptide sequence of the mature human tear lipocalin have been mutated to encode any other amino acid residue. In some further embodiments, the nucleic acid sequence encoding a mutein according to the disclosure that has a mutation at at least one codon of any of the amino acid sequence positions 79, 92 and 105 of the linear polypeptide sequence of mature human tear lipocalin.

The disclosure as disclosed herein also includes nucleic acid molecules encoding tear lipocalin muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a plasmid. A plasmid vector denotes a vector encoding the intergenic region of a temperate phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein of the disclosure, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the disclosure, and in particular a cloning vector containing the coding sequence of such a lipocalin mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g. HeLa cells or CHO cells) or primary mammalian cells.

The disclosure also relates to a method for the production of a mutein of the disclosure, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eukaryotic host organism and then isolated from this host organism or its culture. It is also possible to produce a protein in vitro, for example by use of an in vitro translation system.

When producing the mutein in vivo a nucleic acid encoding a mutein of the disclosure is introduced into a suitable bacterial or eukaryotic host organism by means of recombinant DNA technology (as already outlined above). For this purpose, the host cell is first transformed with a cloning vector that includes a nucleic acid molecule encoding a mutein of the disclosure using established standard methods. The host cell is then cultured under conditions, which allow expression of the heterologous DNA and thus the synthesis of the corresponding polypeptide. Subsequently, the polypeptide is recovered either from the cell or from the cultivation medium.

In some tear lipocalin muteins of the disclosure, the naturally occurring disulfide bond between Cys 61 and Cys 153 is removed. Accordingly, such muteins (or any other tear lipocalin mutein that does not include an intramolecular disulfide bond) can be produced in a cell compartment having a reducing redox milieu, for example, in the cytoplasm of Gram-negative bacteria. In case a lipocalin mutein of the disclosure includes intramolecular disulfide bonds, it may be desired to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds. It is, however, also possible to produce a mutein of the disclosure in the cytosol of a host cell, such as *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, et al. (2002) *J. Mol. Biol.* 315, 1-6).

However, a lipocalin mutein of the disclosure may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the lipocalin muteins of the disclosure may be produced by in vitro transcriptiontranslation employing well-established methods known to those skilled in the art.

As is evident from the above disclosure, a lipocalin mutein of the present disclosure or a fusion protein or a conjugate thereof can be employed in many applications. In general, the muteins disclosed herein and its derivatives can thus be used in many fields similar to antibodies or fragments thereof. Therefore, numerous possible applications for the inventive muteins exist in medicine.

For example, the disclosure encompasses the use of one or more lipocalin muteins of the disclosure or one or more compositions comprising such muteins for the binding of PCSK9 in a subject and/or inhibiting the binding of PCSK9 to the low-density lipoprotein receptor (LDL-R), in a subject. In some embodiments, such use comprises administering to the subject an effective amount of one or more muteins of the disclosure or one or more compositions comprising such muteins. In this regard, the current application also discloses methods of binding PCSK9 as well as inhibiting the binding of PCSK9 to LDL-R in a subject, comprising administering to said subject an effective amount of one or more lipocalin muteins of the disclosure one or more compositions comprising such muteins.

In another aspect of the disclosure, the present disclosure involves the use of the lipocalin muteins of the disclosure for complex formation with PCSK9. In this context it is also noted that the complex formation between the respective mutein and its ligand is influenced by many different factors such as the concentrations of the respective binding partners, the presence of competitors, pH and the ionic strength of the buffer system used, and the experimental method used for determination of the $K_D$ (for example fluorescence titration, competition ELISA or surface plasmon resonance, just to name a few) or even the mathematical algorithm which is used for evaluation of the experimental data.

In some embodiments, the invented lipocalin muteins as disclosed herein can be used for the detection of PCSK9. Such use may include the steps of contacting the mutein with a sample suspected of containing the given ligand under suitable conditions, thereby allowing formation of a complex between the mutein and the given ligand, and detecting the complexed mutein by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

In another aspect, the disclosure provides for a kit comprising at least one mutein of the disclosure and one or more instructions for using the kit.

In some embodiments, the kit further includes integrally thereto or as one or more separate documents, information pertaining to the contents or the kit and the use of one or more muteins of the disclosure. The kit may include one or more muteins of the disclosure that are formulated for reconstitution in a diluent. Such a diluent, e.g. a sterile diluent, may also be included in the kit, for example within a container.

The lipocalin muteins disclosed herein may also be used for the separation of PCSK9. Such use may include the steps of contacting the mutein with a sample supposed to contain said ligand under suitable conditions, thereby allowing formation of a complex between the mutein and the ligand, and separating the mutein/ligand complex from the sample.

In the use of a mutein of the disclosure for the detection of PCSK9 as well as for the separation of PCSK9, the mutein and/or PCSK9 may be immobilized on a suitable solid phase.

In some embodiment, one or more lipocalin muteins of the disclosure may also be used to target a compound to a preselected organism, tissue, organ or cell to be treated with the compound, wherein PCSK9 is present in such organism, tissue, organ or cell. For such a purpose, the mutein is contacted with the compound of interest in order to allow complex formation. Then the complex that includes the mutein and the compound of interest are delivered to the preselected organism, tissue, organ or cell. This use is in particular suitable, but not restricted to, for delivering a drug (selectively) to a preselected organism, tissue, organ or cell, such as an infected body part, which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the preselected organism, tissue, organ or cell. Such a conjugate of mutein and compound may also include a linker that covalently links mutein and compound to each other. Optionally, such a linker is stable in the bloodstream but is cleavable in a cellular environment.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

EXAMPLES

Example 1

Production and Characterization of Recombinant Human PCSK9 and Human PCSK9 Mutant Human PCSK9 (SEQ ID NO: 34) containing a C-terminal FLAG tag was expressed in transfected HEK293F cells. 600 ml of transfected cells were cultivated in DMEM/TS/0.05% BSA for 6 days and the supernatant containing the hPCSK9 was recovered. hPCSK9 was bound to FLAG M2 resin, washed with 50 CV wash buffer (10 mM Tris/HCL pH7.4, 150 ml NaCl, 2 mM Cacl2, 10% glycerol) and eluted with 5 CV wash buffer containing 100 µg/ml 3×FLAG peptide. The eluted protein was further purified via gel filtration using a Superdex 200 1660 column (GE Healthcare). Functionality was tested with a LDL-R cell-ELISA using HepG2 cells.

For selection and screening of lipocalin muteins of interest, hPCSK9 may be biotinylated. hPCSK9 was incubated with a 5 times molar excess of EZ-Link NHS-Chromogenic Biotin reagent (Thermo Scientific) for 1 hr at room temperature. Excess of biotin was removed and the biotinylated protein was concentrated by ultrafiltration. A Streptacin pull-down assay confirmed biotinylation.

The gain of function hPCSK9_D374Y mutant, cynomolgus PCSK9 and mouse PCSK9 were produced and characterized in the same way.

Example 2

Generation of a Library with $2 \times 10^{10}$ Independent Lipocalin Muteins and Phagemid Selection of Lipocalin Muteins Against PCSK9

A random library of $2 \times 10^{10}$ lipocalin muteins with high diversity was generated by random mutagenesis of mature human tear lipocalin (see, for example, WO2007/107563). For selection of PCSK9-specific lipocalin muteins, $2 \times 10^{12}$ phagemids from this library were incubated with 200 nM biotinylated humand and/or cynomolgus PCSK9. Paramagnetic beads coated with neutravidin or streptavidin were used to capture PCSK9/phagemid complexes which were subsequently isolated with a magnet. Unbound phagemids were removed by washing the beads eight times with 1 ml PBS/T. Bound phagemids were eluted by incubation first with triethylamine and then with 0.1 M glycine pH 2.2. Four consecutive rounds of selection were performed.

The mutagenized central cassette of the plasmid preparation obtained after phage display selection was isolated by digestion of the DNA with BstX1 and subsequent purification via agarose gel electrophoresis using standard methods (Sambrook et al., (1989) *Molecular cloning: a laboratory manual*). The DNA was inserted into the likewise cut vector pTlc10 which allows bacterial production of the muteins under the control of a tetracyclin promoter. $CaCl_2$-competent TG1-F' cells were transformed with the ligation mixture and plated on LB/Amp plates. Individual colonies were used to inoculate 2×YT/Amp medium and grown overnight (14-18 h) to stationary phase. Subsequently, 50 µl 2×YT/Amp were inoculated from the stationary phase cultures and incubated for 3 h at 37° C. and then shifted to 22° C. until an $OD_{595}$ of 0.6-0.8 was reached. Anticalin production was induced by addition of 10 µl 2×YT/Amp supplemented with 1.2 µg/ml anhydrotetracyclin. Cultures were incubated at 22° C. until the next day. After addition of 40 µl of 5% (w/v) BSA in PBS/T and incubation for 1 h at 25° C. cultures were ready for use in screening assays.

For selection of lipocalin muteins, human and cynomolgus PCSK9 (1 µg/ml in PBS/T), which all carried a FLAG-tag, were captured on microtiterplates by means of an anti-FLAG-tag antibody (Sigma Aldrich, St. Louis, Mo.) which was coated on the plates the day before with an final concentration of 5 µg/ml in PBS. Anti-Flag-tag antibody alone served as negative control. Subsequently, 20 µl of BSA-blocked cultures were added and incubated for 1 h at 25° C. Bound muteins were detected with a 1:10000 dilution of anti-T7 antibody conjugated with horseradish peroxidase ("HRP", Merck KgaA, Darmstadt) in PBS/T. For quantification, 20 µl QuantaBlu fluorogenic peroxidase substrate was added and measured at an excitation wavelength of 320 nm and an emission wavelength of 430 nm.

Example 3

Generation of a Biased Maturation Library for Optimization of PCSK9-specific Lipocalin Muteins For optimization of PCSK9-specific muteins identified from the lipocalin library in above Example 2, additional libraries based on lipocalin muteins SEQ ID NO: 3, SEQ ID NO: 4 and SEQ ID NO: 7 (hereafter, named "mother clone(s)" in this example), respectively, were generated. The libraries were generated in a manner that leads to partial randomisation of selected positions only. The design was made such that, for each of the selected positions, the amino acid encoded corresponds to the amino acid found in the respective mother clone with a probability of 70%, while it can be a different amino acid with a 30% probability. With N the number of targeted positions and B as bias, the most probable number of exchanges per clone is N×(1−B). For example, if 20 amino acid positions are partially randomised with a 70% bias on the amino acid of the mother clone, this will result in a library of mutants on average containing six mutations overall compared to the mother clone, but on the targeted positions only. However, not all of the clones would have six exchanges: the frequency of mutations per clone will follow a binomial distribution, as depicted in FIG. 11D.

To assemble such libraries, recursive assembly of oligonucleotides in a polymerase chain reaction ("PCR") reaction (Stemmer et al., (1995) *Gene* 164:49-53) was used. The oligonucleotides are generated by standard phosphoramidite chemistry (Beaucage et al., (1981) *Tetrahedron Lett.* 22, 1859-62; McBride et al., (1983) *Tetrahedron Lett.* 24, 245-8). To allow an encoding of a 70% bias, we have calculated optimised mixtures for each position of a nucleotide triplet for each of the 20 canonical amino acids. For example, a mixture encoding serine with a bias of 70% and allowing various different amino acids in the remaining 30% is generated by the mixture of nucleoside phosphoramidite building blocks "abc", where a corresponds to a mixture of 85% thymidine, and 5% guanidine, cytosine and adenosine each, b corresponds to a mixture of 85% cytosine and 5% of the other nucleosides each, and c corresponds to a mixture of 50% guanidine and 50% thymidine (see FIG. 11).

Using the technology described above, said libraries based on SEQ ID NO: 3, SEQ ID NO: 4 and SEQ ID NO: 7, respectively, were generated by recursive PCR. Subsequently, the generated lipocalin muteins were cloned with high efficiently into a phagemid vector essentially as described (see, for example, Kim et al., (2009) *J Am Chem Soc* 131(10):3565-76). The library size ranged from $7 \times 10^9$ to $11 \times 10^9$ mutants. The libraries were employed in subsequent phage panning (see Example 4).

Example 4

Phagemid Selection of Optimized Lipocalin Muteins Against PCSK9

For selection of optimized PCSK9-specific lipocalin muteins, $2 \times 10^{12}$ phagemids from the libraries described in Example 3 were used. Phagemids were dissolved in PBS supplemented with 0.1% Tween-20 (v/v) (i.e. PBS/T), 50 mM benzamidine and 1% (w/v) casein. To select lipocalin muteins with increased affinity, phagemids were incubated with reduced concentrations of biotinylated PCSK9 proteins that ranged from 0.01 10 nM. In several instances, phagemids were incubated at 65° C. for 10 min to select for muteins with increased heat-tolerance. Blocked phagemids were incubated for 40 min with biotinylated PCSK9 proteins before 0.3 mM desthiobiotin was added to the solution to saturate free streptavidin binding sites and incubation was continued for 20 min. Subsequently, blocked (1% (w/v) casein in PBS/T) and drained paramagnetic beads that were either coated with streptavidin or neutravidin were added for 20 min to capture PCSK9-phagemid complexes. Uncomplexed phagemids were removed by washing the beads eight times with 1 ml PBS/T by thorough resuspension followed by collection of beads with a magnet. To specifically select muteins with reduced $k_{off}$ rates either a more stringent wash protocol was applied by performing 5 additional wash steps after round 1, 10 after round 2, 15 after round 3 and 20 after round 4 or mutein-PCSK9 complexes were incubated with different amounts (10 nM 5 µM) of purified parental mutein (e.g. SEQ ID NOs: 3, 4 or 7) to allow competition in PCSK9-binding between optimized and parental lipocalin muteins. Additionally, combinations of both methods were applied. Bound phagemids were first eluted with 300 µl 70 mM triethylamine for 10 min followed by immediate neutralization of the supernatant with 100 µl 1M Tris-Cl pH 6.0. After one intermediate wash cycle remaining phagemids were eluted with 100 mM glycin pH 2.2 for 10 min followed by immediate neutralization with 50 µl 0.5 M Tris-base. Both elution fractions were pooled and used to infect 4 ml of log-phase *E. coli* culture ($OD_{550}$ 0.45-0.6) for reamplification. After incubation for 30 min under agitation bacteria were collected by centrifugation at 5000×g for 2 min, resuspended in 1 ml 2×YT medium and plated on three big LB/Amp agar plates (10 g/l bacto tryptone, 5 g/l yeast extract, 5 g/l NaCl, pH 7.5, 15 g/l agar, 100 µg/ml ampicillin). Plates were incubated overnight at 32° C. Infected cells were scraped from the agar plates using 50 ml 2×YT medium supplemented with 100 µg/ml ampicillin (2×YT/Amp). 50 ml 2×YT/Amp medium were inoculated with the appropriate volume of bacterial suspension to reach an $OD_{550}$ of 0.08. The culture was incubated at 37° C. on a shaker (160 rpm) until an $OD_{550}$ of 0.5 was reached and then infected with helperphages ($1.5 \times 10^{11}$ pfu) by incubation for 15 min with gentle agitation and for 45 min on a shaker at 37° C. Subsequently, kanamycin was added to a final concentration of 70 µg/ml to select for bacteria that were infected by helperphages. Finally, expression of the pIII-lipocalin proteins was induced by addition of 25 ng/ml anhydrotetracyclin.

Example 5

Identification of PCSK9-specific Tlc Muteins by Screening

The mutagenized central cassette of the plasmid preparation obtained after phage display selection, as described in Example 4, was isolated by digestion of the DNA with BstX1 and subsequent purification via agarose gel electrophoresis using standard methods (Sambrook et al. 1989). The DNA was inserted into a likewise-cut vector which allowed bacterial production of the muteins under the control of a tetracyclin promoter. $CaCl_2$-competent TG1-F' cells were transformed with the ligation mixture and plated on LB/Amp plates. Individual colonies were used to inoculate 2×YT/Amp medium and grown overnight (14-18 h) to stationary phase.

Subsequently, 50 µl 2×YT/Amp were inoculated from the stationary phase cultures and incubated for 3 h at 37° C. and then shifted to 22° C. until an $OD_{595}$ of 0.6-0.8 was reached. Lipocalin-mutein production was induced by addition of 10 µl 2×YT/Amp supplemented with 1.2 µg/ml anhydrotetracyclin. Cultures were incubated at 22° C. until the next day. After addition of 40 µl of 5% (w/v) BSA in PBS/T and incubation for 1 h at 25° C. cultures were ready for use in screening assays.

For selection of lipocalin muteins, human and cynomolgus PCSK9 (1 µg/ml in PBS/T) as well as hPCSK9-D374Y mutant, which all carried a FLAG-tag, were captured on microtiterplates by means of an anti-FLAG-tag antibody (Sigma Aldrich, St. Louis, Mo.), which was coated on the plates the day before with an final concentration of 5 µg/ml in PBS. Subsequently, 20 µl of BSA-blocked cultures were added and incubated for 1 h at 25° C. Bound lipocalin muteins were detected with a 1:10000 dilution of anti-T7 antibody conjugated with HRP (Merck KgaA, Darmstadt) in PBS/T. For quantification, 20 µl QuantaBlu fluorogenic peroxidase substrate was added and measured at an excitation wavelength of 320 nm and an emission wavelength of 430 nm.

For affinity ranking of lipocalin muteins, anti-Strep-tag antibody (IBA, Goettingen) in PBS was coated on microtiterplates and 20 µl of BSA-blocked cultures were added, which allowed specific capture of lipocalin muteins on the plate. Different concentrations (0.5-5 nM) of biotinylated PCSK9 proteins were added and specifically-bound PCSK9 proteins were detected with extravidin-HRP (Sigma Aldrich, St. Louis, Mo.) after extensive washing. For quantification, 20 µl QuantaBlu was added and measured at an excitation wavelength of 320 nm and an emission wavelength of 430 nm.

Selection of competitive lipocalin muteins was performed by coating anti-FLAG-tag (5 µg/ml in PBS) on microtiterplates and subsequently capturing hPCSK9-D374Y mutant (1 µg/ml in PBS/T). Blocked cultures were adjusted to 30 nM purified LDL receptor and added for 72 h to plates with captured hPCSK9-D374Y mutant. This allowed equilibration of the system and reliable selection of competitive muteins. Bound receptor was detected with an HRP-conjugated anti-His-tag antibody (1 µg/ml in PBS/T; Abcam, Cambridge, UK). For quantification, 20 µl QuantaBlu fluorogenic peroxidase substrate was added and measured at an excitation wavelength of 320 nm and an emission wavelength of 430 nm.

Example 6

Affinity of Representative Lipocalin Muteins to PCSK9

To measure the binding affinity of a representative group of lipocalin muteins to biotinylated PCSK9, a Surface Plasmon Resonance (SPR) based assay was employed utilizing a Biacore T200 instrument (GE Healthcare). For the SPR affinity assay (FIG. 1), the Biotin CAPture Kit (GE Healthcare) was used.

In each measurement cycle, Biotin CAPture Reagent (GE Healthcare) was applied to the reference and measurement channels of Sensor Chip CAP (GE Healthcare) for 5 min at a flow rate of 2 µl/min. Biotinylated PCSK9 at a concentration of 4 µg/ml was injected on the measurement channel for 2 min at a flow rate of 10 µl/min. To determine the affinity, three to four dilutions of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12 were prepared in HBS-EP+ (0.01 M HEPES pH 7.4, 0.15 M NaCl, 3 mM EDTA, 0.005% Surfactant P20) buffer and applied to the chip surface, using concentrations of 500, 125, 31 and 8 nM for SEQ ID NO: 3, SEQ ID NO: 6, SEQ ID NO: 11, and SEQ ID NO: 12, concentrations of 300, 75, 19 and 5 nM for SEQ ID NO: 4, SEQ ID NO: 5, SEQ ID NO: 8, SEQ ID NO: 9 and SEQ ID NO: 10, and concentrations of 75, 19 and 5 nM for SEQ ID NO: 7. The binding assay was carried out with a contact time of 3 min, dissociation time of 20 min and applying a flow rate of 30 µl/min. All measurements were performed at 25° C. Regeneration of the Sensor Chip CAP surface was achieved with an injection of 6 M guanidine-HCl with 0.25 M NaOH (2 min) followed by an extra wash with running buffer and a stabilization period of 2 min. Prior to the measurements, one conditioning cycle consisting of three consecutive regeneration steps was performed. Data were evaluated with Biacore T200 Evaluation software (V 1.0). Double referencing was used. The 1:1 binding model was used to fit the raw data.

The resulting fit curves for SEQ ID NO: 3, SEQ ID NO: 4, SEQ ID NO: 6 and SEQ ID NO: 11 are shown in FIG. 1 (A-D), respectively. For example, the data shows that SEQ ID NO: 3 (FIG. 1A) bound with high affinity to PCSK9 ($K_D$=0.85 nM). Association rate constants $k_a$ or $k_{on}$, dissociation rate constants $k_d$ or $k_{off}$ and the resulting dissociation constants $K_D$ for all lipocalin muteins are summarized in Table 1 below.

TABLE 1

| Molecule | $k_{on}$ [M$^{-1}$*s$^{-1}$] | $k_{off}$ [s$^{-1}$] | $K_D$ [nM] |
|---|---|---|---|
| SEQ ID NO: 3 | 1.77E+05 | 1.50E−04 | 0.85 |
| SEQ ID NO: 4 | 4.79E+04 | 1.39E−04 | 2.89 |
| SEQ ID NO: 5 | 3.40E+04 | 1.63E−04 | 4.8 |
| SEQ ID NO: 6 | 5.66E+04 | 2.32E−04 | 4.1 |
| SEQ ID NO: 7 | 7.24E+05 | 4.84E−03 | 6.69 |
| SEQ ID NO: 8 | 1.54E+05 | 1.38E−03 | 8.96 |
| SEQ ID NO: 9 | 2.33E+05 | 4.80E−03 | 20.59 |
| SEQ ID NO: 10 | 5.70E+05 | 7.19E−03 | 12.61 |
| SEQ ID NO: 11 | 4.70E+04 | 8.90E−05 | 1.89 |
| SEQ ID NO: 12 | 2.44E+04 | 1.56E−04 | 6.4 |

Example 7

Competitive Mode of Action of Representative Lipocalin Muteins to PCSK9

Whether lipocalin muteins disclosed in Example 6 bind to PCSK9 in a competitive mode was tested in vitro using a competition ELISA format. In this experiment, a constant concentration of human PCSK9 (SEQ ID NO: 34) or human PCSK9_D374Y mutant was incubated with variable concentrations of lipocalin muteins for 1 h. After this pre-incubation in solution, an aliquot of the lipocalin mutein/PCSK9 mixture was transferred to an ELISA plate coated with human LDL-R to measure the concentration of hPCSK9 that was not blocked to bind hLDL-R.

All incubation steps were performed with shaking at 300 rpm, and the plate was washed after each incubation step with 100 µl PBS-T buffer (PBS (Phosphate buffered saline), 0.05% Tween 20) for five times using a Biotek ELx405 select CW washer. In the first step, a 384-well fluorescence plate was coated with 20 µl of recombinant human LDL-R (R&D Systems, Cat. No. 2148-LD/CF) at a concentration of 5 µg/ml in PBS over night at 4° C. After washing, the LDL-R-coated wells were blocked with 100 µl PBS-T/BSA (2% BSA (Bovine serum albumin) in PBS containing 0.05% Tween 20) for 1 h at room temperature ("RT").

A fixed concentration of 25 nM human PCSK9 or of 0.25 nM human PCSK9_D374Y mutant was incubated in solution with (i) varying concentrations of SEQ ID NO: 3, SEQ ID NO: 4, SEQ ID NO: 6, SEQ ID NO: 7, SEQ ID NO: 8, or benchmark antibody of SEQ ID NO: 29 and SEQ ID NO: 33, or with (ii) SEQ ID NO: 2 as a negative control, using a starting concentration of 300 nM which was serially diluted at a 1:3 ratio down to 5 pM in PBS-T/BSA buffer. After 1 h incubation at room temperature, 20 µl of the reaction mixture was transferred to the LDL-R-coated ELISA plate to capture unbound (free) or non-competitively bound PCSK9 for 20 min at RT. To allow for transformation of ELISA readout results into free hPCSK9 concentrations (cf. below), a standard curve containing varying concentrations of hPCSK9 or hPCSK9_D374Y mutant starting with 25/50 nM (1:3 serially diluted in 11 steps) was prepared in PBS-T/BSA and incubated for 20 min on a MSD (MesoScaleDiscovery) plate as well.

To allow for detection and quantification of bound PCSK9, the residual supernatants were discarded and 20 µl mouse-anti-Flag M2-horseradish peroxidase ("HRP") (Sigma-Aldrich) was added in a 1:5000 dilution in PBS-T/BSA and incubated for 1 h at RT. After washing, 20 µl QuantaBlu Fluorogenic Peroxidase Substrate was added to each well and the fluorescence was measured at an excitation wavelength of 320 nm and an emission wavelength of 430 nM after 15 min using the GENios Plus plate reader (Tecan).

The evaluation was performed as follows: free hPCSK9 or the hPCSK9_D374Y mutant concentration c(hPCSK9)free/c(hPCSK9_D374Y)free was calculated from relative fluorescence signals using the standard curve determined in parallel and plotted versus the lipocalin mutein concentration, c(SEQ ID NO: 3, SEQ ID NO: 4, SEQ ID NO: 6, SEQ ID NO: 7, SEQ ID NO: 8, or benchmark antibody of SEQ ID NO: 29 and SEQ ID NO: 33). To obtain the lipocalin mutein concentration at which formation of the PCSK9/LDL-R complex was blocked by 50% (IC50), the curves were fitted by nonlinear regression with a single-site binding model according to c(PCSK9)free=c(PCSK9)tot(1+c(lipocalin mutein)IC50)), with the total tracer concentration c(PCSK9)tot and the IC50 value obtained above as free parameters. Curve fitting was performed using GraphPad Prism 4 software.

In summary, the negative control SEQ ID NO: 2 did not bind to PCSK9; in contrast, SEQ ID NO: 3, SEQ ID NO: 4, SEQ ID NO: 6, SEQ ID NO: 7 and SEQ ID NO: 8 showed strong competitive binding to hPCSK9 and hPCSK9_D374Y mutant, when competed against hLDL-R. The fitted IC50 values are shown in Table 2 below as well as in FIG. 2 (A and B). Competitive mode of action for the lipocalin muteins (SEQ ID NOs: 3, 4 and 6-9) was shown with both, wildtype and mutant PCSK9. The IC50 values in the competition ELISA using hPCSK9 are solely influenced by the fixed concentration of 25 nM. In the competition ELISA using 0.25 nM hPCSK9_D374Y mutant, IC50 values are affected by lipocalin muteins' affinity as well as by the fixed mutant concentration.

TABLE 2

| Molecule | hPCSK9 wt IC50 [nM] | hPCSK9_D374Y IC50 [nM] |
| --- | --- | --- |
| SEQ ID NO: 3 | 13.8 | 0.13 |
| SEQ ID NO: 4 | 6.2 | 0.37 |
| SEQ ID NO: 6 | 10.1 | 0.21 |

TABLE 2-continued

| Molecule | hPCSK9 wt IC50 [nM] | hPCSK9_D374Y IC50 [nM] |
| --- | --- | --- |
| SEQ ID NO: 7 | 13.2 | 0.13 |
| SEQ ID NO: 8 | 10.7 | 0.32 |

Example 8

Specificity and Species Crossreactivity of Representative Lipocalin Muteins to PCSK9

Specificity and species crossreactivity (FIGS. 3 (A-D)) of lipocalin muteins was assayed in a binding ELISA, the principle of which was as follows: Biotinylated ligands (human PCSK9, human PCSK9_D374Y, mouse PCSK9, and cynomolgus PCSK9) were captured on Neutravidin-coated ELISA plates and variable concentrations of lipocalin muteins were added. Bound lipocalin muteins were detected with rabbit anti-Streptag II antibody (GenScript, Cat. No. A00626) and HRP-labeled anti-rabbit-IgG antibody (Jackson ImmunoResearch, Cat. No. 211-035-109).

In the following detailed experimental protocol, incubation and washing steps were performed as described above in the competition ELISA protocol of Example 7. A 384-well plate suitable for fluorescence measurements (Greiner FLU-OTRAC™ 600, black flat bottom, high-binding) was coated with 20 ul of Neutravidin at a concentration of 5 µg/ml in PBS over night at 4° C. After washing, the Neutravidin-coated wells were blocked with 100 µl blocking buffer (PBS-T/BSA) for 1 h at room temperature. After washing again, 20 µl biotinylated ligand, either human PCSK9, human PCSK9_D374Y, mouse PCSK9 or cynomolgus PCSK9, at a concentration of 1 µg/ml in PBS-T/BSA was added for 1 h at room temperature. Excess ligand was removed by a further washing step.

Concentration of lipocalin mutein solutions was adjusted to 100 nM and then solutions were serially diluted at a 1:3 ratio down to 2 nM in PBS-T/BSA. A volume of 20 µl of the dilution was transferred to the 384-well plate and allowed to bind for 1 h at room temperature.

After incubation, the residual supernatants were discarded and 20 µl of the anti-StreptagII antibody in a 1:5.000 dilution in PBS-T/BSA was added and incubated for 1 h at room temperature. Supernatants were discarded again. To detect bound anti-Streptag II antibody, 20 µl of the mouse anti-rabbit IgG-HRP were added and incubated for 1 h at room temperature. After washing, 20 µl fluorogenic HRP substrate (Quantablue, Pierce) was added to each well, and the reaction was allowed to proceed for 15 min. The fluorescence intensity in relative fluorescence units (RFU) of every well on the plate was read using a Safire Microplate reader (Tecan). To obtain the lipocalin mutein concentration at which the maximum fluorescence signal is reached by 50% (EC50), the curves were fitted by nonlinear regression with a single-site binding model according to RFU=RFUmax·c(Lipocalin mutein)/(EC50+c(lipocalin mutein)), with the maximum relative fluorescenc RFUmax and the EC50 value as free parameters. Curve fitting was performed using GraphPad Prism 4 software.

In summary, binding of SEQ ID NO: 3, SEQ ID NO: 4, SEQ ID NO: 5, SEQ ID NO: 6, SEQ ID NO: 7, SEQ ID NO: 8 and SEQ ID NO: 9 to human PCSK9, human PCSK9_D374Y mutant, mouse PCSK9 and cynomolgus PCKS9 could be detected, whereas negative control SEQ ID NO: 2 showed no binding to any of these targets. The fitted EC50 values are shown in Table 3 below. The EC50 values for human PCSK9 and cynomolgus PCSK9 are comparable, showing that the lipocalin muteins are fully crossreactive with cynomolgus monkey PCSK9. Affinities to mouse PCSK9 are similar or up to 10-fold lower while EC50 values for human PCSK9_D374Y mutant are similar to those obtained for human PCSK9.

TABLE 3

| Molecule | hPCSK9 EC50 [nM] | hPCSK9 D374Y EC50 [nM] | mPCSK9 EC50 [nM] | cPCSK9 EC50 [nM] |
|---|---|---|---|---|
| SEQ ID NO: 3 | 1.6 | 1.2 | 4.4 | 1.8 |
| SEQ ID NO: 4 | 2.4 | 1.6 | 21.8 | 2.9 |
| SEQ ID NO: 5 | 5.1 | 2.9 | 30 | 5.7 |
| SEQ ID NO: 6 | 3.1 | 2.1 | 20.1 | 3.7 |
| SEQ ID NO: 7 | 2.8 | 0.8 | 16.3 | 3.8 |
| SEQ ID NO: 8 | 4.4 | 1.4 | 10.1 | 6.1 |
| SEQ ID NO: 9 | 5.6 | 1.1 | 16.2 | 8.4 |

Example 9

Lipocalin Mutein Mediated Restorage of Downregulation of DiI-Labeled LDL Uptake in a Cell-based Assay A cell-based assay was employed to demonstrate the ability of PCSK9-binding lipocalin muteins (SEQ NO: 3, SEQ NO: 4, SEQ NO: 6, SEQ NO: 7 and SEQ NO: 8) to neutralize the PCSK9-mediated reduction of number of surface LDL-R molecules and in consequence restore downregulated LDL uptake in HepG2 cells. SEQ ID NO: 2 served as negative control.

In this regard, HepG2 cells were plated in a 96-well poly-d-lysine-coated plate (Greiner, 955946) at a density of 60,000 cells/well in 100 µl/well DMEM (PAN P04-04510) containing 10% FCS (Fetal calf serum). After 24 h the medium was switched to DMEM containing 1% FCS (100 µl/well). After 18 h the medium was removed and switched (without washing step) to 50 µl DMEM containing 20 µg/ml LDL-Bodipy® FL (Invitrogen, L3483) but without FCS. Serial 1:2 dilution of lipocalin muteins starting at a concentration of 4000 nM was performed. One dilution series was prepared in DMEM containing 15 µg/ml PCSK9 and another one, as a control, in pure DMEM. Lipocalin muteins and PCSK9 were preincubated for 30 min. at room temperature and then 50 µl was added to the cells resulting in a final PCSK9 concentration of 100 nM. Total sample volume on the plate was 100 µl and all samples were measured in 5× replicates. Cells in DMEM without LDL and PCSK9, DMEM with LDL and PCSK9, and DMEM with LDL but without PCSK9 were used as controls.

Plates with samples were incubated at 37° C. for 6 h before cells were washed with PBS. Wells were filled with 100 µl PBS and fluorescence of cells was read at 485/535 nm using a BMG PheraStar reader.

To determine IC50 values the highest and the lowest value of the 5 replicates were excluded and the mean and standard deviation for each remaining data point was calculated. The curves were fitted by GraphPad Prism 4 using nonlinear regression "sigmoidal dose response, variable slope" model (5PL fit). Data were normalized by the value of stimulated and non-stimulated cells (cells with/without PCSK9). The fitted curves are shown in FIG. 4 and calculated IC50 values are summarized in Table 4 below.

TABLE 4

| Molecule | IC50 [nM] |
|---|---|
| SEQ ID NO: 3 | 71.8 |
| SEQ ID NO: 4 | 85.8 |
| SEQ ID NO: 6 | 44.5 |
| SEQ ID NO: 7 | 95.8 |
| SEQ ID NO: 8 | 81.2 |

Example 10

Affinity of Additional Lipocalin Muteins to PCSK9

To measure the binding affinity of additional lipocalin muteins to biotinylated human PCSK9 (hPCSK9-Bio), a Surface Plasmon Resonance (SPR) based assay was employed utilizing a Biacore T200 instrument (GE Healthcare). For the SPR affinity assay (FIG. 5 (A-C)), the Biotin CAPture Kit (GE Healthcare) was used.

In each measurement, cycle Biotin CAPture Reagent (GE Healthcare) was applied to the reference and measurement channels of Sensor Chip CAP (GE Healthcare) for 5 min at a flow rate of 2 µl/min. hPCSK9-Bio at a concentration of 1 µg/ml was injected on the measurement channel for 2 min at a flow rate of 10 µl/min. To determine the affinity, three to four dilutions of lipocalin muteins of SEQ ID NOs: 13-28 (see Table 5) were prepared in HBS-EP+ buffer and applied to the chip surface, using concentrations of 128, 32, 8 and 2 nM for said muteins. The binding assay was carried out with a contact time of 3 min, dissociation time of 15 min and applying a flow rate of 30 µl/min. All measurements were performed at 25° C. Regeneration of the Sensor Chip CAP surface was achieved with an injection of 6 M guanidine-HCl with 0.25 M NaOH (2 min) followed by an extra wash with running buffer and a stabilization period of 2 min. Prior to the measurements, one conditioning cycle consisting of three consecutive regeneration steps was performed. Data were evaluated with Biacore T200 Evaluation software (V 1.0). Double referencing was used. The 1:1 binding model was used to fit the raw data.

Figure 5:
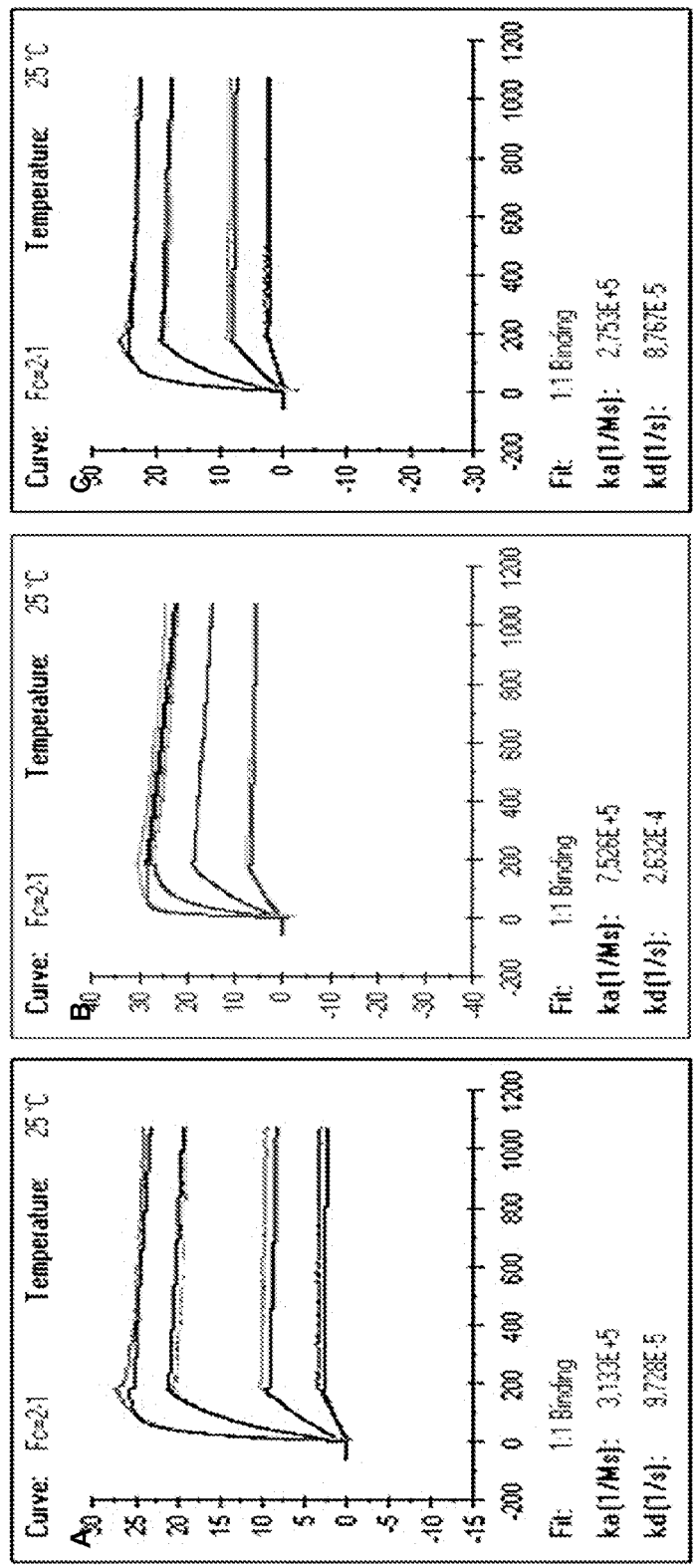

The resulting fit curves for some of the lipocalin muteins are shown in FIG. 5. Namely, SEQ ID NO: 13 (FIG. 5C), SEQ ID NO: 20 (FIG. 5A), and SEQ ID NO: 22 (FIG. 5B) bound with high affinity to human PCSK9. Association rate constants $k_a$ or $k_{on}$, dissociation rate constants $k_d$ or $k_{off}$ and resulting dissociation constants $K_D$ for all muteins are summarized in Table 5.

TABLE 5

| Molecule | $k_{on}$ [M$^{-1}$*s$^{-1}$] | $k_{off}$ [s$^{-1}$] | $K_D$ [nM] |
|---|---|---|---|
| SEQ ID NO: 13 | 2.75E+05 | 8.77E−05 | 0.32 |
| SEQ ID NO: 14 | 2.56E+05 | 1.05E−04 | 0.41 |
| SEQ ID NO: 15 | 2.78E+05 | 1.07E−04 | 0.38 |
| SEQ ID NO: 16 | 2.55E+05 | 1.29E−04 | 0.51 |
| SEQ ID NO: 17 | 2.49E+05 | 1.11E−04 | 0.45 |
| SEQ ID NO: 18 | 3.13E+05 | 1.11E−04 | 0.35 |
| SEQ ID NO: 19 | 2.47E+05 | 1.32E−04 | 0.53 |
| SEQ ID NO: 20 | 3.13E+05 | 9.73E−05 | 0.31 |
| SEQ ID NO: 21 | 2.45E+05 | 1.37E−04 | 0.56 |
| SEQ ID NO: 22 | 7.53E+05 | 2.63E−04 | 0.35 |
| SEQ ID NO: 23 | 8.36E+05 | 1.76E−04 | 0.21 |
| SEQ ID NO: 24 | 3.67E+05 | 1.15E−04 | 0.31 |
| SEQ ID NO: 25 | 4.36E+05 | 1.05E−04 | 0.24 |
| SEQ ID NO: 26 | 6.68E+05 | 2.30E−04 | 0.34 |
| SEQ ID NO: 27 | 7.34E+05 | 3.10E−04 | 0.42 |
| SEQ ID NO: 28 | 6.84E+05 | 1.98E−04 | 0.29 |

Example 11

Species Crossreactivity of Additional Lipocalin Muteins to PCSK9

To measure the binding affinity of the lipocalin muteins SEQ ID NO: 13, SEQ ID NO: 20 and SEQ ID NO: 22 to biotinylated human, cynomolgus monkey and mouse PCSK9, a Surface Plasmon Resonance (SPR) based assay was employed utilizing a Biacore T200 instrument (GE Healthcare). For the SPR affinity assay (FIG. 6 (A-C)), the Biotin CAPture Kit (GE Healthcare) was used.

In the following experimental protocol, capture, sample binding and regeneration steps as well as data evaluation were performed as described above in Example 10. To determine the affinity, four dilutions of said muteins were prepared in HBS-EP+ buffer and applied to the chip surface, using concentrations of 128, 32, 8 and 2 nM, respectively.

Figure 6:
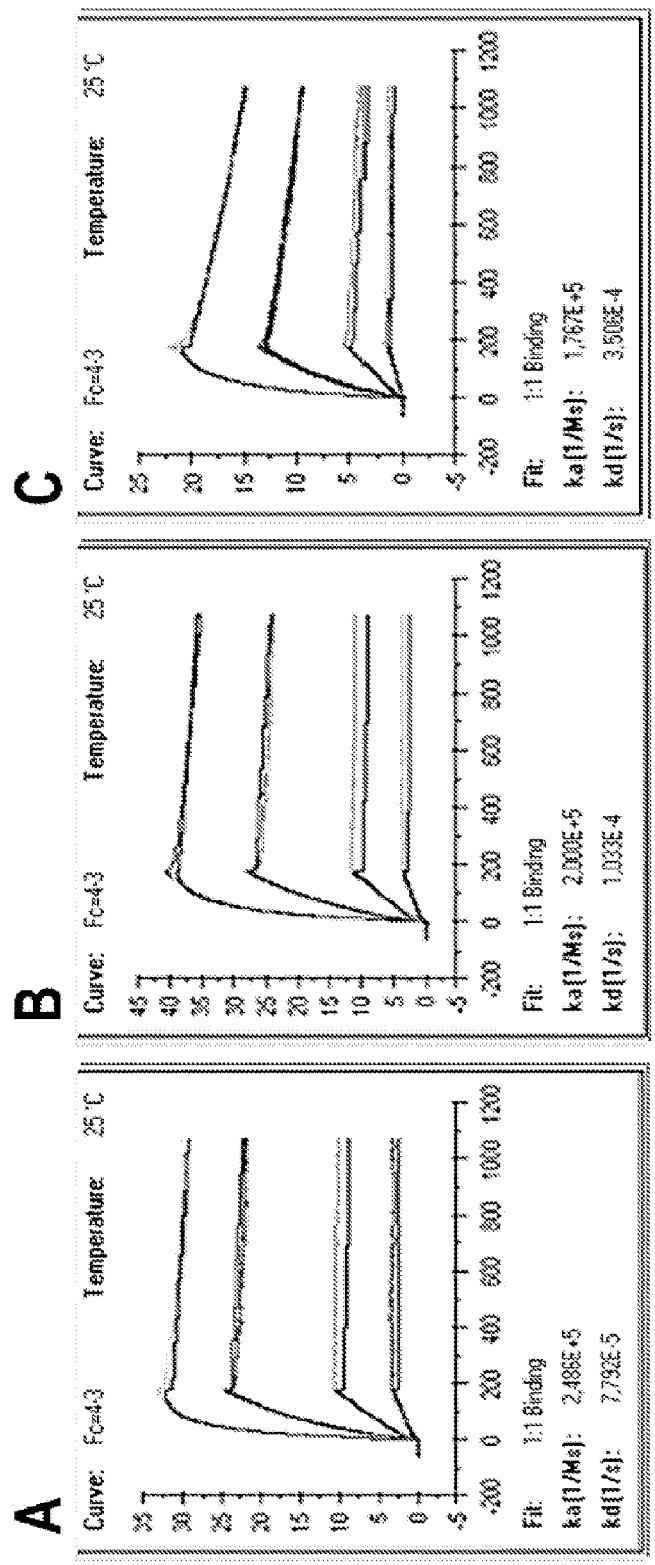

The resulting fit curves for SEQ ID NO: 20 are shown in FIG. 6. The data show that SEQ ID NO: 20 bound with high affinity to human PCSK9 (FIG. 6A) and to cynomolgus monkey PCSK9 (FIG. 6B). Affinity to mouse PCSK9 (FIG. 6C) is lower. Association rate constants $k_a$ or $k_{on}$, dissociation rate constants $k_d$ or $k_{off}$ and resulting dissociation constants $K_D$ are summarized in Table 6 below.

TABLE 6

| Ligand | Molecule | $k_{on}$ [M−1*s−1] | $k_{off}$ [s−1] | $K_D$ [nM] |
|---|---|---|---|---|
| human PCSK9 | SEQ ID NO: 13 | 2.62E+05 | 8.31E−05 | 0.32 |
| cyno PCSK9 | SEQ ID NO: 13 | 2.16E+05 | 9.40E−05 | 0.44 |
| mouse PCSK9 | SEQ ID NO: 13 | 1.76E+05 | 3.12E−04 | 1.77 |
| human PCSK9 | SEQ ID NO: 20 | 2.49E+05 | 7.79E−05 | 0.31 |
| cyno PCSK9 | SEQ ID NO: 20 | 2.00E+05 | 1.03E−04 | 0.52 |
| mouse PCSK9 | SEQ ID NO: 20 | 1.77E+05 | 3.51E−04 | 1.98 |
| human PCSK9 | SEQ ID NO: 22 | 6.63E+05 | 2.58E−04 | 0.39 |
| cyno PCSK9 | SEQ ID NO: 22 | 3.86E+05 | 2.76E−04 | 0.71 |
| mouse PCSK9 | SEQ ID NO: 22 | 3.21E+05 | 6.38E−04 | 1.99 |

Example 12

Binding of Additional Lipocalin Muteins to PCSK9 in Solution

Binding of lipocalin muteins and PEGylated variants thereof (here, with branched PEG40), to biotinylated human PCSK9 (hPCSK9-Bio) in solution was tested in vitro using a competition electrochemiluminescence (ECL) assay format (FIG. 7). In this experiment, a constant concentration of hPCSK9-Bio was incubated for 1 h with variable concentrations of lipocalin muteins SEQ ID NO: 13, SEQ ID NO: 20, and SEQ ID NO: 22 as well as the PEGylated variants SEQ ID NO: 30, SEQ ID NO: 31 and SEQ ID NO: 32. After this pre-incubation in solution, an aliquot of the lipocalin mutein/PCSK9 mixture was transferred to an ECL plate coated with a monoclonal benchmark antibody (comprising the light chain of SEQ ID NO: 29 and the heavy chain of SEQ ID NO: 33) to measure the concentration of hPCSK9 that was not blocked by the lipocalin muteins (PEGylated as well as non-PEGylated forms) and therefore could still be bound by the antibody (FIG. 7). Competitive mode of action for those lipocalin muteins was shown with hPCSK9-Bio.

All incubation steps were performed with shaking at 300 rpm, and the plate was washed after each incubation step with 80 μl PBS-T buffer (PBS, 0.05% Tween 20) for five times using a Biotek EL×405 select CW washer. In the first step, a 384-well MSD plate was coated with 20 μl of the benchmark antibody at a concentration of 5 μg/ml in PBS over night at 4° C. After washing, the LDL-R-coated wells were blocked with 60 μl PBS-T/BSA (2% BSA in PBS containing 0.05% Tween 20) for 1 h at room temperature.

A fixed concentration of 10 μM hPCSK9-Bio was incubated in solution with varying concentrations of said muteins, using a starting concentration of 100 nM which was serially diluted at a 1:3 ratio down to 1.7 μM in PBS-T/BSA buffer. After 1 h of incubation at room temperature, 20 μl of the reaction mixture were transferred to the antibody-coated ELISA plate to capture unbound (free) PCSK9 for 20 min at room temperature. To allow for transformation of ELISA readout results into free hPCSK9 concentrations (cf. detection and quantification of bound hPCSK9-Bio below), a standard curve containing varying concentrations of hPCSK9-Bio starting with 10 nM (1:3 serially diluted in 11 steps) was prepared in PBS-T/BSA and incubated for 20 min on a MSD plate (MesoScaleDiscovery).

To allow for detection and quantification of bound hPCSK9-Bio, the residual supernatants were discarded and 20 μl Sulfo-Tag-labeled Streptavidin (Meso Scale Discovery) was added at a concentration of 1 μ/ml in PBS-T/BSA and incubated for 1 h at room temperature. After washing, 35 μl 2×MSD read buffer with surfactant (Meso Scale Discovery) was added to each well and electrochemiluminescence (ECL) signals were measured within 15 min using the SECTOR Imager 2400 (Meso Scale Discovery).

The evaluation was performed as follows: free PCSK9 concentration $c(PCSK9)_{free}$ was calculated from ECL signals using the standard curve determined in parallel and plotted versus lipocalin mutein concentration, c(lipocalin mutein). To obtain the lipocalin mutein concentration at which formation of the PCSK9/benchmark antibody complex was blocked by 50% (IC50), the curves were fitted by nonlinear regression with a single-site binding model according to $c(PCSK9)_{free} = c(PCSK9)_{tot}(1+c(\text{lipocalin mutein})IC50))$, with the total tracer concentration $c(PCSK9)_{tot}$ and the IC50 value as free parameters. Curve fitting was performed using GraphPad Prism 4 software.

In summary, lipocalin muteins SEQ ID NO: 13, SEQ ID NO: 20 and SEQ ID NO: 22 as well as the PEGylated variants SEQ ID NO: 30, SEQ ID NO: 31 and SEQ ID NO: 32 showed strong competitive binding to hPCSK9-Bio, when competed against the benchmark antibody (comprising SEQ ID NOs: 29 and 33). The fitted IC50 values are summarized in Table 7 below.

TABLE 7

| Molecule | IC50 [nM] |
|---|---|
| SEQ ID NO: 13 | 0.16 |
| SEQ ID NO: 20 | 0.11 |
| SEQ ID NO: 22 | 0.09 |
| SEQ ID NO: 30 | 0.19 |
| SEQ ID NO: 31 | 0.53 |
| SEQ ID NO: 32 | 0.37 |

Example 13

Inhibition of PCSK9-mediated Downregulation of LDL-R by Additional Lipocalin Muteins Human PCSK9 induces LDL-R internalization and therefore the depletion of LDL-R from the cell surface. Expression of LDL-R was assessed in this assay in presence of lipocalin muteins referred in Example 12 (PEGylated (here, with branched PEG40) as well as non-PEGylated forms) to determine the lipocalin muteins' potency to inhibit PCSK9's activity in mediating LDL-R cell surface depletion, while SEQ ID NO: 2 was used as a negative control.

HEPG2 cells (10,000 cells/wells) were allowed to attach 24 h in 384-well MSD (Mesoscale Discovery) plate precoated with 100 µg/ml poly-d-lysine. Full medium (DMEM containing 1 mg/ml G418 and 10% FBS) was then switched to either DMEM lacking serum or containing 10% lipoprotein-deficient serum to allow maximal expression of LDL-R on the cell surface. Cells were then washed with PBS and dilution series of lipocalin muteins in the presence of 100 nM PCSK9 were incubated at 37° C. for 6 h. The mixture was then discarded by gently tapping out and fixation of the cells was then performed by addition of Roti®-Histofix at room temperature for 20 min. Cells were washed twice with PBS and incubated overnight at 4° C. with blocking buffer (PBSFCS 4% BSA 2%). Buffer was gently discarded and a mix of 1 µg/ml of a goat anti-hLDL-R(R&D systems, Cat. No. AF2148) and 2 µg/ml of a donkey anti-goat-Sulfotag (MSD, Cat. No. R32AG-1) in blocking buffer was incubated at room temperature for 1 h. Cells were then gently twice washed with PBS and Surfactant free reading buffer (MSD) was added. ECL signals were measured using the SECTOR Imager 2400 (MSD). The evaluation was performed as follows: ECL signals were transformed by setting the signals measured for PCSK9 activity in the absence of competitor (here, lipocalin mutein) to 100% PCSK9 activity. Data were fitted with a sigmoidal dose-response model with shared slope using GraphPad Prism 4 software (FIG. 8). Resulting IC50 and IC90 values are summarized in Table 8 below.

TABLE 8

| Molecule | IC50 [nM] | IC90 [nM] |
|---|---|---|
| SEQ ID NO: 13 | 103.3 | 216.1 |
| SEQ ID NO: 20 | 91.7 | 192.0 |
| SEQ ID NO: 22 | 76.9 | 160.9 |
| SEQ ID NO: 30 | 82.6 | 172.8 |
| SEQ ID NO: 31 | 82.6 | 172.8 |
| SEQ ID NO: 32 | 70.7 | 147.8 |

Example 14

Generation of Thermo-stabilized PCSK9-specific Lipocalin Muteins by Positional Saturation Mutagenesis For improvement of thermal stability of PCSK9-specific muteins, lipocalin mutein of SEQ ID NO: 13 was mutated at positions 79 and 105 (as shown in FIG. 14). Libraries of thermo-stabilized derivatives of SEQ ID NO: 13 were generated in a manner that led to saturated randomization of the mentioned positions either on their own or in combination with the use of recursive assembly of NNK oligonucleotides in a polymerase chain reaction (see, for example, WO2007/107563). For the same purpose, lipocalin mutein of SEQ ID NO: 22 was mutated at position 92 from Histidine to Proline (as shown in FIG. 14).

Example 15

Identification of Thermo-stabilized PCSK9-specific Muteins by screening

The mutagenized central cassette of the libraries preparation obtained after PCR assembly, as described in Example 14, was inserted into a vector which allowed bacterial production of the lipocalin muteins under the control of a tetracyclin promoter (as described Example 5).

For affinity ranking of the optimized lipocalin muteins, anti-Strep-tag antibody (IBA, Goettingen) diluted in PBS was coated on microtiterplates and 20 µl of BSA-blocked cultures were added, which allowed specific capture of lipocalin muteins on the plate. Different concentrations (0.5-5 nM) of biotinylated PCSK9 proteins were added and specifically-bound PCSK9 proteins were detected with extravidin-HRP (Sigma Aldrich, St. Louis, Mo.) after extensive washing. For quantification, 20 µl QuantaBlu was added and measured at an excitation wavelength of 320 nm and an emission wavelength of 430 nm.

Selection of thermo-stabilized lipocalin muteins was performed in the same way as described above with the only difference that bacterial extracts containing lipocalin muteins were heated up to 65° C. for 30 min prior to incubation with the PCSK9 target. Those muteins that showed unaffected binding signals after heating step compared to the non-heated samples were selected for sequencing.

Example 16

Measurement of Melting Temperatures of Optimized PCSK9-specific Muteins

To determine melting temperatures of PCSK9-specific muteins, samples at a protein concentration of 1 mg/ml in PBS (Gibco) were scanned (25-100° C.) at 1 C/min using a capillary nanoDSC instrument (Q2000, TA Instruments). The integrated software calculated the melting temperature (Tm) from the displayed thermogram.

The resulting melting temperatures for the two lipcalin muteins (SEQ ID NO: 22 and SEQ ID NO: 13) together with the optimized derivatives therefrom (SEQ ID NOs: 62-71) are summarized in Table 9 below. For example, the data shows that Tms of SEQ ID NO: 63, SEQ ID NO: 64 and SEQ ID NO: 65 were significantly higher compared to SEQ ID NO: 13 and the onset of melting was shifted by up to 13° C. (FIG. 12).

TABLE 9

| SEQ ID | Tm [° C.] nanoDSC | onset of melting [° C.] |
|---|---|---|
| SEQ ID NO: 13 | 61 | 49 |
| SEQ ID NO: 65 | 72.8 | 62 |
| SEQ ID NO: 64 | 63.8 | 54 |
| SEQ ID NO: 66 | 69 | 53 |
| SEQ ID NO: 67 | 67.8 | 53 |
| SEQ ID NO: 68 | 65.1 | 55 |
| SEQ ID NO: 63 | 68.3 | 57 |
| SEQ ID NO: 69 | 63.7 | 55 |
| SEQ ID NO: 70 | 59.1 | 54 |
| SEQ ID NO: 71 | 65 | 56 |
| SEQ ID NO: 22 | 56 | 52 |
| SEQ ID NO: 62 | 59 | 53 |

Example 17

Affinity of Optimized Lipocalin Derivatives to PCSK9

To measure the binding affinity to biotinylated human PCSK9 of a representative group of lipocalin muteins, a Surface Plasmon Resonance (SPR) based assay was employed utilizing a Biacore T200 instrument (GE Healthcare). For the SPR affinity assay, the Biotin CAPture Kit (GE Healthcare) was used.

In each measurement cycle, Biotin CAPture Reagent (GE Healthcare) was applied to the reference and measurement channels of Sensor Chip CAP (GE Healthcare) for 5 min at a flow rate of 2 µl/min. Biotinylated PCSK9 at a concentration of 4 µg/ml was injected on the measurement channel for 2 min at a flow rate of 10 µl/min. To determine the affinity, three to four dilutions of SEQ ID NOs: 62-71 were prepared in HBS-EP+ (0.01 M HEPES pH 7.4, 0.15 M NaCl, 3 mM EDTA, 0.005% Surfactant P20) buffer and applied to the chip surface, using final concentrations of 128 nM, 32 nM, 8 nM and 4 nM. The binding assay was carried out with a contact time of 3 min, dissociation time of 20 min and applying a flow rate of 30 µl/min. All measurements were performed at 25° C. Regeneration of the Sensor Chip CAP surface was achieved with an injection of 6 M guanidine-HCl with 0.25 M NaOH (2 min) followed by an extra wash with running buffer and a stabilization period of 2 min. Prior to the measurements, one conditioning cycle consisting of three consecutive regeneration steps was performed. Data were evaluated with Biacore T200 Evaluation software (V 1.0). Double referencing was used. The 1:1 binding model was used to fit the raw data.

Figure 13:
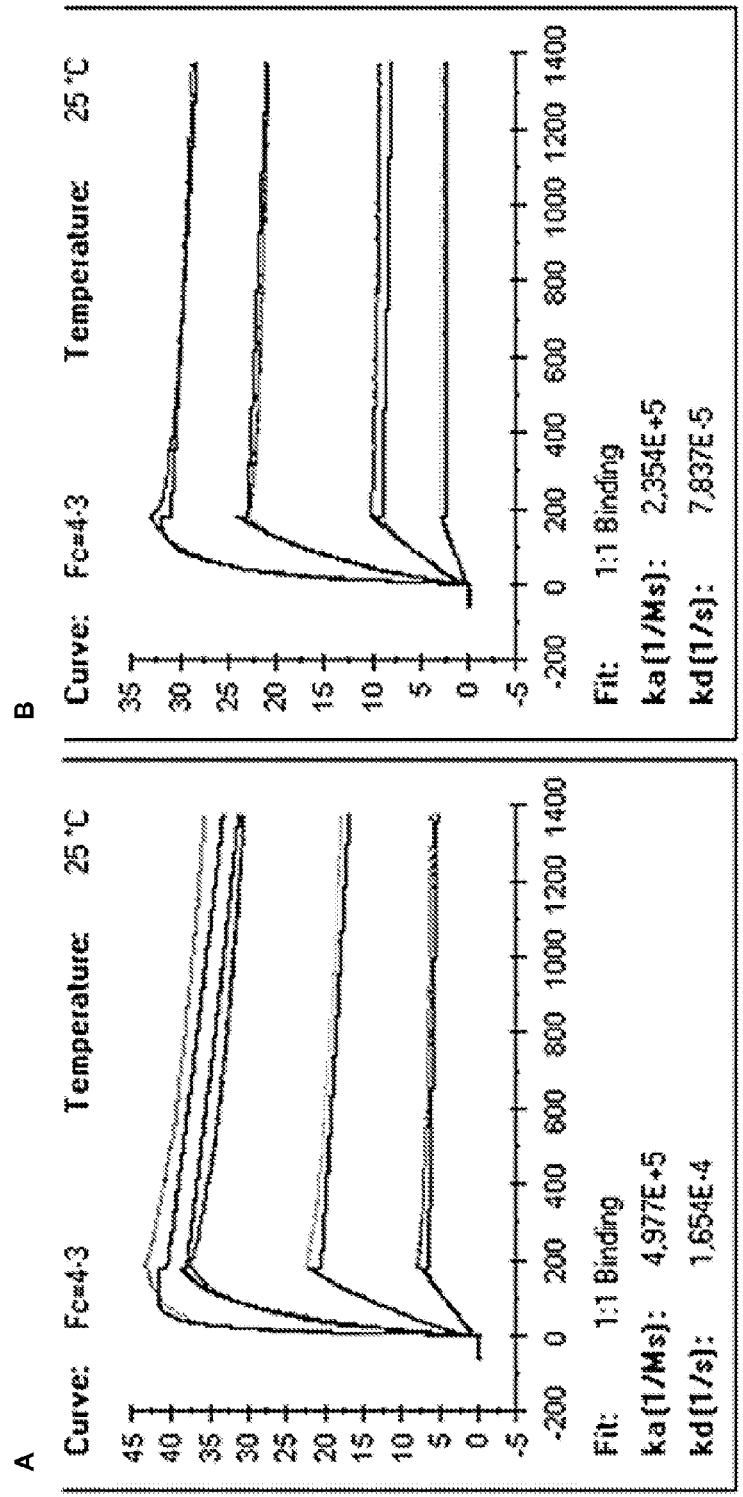
Figure 13:
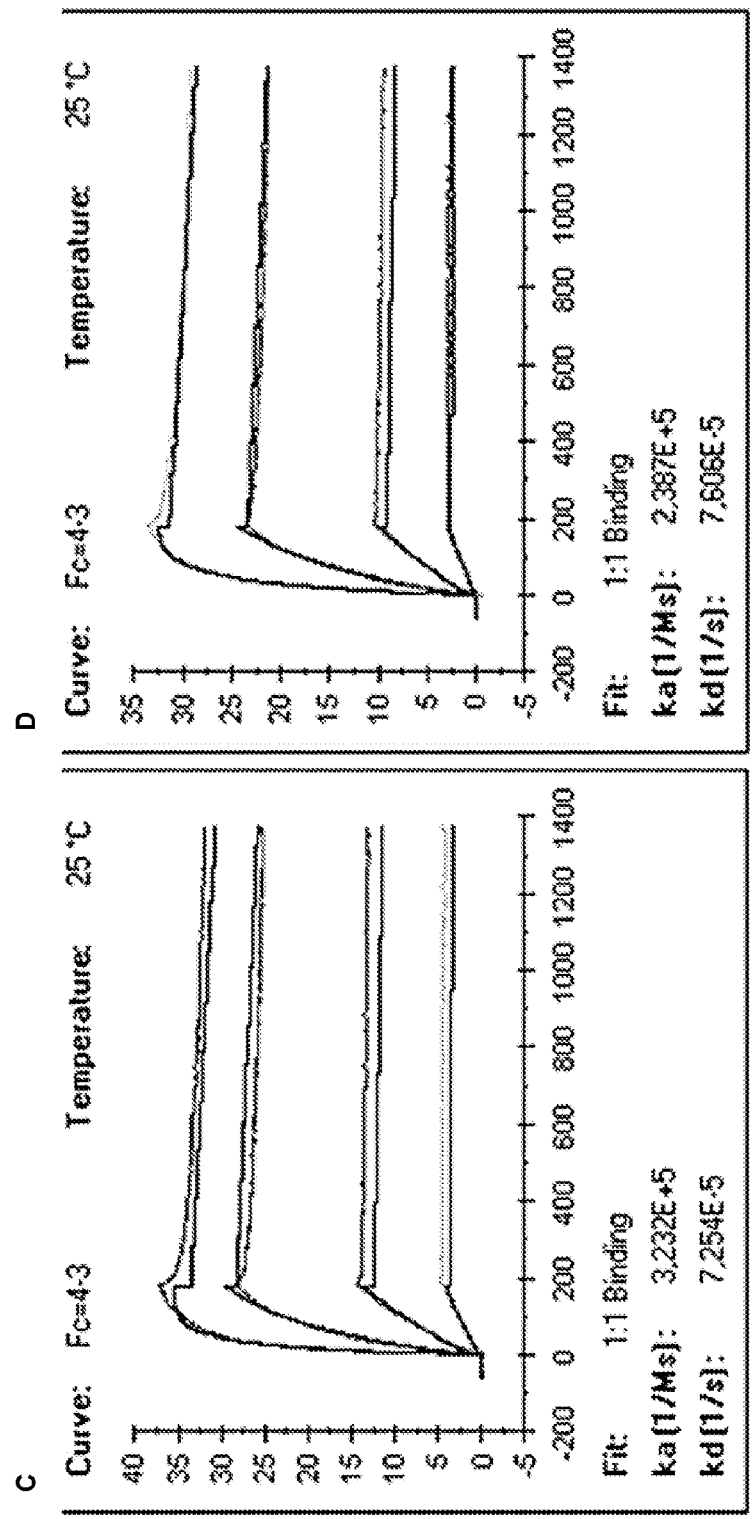
Figure 13:
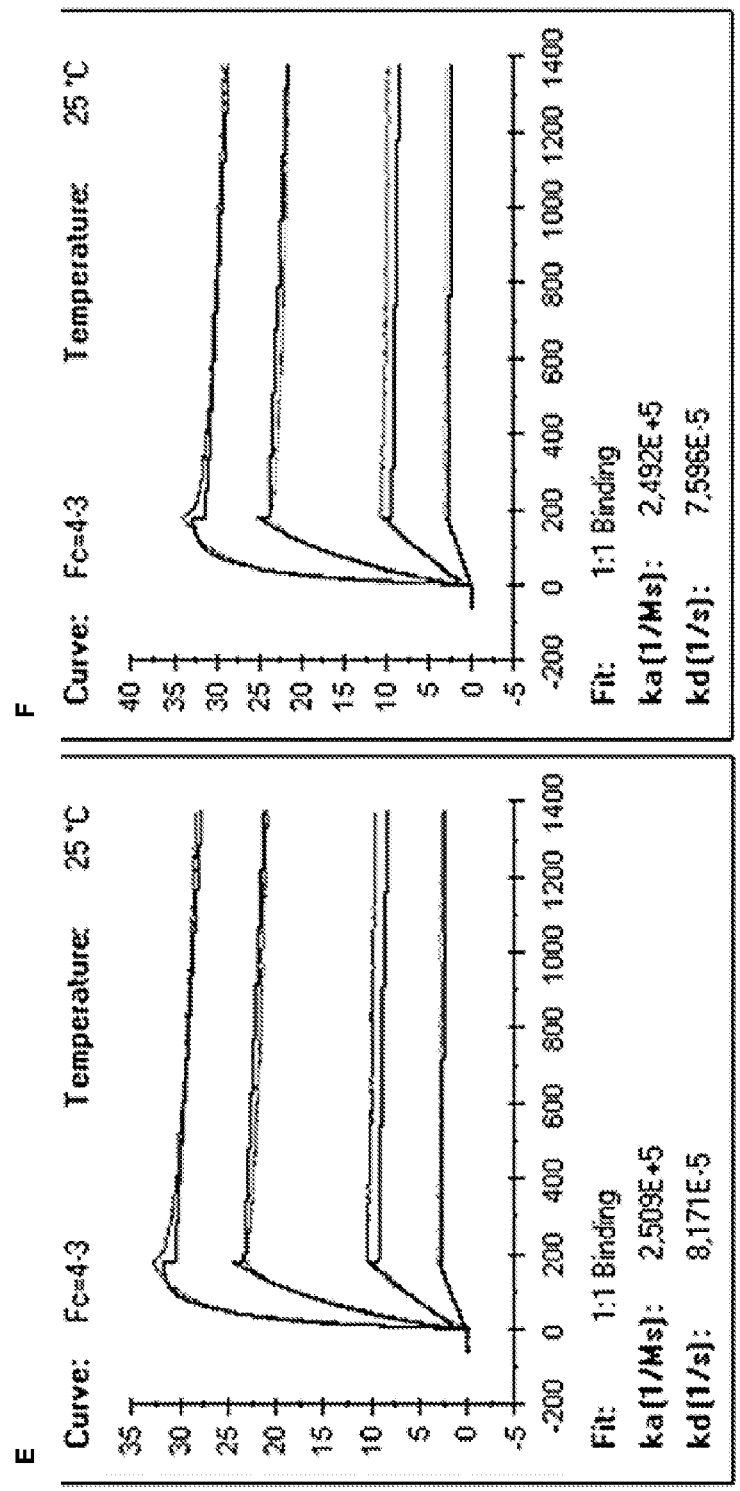
Figure 13:
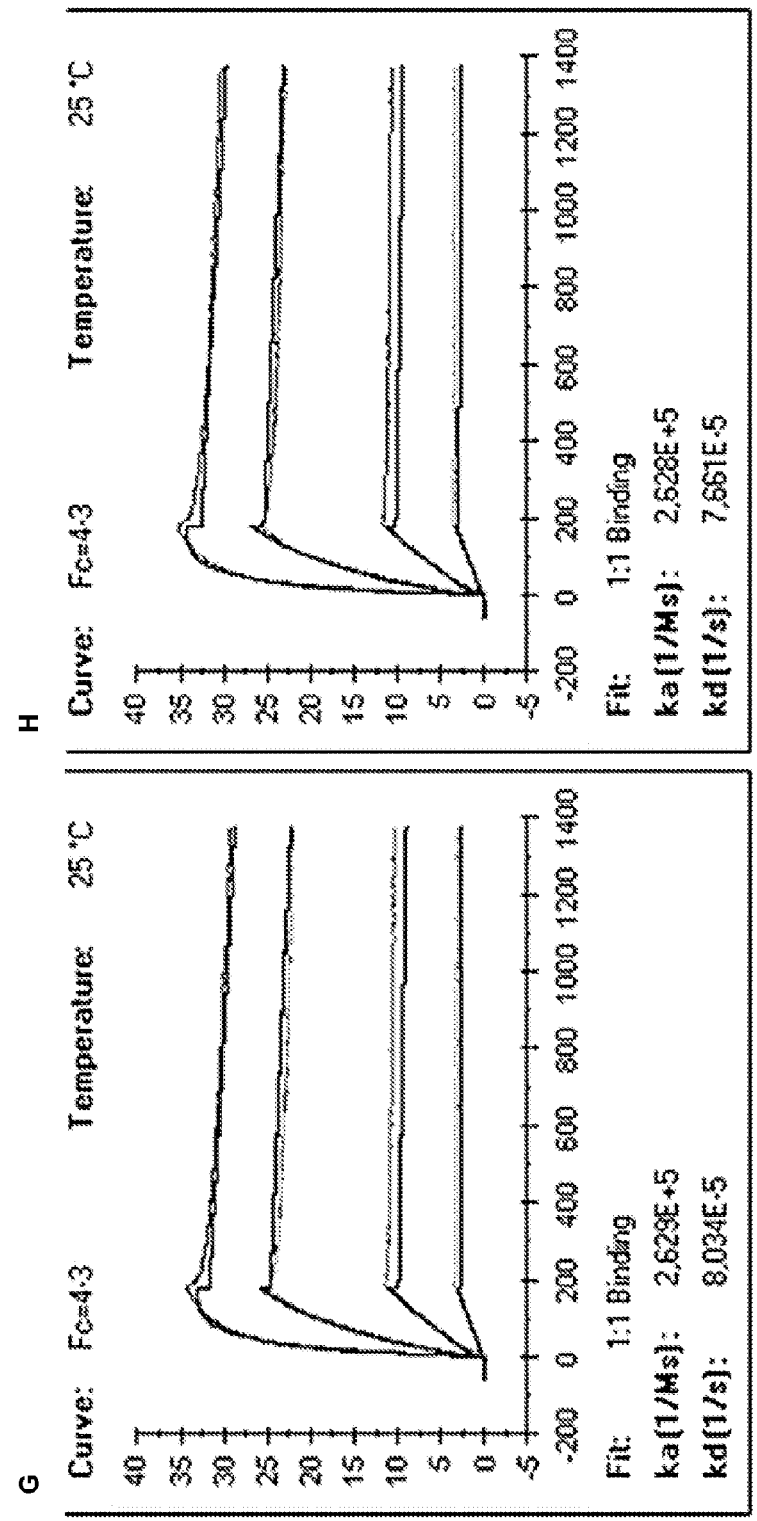
Figure 13:
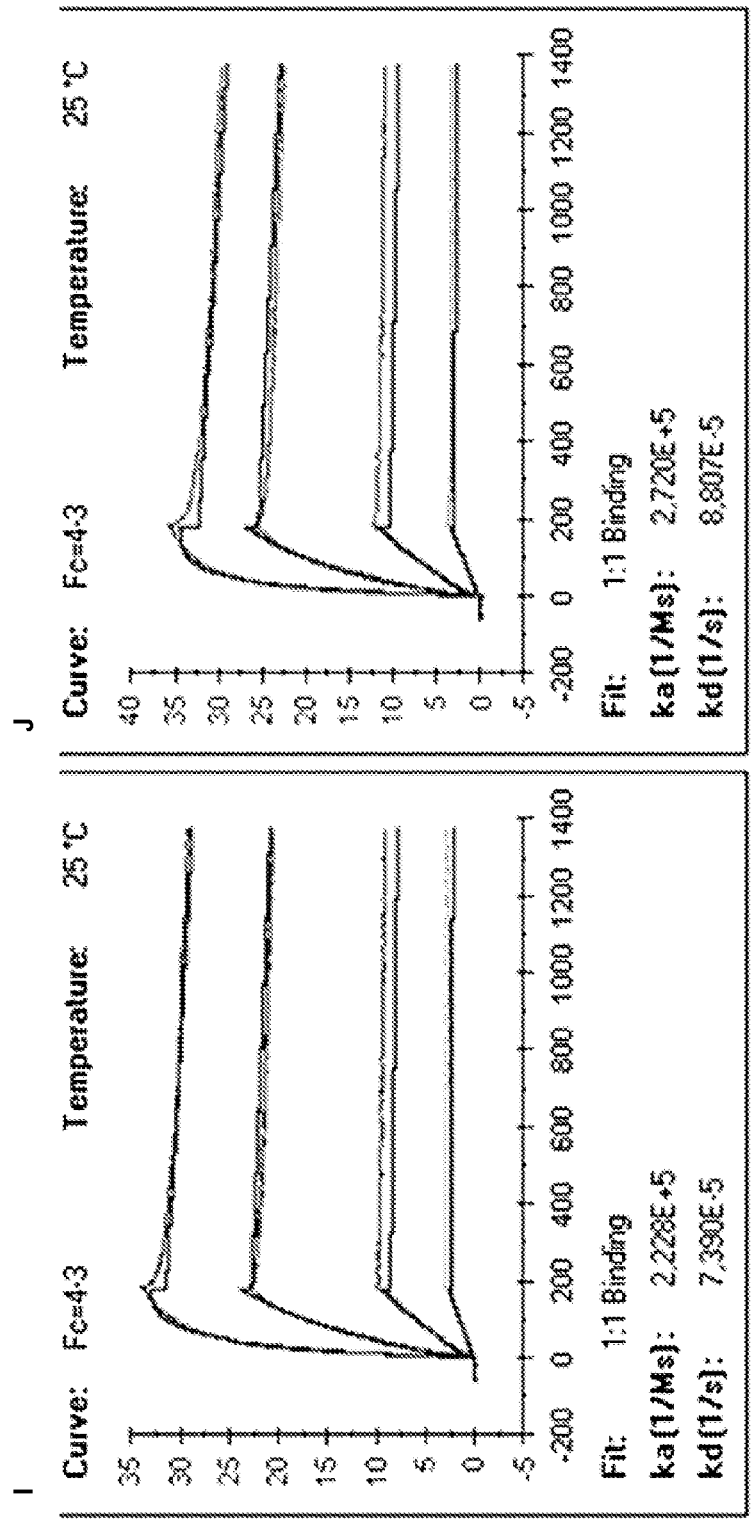

The resulting fit curves for lipocalin muteins of SEQ ID NOs: 62-71 are shown in FIG. 13 (A-J), respectively. The data shows that affinities of thermo-stabilized lipocalin muteins (SEQ ID NOs: 62-71) are fully retained compared to lipocalin muteins of SEQ ID NO: 13 and SEQ ID NO: 22. Association rate constants $k_a$ or $k_{on}$ while dissociation rate constants $k_d$ or $k_{off}$. The resulting dissociation constants $K_D$ for said lipocalin muteins are summarized in Table 10 below.

TABLE 10

| SEQ ID | kon [M−1*s−1] | koff [s−1] | KD [nM] |
|---|---|---|---|
| SEQ ID NO: 13 | 2.81E+05 | 6.84E−05 | 0.24 |
| SEQ ID NO: 65 | 2.39E+05 | 7.61E−05 | 0.32 |
| SEQ ID NO: 64 | 3.23E+05 | 7.25E−05 | 0.22 |
| SEQ ID NO: 66 | 2.51E+05 | 8.17E−05 | 0.33 |
| SEQ ID NO: 67 | 2.49E+05 | 7.60E−05 | 0.31 |
| SEQ ID NO: 68 | 2.63E+05 | 8.03E−05 | 0.31 |
| SEQ ID NO: 63 | 2.35E+05 | 7.84E−05 | 0.33 |
| SEQ ID NO: 69 | 2.63E+05 | 7.66E−05 | 0.29 |
| SEQ ID NO: 70 | 2.23E+05 | 7.39E−05 | 0.33 |
| SEQ ID NO: 71 | 2.72E+05 | 8.81E−05 | 0.32 |
| SEQ ID NO: 22 | 5.91E+05 | 2.19E−04 | 0.37 |
| SEQ ID NO: 62 | 4.98E+05 | 1.65E−04 | 0.33 |

Example 18

Production of PCSK9-specific Tlc Muteins in *E. Coli*

PCSK9-specific lipocalin muteins (SEQ ID NOs: 62, 82, 83 and 84) were expressed in *E. coli*. DNA encoding each lipocalin mutein (SEQ ID NOs: 86, 87, 88 and 89, respectively) was inserted into a likewise-cut vector which allowed bacterial production of the muteins under the control of a T5 promoter (in case of SEQ ID NOs: 62, 82 and 84) or a T7A3 promoter (in case of SEQ ID NO: 83). The Muteins were purified from cell lysates by combination of column chromatography methods using anion exchange column, phenyl sepharose column, gel filtration column and chelating column (in the case of SEQ ID NOs: 82 and 84). The purified muteins were finally solubilized in PBS.

Example 19

Biacore Analysis

All procedures were performed with Biacore T200 (GE Healthcare) at 25° C. A HBS-EP+ buffer (10 mM HEPES, pH 7.4, 0.15 M NaCl, 3 mM EDTA, and 0.05% surfactant P20) was used as running buffer. A biotinylation of PCSK9 protein was performed in a general manner using a labeling reagent, EZ-Link Sulfo-NHS-LC-LC-Biotin (Thermo Scientific), and the unreacted reagents were removed by desalting spin columns. A Biotin CAPture kit (GE Healthcare) was used to immobilize the biotinylated PCSK9 ligand to sensor chips. Flowcells on the CAP sensor chips, pre-immobilized with a ss-DNA oligo, were hybridized with a complementary ss-DNA oligo conjugated with streptavidin, and followed by a biotinylated ligand injection.

For capture experiments, streptavidin-DNA conjugates were injected to two flowcells for 20 sec; and the biotinylated PCSK9 samples were diluted to 1 ng/µl in the running buffer and then injected to one flowcell for 1 min at 10 µl/min, whereas another flowcell was left without captured samples to provide a reference surface. The capture protocol was designed to yield capture levels of ligand samples that resulted in Rmax values no greater than 20 RU.

For each kinetic experiment, varying concentrations of purified PCSK9-specific lipocalin muteins ranging from 0.03 nM to 100 nM were prepared as the analytes, and injected for 300 sec at 30 µl/min followed by 30 min of dissociation. Captured and reference surfaces were regenerated with a 2 min pulse of 6 M guanidine hydrochloride in 0.25 M sodium hydroxide.

The dissociation constants (KDs) were calculated using a 1:1 Langmuir binding model. The raw data sets were analyzed using Biacore T200 Evaluation Software (version 1.0, GE Healthcare), and the sensorgrams of the reference flowcells were subtracted from the sensorgrams of the sample-captured flowcells.

Example 20

Cell Free PCSK9-LDLR TR-FRET Assay

Secreted PCSK9 facilitates the degradation of hepatic LDLR, leading to increase in serum LDL-C level. Thus the PCSK9-specific lipocalin muteins which interfere with the interaction between PCSK9 and LDLR, result in enhancement of the recycling of LDLR to plasma membrane, which activates LDL-C intake and eventually lower the circulating LDL-C levels.

Cell free TR-FRET assay was used to determine the inhibitory effect of the lipocalin muteins (SEQ ID NO: 62, SEQ ID NO: 82, SEQ ID NO: 83 and SEQ ID NO: 84) on the binding between PCSK9 and LDLR. Biotin-labeled hPCSK9 (biotin-hPCSK9) used in the assay was prepared by incubation with a 5 times molar excess of EZ-Link NHSChromogenic Biotin reagent (Thermo Scientific) for 1 hr at room temperature and excess of biotin was removed by illustra NAP column (GE Healthcare Life Science). Europium-labeled LDLR (Eu-LDLR) was prepared as described in the previous report (Fisher T S, et al., J. Biol. Chem. (2007) 282(28), 20502-20512).

Cell free PCSK9-LDLR TR-FRET assay was performed in 384 well format. A final concentration of 20 nM of Biotin-hPCSK9 was incubated with several concentrations of test lipocalin muteins in binding buffer (10 mM HEPES, pH 7.4, 150 mM NaCl, 0.1 mM CaCl$_2$, and 0.05% (w/v) BSA) for two hours at room temperature in the presence or absence of 34 mg/ml of human serum albumin. Then ten microliter of above biotin-hPCSK9-lipocalin solution and ten microliter of Eu-LDLR/Alexa-SA solution (1.0 nM of Eu-LDLR, 80 nM of streptavidin/Alexa Fluor 647 conjugate (Invitrogen), 10 mM HEPES, pH 7.4, 150 mM NaCl, 0.1 mM CaCl$_2$, and 0.05% (w/v) BSA) was mixed in the well and incubated for two hours at room temperature in the dark followed by incubation overnight in the refrigerator. Samples were read using a BMG Lab Systems Rubystar Reader set to read 20 flasheswell with a 50-μs integration delay and a 200-μs integration time for a total read time of 1100 ms/well. FRET was quantified by measurement of the emission ratio at 665/620 nm. TR-FRET ratio was calculated as following formulation.

TR-FRET Ratio=(counts at 665 nm counts at 620 nm)×10,000

To obtain the lipocalin mutein concentration at which formation of the PCSK9/LDLR complex was blocked by 50% (IC50), the curves were fitted by nonlinear regression with a single-site binding model. Curve fitting was performed using Kaleida Graph ver 4.1.1 software. (Synergy Software)

The resulting calculated IC50 values are summarized in Table 11 below Example 21.

Example 21

In Vivo Plasma Half-life of PCSK9-specific Lipocalin Muteins

The conjugation of lipocalin muteins with a moiety that can target a specific body region, organism, tissue, organ or cell may extend the half-life of the lipocalin muteins in the body. For example, half-life of human serum albumin (HSA) was reported to be 19 days (Biochimica et Biophysica Acta 1830; 5526-5534, 2013) and therefore PCSK9-specific lipocalin muteins (SEQ ID NO: 62 and SEQ ID NO: 82) were conjugated to an albumin binding protein (such as G148 and SEQ ID NO: 85) that binds to HSA, and therefore, may exhibit long half-life in the body for the lipocalin muteins.

To observe the effect of conjugation with albumin binding protein and to determine plasma long half-life of PCSK9-specific lipocalin muteins, several tested lipocalin muteins were intravenously administered to normal rats and plasma concentrations of the lipocalin muteins were measured using sandwich ELISA. Blood sampling for determination of plasma half-life was conducted at various time points following administration of test lipocalin muteins.

The resulting plasma half-lifes for the four lipocalin muteins are summarized in Table 11 as below. For example the data shows that lipocalin muteins conjugated to a moiety that can bind to HSA exhibit longer halflife than lipocalin muteins alone.

TABLE 11

| Molecule | Biacore_Anti PCSK9 | | | Biacore_Anti HSA | | | LDLR binding (IC50, nM) | | |
|---|---|---|---|---|---|---|---|---|---|
| | ka (1/Ms) | ka (1/s) | KD (M) | ka (1/Ms) | ka (1/s) | KD (M) | w/o HSA | w/ HSA | T½ (h) |
| SEQ ID NO: 62 | 1.1E+05 | 2.9E−04 | 2.6E−10 | — | — | — | 1.36 | 0.93 | 0.99 |
| SEQ ID NO: 82 | 1.5E+05 | 3.7E−04 | 2.5E−10 | — | — | — | 1.68 | 1.33 | 0.86 |
| SEQ ID NO: 83 | 7.1E+05 | 2.7E−04 | 3.8E−10 | 2.2E+06 | 4.2E−05 | 1.9E−11 | 1.93 | 1.26 | 24 |
| SEQ ID NO: 84 | 7.5E+05 | 3.0E−04 | 3.9E−10 | 2.4E+06 | 3.0E−05 | 1.3E−11 | 1.09 | 1.09 | 32 |

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims

The invention claimed is:

1. A mutein of human tear lipocalin, wherein the mutein comprises:
   (a) a mutated amino acid residue at any one or more of the sequence positions 26-34, 56-58, 80, 83, 104-106 and 108 of the linear polypeptide sequence of the mature human tear lipocalin, wherein the mutein comprises at least one of the following amino acid substitutions in comparison to mature human tear lipocalin: (i) Arg 26→Ser, Phe, Trp, His or Thr and (ii) Glu 34→Asn, Thr, Arg or Gly; and
   (b) a mutated amino acid residue at any one or more of the sequence positions 61, 101, 111, 114 and 153 of the linear polypeptide sequence of the mature human tear lipocalin,
   and wherein the mutein binds specifically to proprotein convertase subtilisin/kexin type 9 (PCSK9).

2. The lipocalin mutein according to claim 1, wherein the mutein binds to a non-human primate PCSK9 or to an immunogenic fragment thereof with a dissociation constant (KD) equal to or less than 10 nM.

3. The lipocalin mutein according to claim 1, wherein the mutein binds to mouse PCSK9 or to an immunogenic fragment thereof with a dissociation constant ($K_D$) equal to or less than 10 nM.

4. The lipocalin mutein according to claim 1, wherein the mutein binds to human PCSK9 or to a fragment thereof with a dissociation constant ($K_D$) equal to or less than 10 nM.

5. The lipocalin mutein according to claim 1, wherein the mutein binds to human PCSK9 or to a fragment thereof with a dissociation constant ($K_D$) equal to or less than 1 nM.

6. The lipocalin mutein according to claim 1, wherein the mutein binds to human PCSK9 or to a fragment thereof with a dissociation constant ($K_D$) equal to or less than 0.1 nM.

7. The lipocalin mutein according to claim 1, wherein mutein binds to human PCSK9 or to a fragment thereof with a dissociation constant ($K_D$) equal to or less than 1 pM.

8. The mutein according to claim 1, wherein the mutein comprises at least one of the following amino acid substitutions in comparison to mature human tear lipocalin: Arg 26→Ser, Phe, Trp, His or Thr.

9. The mutein according to claim 1, wherein the mutein comprises at least one of the following amino acid substitutions in comparison to mature human tear lipocalin: Glu 34→Asn, Thr, Arg or Gly; Leu 56→Met, Ser, Gln, Phe, His or Asn.

10. The mutein according to claim 1, wherein the mutein comprises at least one of the following amino acid substitutions in comparison to mature human tear lipocalin: Ser 58→Lys, Ala, Arg, Trp or Pro.

11. The mutein according to claim 1, wherein the mutein comprises at least one of the following amino acid substitutions in comparison to mature human tear lipocalin: Met 31→Ala, Gly, His, Pro, Ser Aps, Glu or Gln.

12. The mutein according to claim 1, wherein the mutein comprises at least one of the following amino acid substitutions in comparison to mature human tear lipocalin: Leu 33→Tyr, Trp, Tyr, Phe, Pro or Ala.

13. The mutein according to claim 1, wherein the mutein comprises at least one of the following amino acid substitutions in comparison to mature human tear lipocalin: Ser 61→Trp or Phe; Asp 80→Ser, Met, Pro, Ile, Gln, Tyr, Ser, Val or Thr.

14. The mutein according to claim 1, wherein the mutein comprises at least one of the following amino acid substitutions in comparison to mature human tear lipocalin: Glu 104→Leu, Pro, Ser, Ala, Asn, Thr, Lys or Asp.

15. The mutein according to claim 1, wherein the mutein comprises at least one of the following amino acid substitutions in comparison to mature human tear lipocalin: His 106→Pro, Gln, Gly, Arg, Val, Thr, Asn or Leu.

16. The mutein according to claim 1, wherein the mutein comprises at least one of the following amino acid substitutions in comparison to mature human tear lipocalin: Lys 108→Gln, Ala, Trp, Tyr, Arg, Asp, Asn, Ser, Glu or Thr.

17. The mutein according to claim 1, wherein the mutein comprises at least one of the following amino acid substitutions in comparison to mature human tear lipocalin: Glu 27→Arg, Ser, Gln, Thr, Phe, Lys, Ala or Arg.

18. The mutein according to claim 1, wherein the mutein comprises at least one of the following amino acid substitutions in comparison to mature human tear lipocalin: Pro 29→Gly, Asp, Asn, Ile, Leu or Met.

19. The mutein according to claim 1, wherein the mutein comprises at least one of the following amino acid substitutions in comparison to mature human tear lipocalin: Asn 32→Ile, Leu, Tyr, Met or Trp.

20. The mutein according to claim 1, wherein the mutein comprises at least one of the following amino acid substitutions in comparison to mature human tear lipocalin: Leu 105→Cys, Tyr, Trp, Glu, Arg, Ser, His, Ala, Val, Asp, Pro, Gly or Lys.

21. The mutein according to claim 1, wherein the mutein comprises at least one of the following amino acid substitutions in comparison to mature human tear lipocalin: Phe 28→Cys, Arg, Lys, Trp, Asp, Gly, His, Leu or Asn.

22. The mutein according to claim 1, wherein the mutein comprises at least one of the following amino acid substitutions in comparison to mature human tear lipocalin: Glu 30→Arg, Asp, Thr, Ser, Gly, Ala or Asn.

23. The mutein according to claim 1, wherein the mutein comprises at least one of the following amino acid substitutions in comparison to mature human tear lipocalin: Ile 57→Tyr, Trp, His, Gln, Thr or Arg.

24. The mutein according to claim 1, wherein the mutein comprises at least one of the following amino acid substitutions in comparison to mature human tear lipocalin: Lys 83→Arg, Ser, Gln, Thr or Glu.

25. The mutein according to claim 1, comprising one of the following sets of amino acid substitutions in comparison to mature human tear lipocalin:
 (a) Arg 26→Phe; Asn 32→Ile; Glu 34→Thr; Leu 56→Met; Ser 58→Ala and Lys 83→Ser,
 (b) Arg 26→Trp; Asn 32→Leu; Glu 34→Thr; Leu 56→Ser and Ser 58→Ala,
 (c) Arg 26→His; Asn 32→Tyr; Glu 34→Thr; Leu 56→Ser; Ser 58→Arg and Lys 83→Gln;
 (d) Arg 26→Phe; Asn 32→Met; Glu 34→Thr; Leu 56→Gln; Ser 58→Ala and Lys 83→Thr;
 (e) Asn 32→Trp; Glu 34→Arg; Leu 56→Asn; Ser 58→Trp and Lys 83→Ser,
 (f) Arg 26→Phe; Asn 32→Leu; Glu 34→Thr; Leu 56→Phe; Ser 58→Ala and Lys 83→Arg,
 (g) Arg 26→Thr; Asn 32→Trp; Glu 34→Asn; Leu 56→His; Ser 58→Pro and Lys 83→Ser,
 (h) Asn 32→Trp; Glu 34→Asn; Leu 56→Phe; Ser 58→Arg and Lys 83→Glu,
 (i) Arg 26→Trp; Asn 32→Leu; Glu 34→Thr; Leu 56→Met; Ser 58→Ala and Lys 83→Ser, or
 (j) Asn 32→Trp; Glu 34→Gly; Leu 56→Gln; Ser 58→Ala and Lys 83→Gln.

26. The mutein according to claim 1, comprising one of the following sets of amino acid substitutions in comparison to mature human tear lipocalin:
 (a) Glu 27→Ser; Phe 28→Arg; Pro 29→Gly; Glu 30→Asp; Met 31→Ala; Leu 33→Trp; Ile 57→Tyr; Asp 80→Met; Glu 104→Pro; Leu 105→Tyr; His 106→Gln; Lys 108→Ala,
 (b) Glu 27→Gln; Phe 28→Cys; Pro 29→Asp; Glu 30→Thr; Met 31→Gly; Leu 33→Trp; Ile 57→Tyr; Leu 105→Cys; His 106→Gly; Lys 108→Trp,
 (c) Glu 27→Glu; Phe 28→Trp; Pro 29→Asn; Glu 30→Gly; Met 31→His; Leu 33→Tyr; Ile 57→Tyr; Asp 80→Pro; Glu 104→Ser; Leu 105→Trp; His 106→Pro; Lys 108→Tyr,
 (d) Glu 27→Thr; Phe28→Asp; Pro 29→Asn; Glu 30→Ser; Met 31→Pro; Leu 33→Phe; Ile 57→Tyr; Asp 80→Ile; Glu 104→Ala; Leu 105→Glu; His 106→Arg; Lys 108→Arg,
 (e) Glu 27→Phe; Phe 28→Lys; Pro 29→Ile; Glu 30→Ala; Met 31→Ser; Leu 33→Pro; Ile 57→Trp; Asp 80→Gln; Glu 104→Asn; Leu 105→Arg; His 106→Gln; Lys 108→Asp,
 (f) Glu 27→Lys; Phe 28→Gly; Pro 29→Pro; Glu 30→Thr; Met 31→Pro; Leu 33→Trp; Ile 57→His; Asp 80→Tyr; Glu 104→Ala; Leu 105→Ser; His 106→Val; Lys 108→Asn,
 (g) Glu 27→Glu; Phe 28→His; Pro 29→Leu; Glu 30→Ala; Met 31→Asp; Leu 33→Ala; Ile 57→Gln; Asp 80→Ile; Glu 104→Ala; Leu 105→Tyr; His 106→Pro; Lys 108→Ser,
 (h) Glu 27→Ala; Phe 28→Asp; Pro 29→Met; Glu 30→Gly; Met 31→Asp; Leu 33→Pro; Ile 57→Thr; Asp 80→Thr; Glu 104→Thr; His 106 →Thr; Lys 108→Arg,
 (i) Glu 27→Arg; Phe 28→Leu; Pro 29→Asp; Glu 30→Asn; Met 31→Glu; Leu 33→Trp; Ile 57→Tyr; Asp 80→Gln; Glu 104→Pro; Leu 105→Arg; His 106→Asn; Lys 108→Ala,
 (j) Glu 27→Lys; Phe 28→Asn; Pro 29→Met; Glu 30→Gly; Met 31→Gln; Leu 33→Pro; Ile 57→Arg; Asp 80→Ile; Glu 104→Asp; Leu 105→Arg; His 106→Leu; Lys 108→Thr, or
 (k) Glu 27→Ser; Phe 28→Arg; Pro 29→Gly; Glu 30→Asp; Met 31→Ala; Leu 33→Trp; Ile 57→Tyr; Asp 80→Met; Glu 104→Pro; Leu 105→Gly; His 106→Gln; Lys 108→Ala.

27. The mutein according to claim 1, comprising the following combination of amino acid substitutions: Arg 26→Phe; Glu 27→Ser; Phe 28→Arg; Pro 29→Gly; Glu 30→Asp; Met 31→Ala; Asn 32→Ile; Leu 33→Trp; Glu 34→Thr; Leu 56→Met; Ile 57→Tyr; Ser 58→Ala; Lys 83→Ser; Glu 104→Pro and Lys 108→Thr, in comparison to mature human tear lipocalin.

28. The mutein according to claim 27, further includes one or more of the following amino acid substitutions in comparison to mature human tear lipocalin: Thr 43→Ile or Ala; Glu 45→Gly; Asn 48→Gly; Glu 63→Gly; Ala 66→Vla; Glu 69→Vla; Lys 70→Arg; Ala 79→Thr, Met or Vla; Asp 80→Met or Ser; Gly 82→Ser; His 84→Gln; Vla 85→Gly; Tyr 87→Ser; Ile 88→Thr or Leu; His 92→Pro; Leu 105→His, Gly or Tyr; and His 106→Gln or Arg.

29. The mutein according to claim 1, comprising the following combination of amino acid substitutions: Glu 27→Phe; Phe 28→Lys; Pro 29→Ile; Asn 32→Trp; Leu 33→Pro; Glu 34→Arg; Leu 56→Asn; Ile 57→Trp; His 106→Gln and Lys 108→Glu, in comparison to mature human tear lipocalin.

30. The mutein according to claim 29, further includes one or more of the following amino acid substitutions in comparison to mature human tear lipocalin: Glu 43→Gly or Ala; Glu 45→Gly; Ser 58→Trp or Arg; Glu 63→Asp; Glu 69→Gly; Lys 70→Arg; Asp 80→Gln, Val or Thr; Gly 82→Asp; Lys 83→Ser or Arg; Ala 86→Glu or Ser; Phe 99→Leu; Glu 102→Lys or Val; Glu 104→Asn or Lys; and Pro 106→Thr.

31. The mutein according to claim 1, wherein the mutein comprises an amino acid substitution of a native amino acid by a cysteine residue at positions 28 or 105 with respect to the amino acid sequence of mature human tear lipocalin.

32. The mutein according to claim 1, wherein the mutein has at least 85% identity to the sequence of mature human tear lipocalin.

33. The mutein of claim 1, wherein the mutein has an amino acid sequence as set forth in any one of SEQ ID NOs: 3-28, 62-71 and 82.

34. The mutein of claim 1, wherein the mutein has an amino acid sequence as set forth in SEQ ID NO: 23.

35. The mutein of claim 1, wherein the mutein has an amino acid sequence as set forth in SEQ ID NO: 13.

36. The mutein of claim 1, wherein the mutein has an amino acid sequence as set forth in SEQ ID NO: 20.

37. The mutein of claim 1, wherein the mutein has an amino acid sequence as set forth in SEQ ID NO: 22.

38. The mutein of claim 1, wherein the mutein is conjugated to a label moiety.

39. The mutein of claim 1, wherein the mutein is conjugated to a moiety that can target a specific body region, organism, tissue, organ or cell within a subject.

40. The mutein of claim 1, wherein the mutein is conjugated to a moiety that can extend the serum half-life of the mutein.

41. The mutein of claim 1, wherein the mutein is conjugated to a polyalkylene glycol molecule.

42. The conjugated mutein of claim 41, wherein the conjugated mutein comprises an amino acid sequence as set forth in any one of SEQ ID NOs: 30-32.

43. The mutein of claim 1, wherein the mutein is conjugated to an albumin binding protein.

44. The conjugated mutein of claim 43, wherein the conjugated mutein comprises an amino acid sequence as set forth in any one of SEQ ID NOs: 83-84.

45. The mutein of claim 1, wherein the mutein is fused to a moiety which can confer new characteristics to the fusion.

46. The mutein of claim 1, wherein the mutein comprises four loops of one of SEQ ID NOs: 3-28, 62-71 and 82 which together define a binding pocket for PCSK9.

47. The mutein of claim 1, wherein the mutein comprises four loops of SEQ ID NO: 23 which together define a binding pocket for PCSK9.

48. The mutein of claim 1, wherein the mutein comprises four loops of SEQ ID NO: 13 which together define a binding pocket for PCSK9.

49. The mutein of claim 1, wherein the mutein comprises four loops of SEQ ID NO: 20 which together define a binding pocket for PCSK9.

50. The mutein of claim 1, wherein t the mutein comprises the four loops of SEQ ID NO: 22 which together define a binding pocket for PCSK9.

51. A kit comprising a mutein according to claim 1.

52. A method of binding of PCSK9 in a subject, comprising administering to said subject either a mutein according to claim 1, or a composition comprising such mutein, in an amount sufficient for binding PCSK9.

53. A method of inhibiting the binding of PCSK9 to low density lipoprotein receptors (LDL-R) in a subject, comprising administering to said subject either a mutein according to claim 1, or a composition comprising such mutein, in an amount sufficient for inhibiting the binding of PCSK9 to LDL-R.

54. A method for detection of PCSK9, comprising:
(a) contacting a mutein according to claim 1 with a test sample suspected to contain PCSK9 under suitable conditions, thereby allowing the formation of a complex between the mutein and PCSK9 or a domain or fragment thereof, and
(b) detecting the complex by a suitable signal.

55. A method for the separation of PCSK9 from a sample, comprising:
(a) contacting a mutein according to claim 1 with a sample supposed to contain PCSK9 under suitable conditions, thereby allowing formation of a complex between the mutein and PCSK9 or a domain or fragment thereof, and
(b) separating the complex from the sample.

56. A method for targeting a compound to a preselected organism, tissue, organ or cell to be treated with the compound, comprising the steps of:
(a) conjugating a mutein according to claim 1 with said compound, and
(b) delivering the mutein/compound complex to the preselected organism, tissue, organ or cell.

* * * * *